United States Patent
Accetta et al.

(10) Patent No.: US 11,147,812 B2
(45) Date of Patent: Oct. 19, 2021

(54) TYROSINE ANALOGUES DERIVATIVES AS RHO-KINASE INHIBITORS

(71) Applicant: Chiesi Farmaceutici S.p.A., Parma (IT)

(72) Inventors: Alessandro Accetta, Parma (IT); Anna Maria Capelli, Parma (IT); Fabio Rancati, Parma (IT); Gurdip Bhalay, Parma (IT); Arnaud Jean Francois Auguste Cheguillaume, Parma (IT); Christine Edwards, Parma (IT); Patrizia Tisselli, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 43 days.

(21) Appl. No.: 16/639,486

(22) PCT Filed: Sep. 5, 2018

(86) PCT No.: PCT/EP2018/073872
§ 371 (c)(1),
(2) Date: Feb. 14, 2020

(87) PCT Pub. No.: WO2019/048479
PCT Pub. Date: Mar. 14, 2019

(65) Prior Publication Data
US 2021/0023080 A1   Jan. 28, 2021

(30) Foreign Application Priority Data
Sep. 7, 2017   (EP) .................................. 17189933

(51) Int. Cl.
| | |
|---|---|
| *C07D 471/04* | (2006.01) |
| *A61K 31/4995* | (2006.01) |
| *A61K 31/496* | (2006.01) |
| *C07D 487/08* | (2006.01) |
| *A61K 9/00* | (2006.01) |
| *A61K 31/437* | (2006.01) |

(52) U.S. Cl.
CPC ........ *A61K 31/4995* (2013.01); *A61K 9/0073* (2013.01); *A61K 31/437* (2013.01); *A61K 31/496* (2013.01); *C07D 471/04* (2013.01); *C07D 487/08* (2013.01)

(58) Field of Classification Search
CPC .... A61K 31/4995; A61K 9/00; A61K 31/496; A61K 31/437; C07D 471/04; C07D 487/08
USPC ...................................................... 514/249
See application file for complete search history.

(56) References Cited

U.S. PATENT DOCUMENTS 8,329,716 B2   12/2012   Shirok et al.

FOREIGN PATENT DOCUMENTS

| WO | WO 2005/097790 A1 | 10/2005 | |
|---|---|---|---|
| WO | WO 2006/009889 A1 | 1/2006 | |
| WO | 2018/138293 | * | 8/2018 |

OTHER PUBLICATIONS

International Search Report and Written Opinion for International Application No. PCT/EP2018/073872, European Patent Office, Netherlands, dated Oct. 31, 2018, 8 pages.
Kast, R., et al., "Cardiovascular effects of a novel potent and highly selective azaindole-based inhibitor of Rho-kinase," British Journal of Pharmacology, 152: 1070-1080, Nature Publishing Group, Germany (2007).
Schirok, H., et al., "Improved Synthesis of the Selective Rho-Kinase Inhibitor 6-Chloro-N4-{3,5-difluoro-4 [(3-methyl-1H-pyrrolo[2.3 -b]pyridin-4-yl)oxy]phenyl}pyrimidin-2,4-diamine," Organic Process Research & Development,14(12): 168-173, American Chemical Society, United States (2010).
Bond, L., et al., "Rho kinase as a target for cerebral vascular disorders," Future Med Chem 7(8):1039-53, Future Science Ltd, United States (2015).
Duong-Quy, S., et al., "Role of Rho-kinase and its inhibitors in pulmonary hypertension," Pharmacol Ther. 137(3):352-64, Elsevier, Netherlands (2013).

(Continued)

*Primary Examiner* — Niloofar Rahmani
(74) *Attorney, Agent, or Firm* — Sterne, Kessler, Goldstein & Fox P.L.L.C.

(57) ABSTRACT

The invention relates to compounds of formula (I) inhibiting Rho Kinase that are tyrosine analogues derivatives, methods of preparing such compounds, pharmaceutical compositions containing them and therapeutic use thereof. Particularly the compounds of the invention may be useful in the treatment of many disorders associated with ROCK enzymes mechanisms, such as pulmonary diseases including asthma, chronic obstructive pulmonary disease (COPD), idiopathic pulmonary fibrosis (IPF) and pulmonary arterial hypertension (PAH).

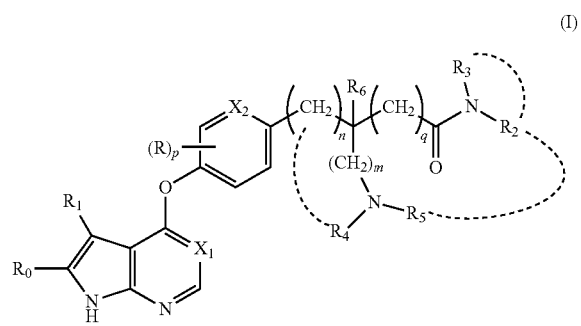

14 Claims, No Drawings

(56) References Cited

OTHER PUBLICATIONS

Feng, Y., et al., "Rho Kinase (ROCK) Inhibitors and Their Therapeutic Potential," J Med Chem 59(6):2269-300, American Chemistry Society, United States (Mar. 2016).
Fernandes, LB., et al., "Rho kinase as a therapeutic target in the treatment of asthma and chronic obstructive pulmonary disease," Ther Adv Respir Dis. 1(1):25-33, Sage Publisher, United States (2007).
Gosens, R., et al., "Rhokinase as a drug target for the treatment of airway hyperresponsiveness in asthma," Mini-Rev. Med. Chem. 6:339-348, Bentham Science Publishers, United Arab Emirates (2006).
Hartmann, S, et al., "The Function of Rho-Associated Kinases ROCK1 and ROCK2 in the Pathogenesis of Cardiovascular Disease," Front Pharmacol. 20(6):276, Frontiers Media, United States (2015).
Huang, Y., et al., "Role of Rho kinase signal pathway in inflammatory bowel disease," Int J Clin Exp Med. 8(3): 3089-3097, e-Century Publishing Corporation, United States (2015).
Inoue, T., et al., "Rho-associated kinase inhibitors: a novel glaucoma therapy," Prog Retin Eye Res 37:1-12, Elsevier, Netherlands (2013).
Jiang, C., et al., "Fasudil, a rho-kinase inhibitor, attenuates bleomycin-induced pulmonary fibrosis in mice," Int. J. Mol. Sci.13:8293-8307, MDPI, Switzerland (2012).
Komers, R., et al., "Rho kinase inhibition in diabetic kidney disease," Br J Clin Pharmacol. 76(4):551-9, British Journal of Clinical Pharmacology, United Kingdom (2013).
Kubo, T., et al., "Rho-ROCK inhibitors as emerging strategies to promote nerve regeneration," Curr Pharm Des 13(24):2493-9, Bentham Science Publishers, United Arab Emirates (2007).
Lee, D., et al., "Targeted disruption of ROCK1 causes insulin resistance in vivo," J. Biol. Chem 284:11776-11780 (with supplementary data), American Society for Biochemistry and Molecular Biology, United States (2009).
Li, Q., et al., "Inhibition of Rho-kinase ameliorates myocardial remodeling and fibrosis in pressure overload and myocardial infarction: role of TGF-β1-TAK1," Toxicol Lett. 211(2):91-7, Elsevier, Netherlands (2012).
Lograsso, P., et al., "Rho kinase inhibitors and their application to inflammatory disorders," Curr. Top. Med. Chem 9:704-723, Bentham Science Publishers, United Arab Emirates (2009).

Mueller, B., et al., "Rho kinase, a promising drug target for neurological disorders," Nat. Rev. Drug Discovery 4:387-398, Nature Publishing Group, United Kingdom (2005).
Riento, K., et al., "Rocks: Multifunctional Kinases in Cell Behaviour," Nat. Rev. Mol. Cell Biol. 4:446-456, Nature, United Kingdom (2003).
Shi, J., et al., "Rho kinases in cardiovascular physiology and pathophysiology: the effect of fasudil," J Cardiovasc Pharmacol. 62(4):341-54, SAGE Publications, United States (2013).
Shimizu, T., et al., "Rho Kinases and Cardiac Remodeling," Circ J. 80(7):1491-8, J-STAGE, Japan (Jun. 2016).
Sopko, N.A., et al., "Understanding and targeting the Rho kinase pathway in erectile dysfunction," Nat Rev Urol. 11(11):622-8, Nature Publishing Group, United Kingdom (2014).
Stirzaker, R.A et al., "Administration of fasudil, a ROCK inhibitor, attenuates disease in lupus-prone NZB/W F1 female mice," Lupus 21(6):656-61, SAGE Publications, United States (2012).
Suzuki, Y., et al., "Safety and efficacy of fasudil monotherapy and fasudil-ozagrel combination therapy in patients with subarachnoid hemorrhage: sub-analysis of the post-marketing surveillance study," Neurol Med Chir. 48(6):241-7, J-Stage, Japan (2008).
Tanihara, H., et al., "K-115 Clinical Study Group. One-year clinical evaluation of 0.4% ripasudil (K-115) in patients with open-angle glaucoma and ocular hypertension," Acta Ophthalmol 94(1):e26-34, Wiley Online Library, United States (Feb. 2016).
Wei, L., et al., "Novel Insights into the Roles of Rho Kinase in Cancer," Arch Immunol Ther Exp (Warsz) 64(4):259-78, Springer, United Staes (Aug. 2016).
Yiu, Z.Z., et al., "Novel Oral Therapies for Psoriasis and Psoriatic Arthritis," Am J Clin Dermatol. 17(3):191-200, Springer Nature, United States (Jun. 2016).
Yoshimi, E., et al., "Antinociceptive effects of AS1892802, a novel rho kinase inhibitor, in rat models of inflammatory and noninflammatory arthritis," J. Pharmacol. Exp. Ther. 334;955-963, American Society for Pharmacology and Experimental Therapeutics, United States (2010).
Yu, J.Z., et al., "Therapeutic potential of experimental autoimmune encephalomyelitis by Fasudil, a Rho kinase inhibitor," J Neurosci Res 88(8):1664-72, Wiley Online Library, United States (2010).
Zanin-Zhorov, A., et al., "Isoform-specific targeting of ROCK proteins in immune cells," Small GTPases 7(3):173-177, Taylor & Francis, United States (Jul. 2016).

* cited by examiner

TYROSINE ANALOGUES DERIVATIVES AS RHO-KINASE INHIBITORS

FIELD OF THE INVENTION

The present invention relates to compounds inhibiting Rho Kinase (hereinafter ROCK Inhibitors); particularly the invention relates to compounds that are tyrosine analogues derivatives, methods of preparing such compounds, pharmaceutical compositions containing them and therapeutic use thereof.

More particularly, the compounds of the invention are inhibitors of the activity or function of the ROCK-I and/or ROCK-II isoforms of the Rho-associated coiled-coil forming protein kinase (ROCK).

Therefore, the compounds of the invention may be useful in the treatment of many disorders associated with ROCK enzymes mechanisms, such as pulmonary diseases including asthma, chronic obstructive pulmonary disease (COPD), idiopathic pulmonary fibrosis (IPF) and pulmonary arterial hypertension (PAH).

BACKGROUND OF THE INVENTION

Rho-associated coiled-coil forming protein kinase (ROCK) belongs to the AGC (PKA/PKG/PKC) family of serine-threonine kinases. Two human isoforms of ROCK have been described. ROCK-I (also referred to as p160 ROCK or ROKβ) and ROCK-II (ROKα) are approximately 160 kDa proteins containing an N-terminal Ser/Thr kinase domain, followed by a coiled-coil structure, a pleckstrin homology domain, and a cysteine-rich region at the C-terminus (Riento and Ridley, 2003).

Both ROCK-II and ROCK-I are expressed in many human and rodent tissues including the heart, pancreas, lung, liver, skeletal muscle, kidney and brain (Riento and Ridley, 2003). ROCK has been identified as an effector molecule of RhoA, and is involved in a variety of cell functions, including actin organization, cell adhesion, cell migration and cytokinesis (Riento and Ridley, 2003; Feng et al., 2016). It is also involved in regulating smooth muscle contraction, through the phosphorylation of effectors such as myosin light chain phosphatase (MLC). Indeed ROCK plays an important role in signal transduction initiated by several agents regulating smooth muscle cell contraction in blood vessels and/or airways, including serotonin, angiotensin II, endothelin I, platelet derived growth factor (PDGF) and urotensin II (Li et al., 2012; Shi et al., 2013). To date only two ROCK inhibitors have been approved for clinical use, in Japan and/or in China: Fasudil (Suzuki et al., 2008) was approved in 1995 for the treatment of cerebral vasospasm, and ripasudil (Tanihara et al., 2016) was approved in 2014 for the treatment of glaucoma.

ROCK mediated vasoconstriction and endothelial dysfunction are two key components of several cardiovascular diseases, including hypertensive heart disease, coronary artery diseases, atherosclerosis, restenosis, Raynaud phenomenon, stroke and glaucoma (Hartmann et al., 2015). In particular, pharmacological data from clinical trials show that ROCK inhibitors decrease intraocular pressure and demonstrate beneficial effects in glaucoma patients (Inoue and Tanihara, 2013). In patients with pulmonary hypertension, ROCK activity is significantly higher in both lung tissues and circulating neutrophils as compared with controls (Duong-Quy et al., 2013). A significant correlation was established between neutrophil ROCK activity and the severity and duration of pulmonary hypertension (Duong-Quy et al., 2013). ROCK can also contribute to the development of cardiac fibrosis, hypertrophy, and subsequent heart failure. Recent experimental studies using ROCK inhibitors, such as fasudil, have shown the benefits of ROCK inhibition in cardiac remodeling (Li et al., 2012). Mice lacking each ROCK isoform also exhibit reduced myocardial fibrosis in a variety of pathological models of cardiac remodeling (Shimizu and Liao, 2016).

ROCK is also a promising target for the treatment of cerebral vascular disorders. Indeed, preclinical studies indicate that Rho kinase inhibition may reduce the formation/growth/rupture of both intracranial aneurysms and cerebral cavernous malformations (Bond et al., 2015).

RhoA-ROCK signalling is important in maintaining a flaccid penile state, and pharmacological inhibition of ROCK signalling potentiates smooth-muscle relaxation in an NO-independent manner, suggesting that ROCK is a new therapeutic target for the treatment of erectile dysfunction (Sopko et al., 2014).

ROCK activity is an important signaling mechanism in leucocyte-platelet-endothelium interaction, leucocyte extravasation and oedema. Overactivation of Rho kinase in endothelial cells causes leakiness by disruption of cell-cell junctions favouring inflammatory cell recruitment. Taken together, this evidence points toward a role of ROCK in pathological conditions associated with acute and chronic inflammation as well as autoimmune diseases. In particular, contribution of the ROCK pathway to autoimmunity and autoimmune disease is emerging (Zanin-Zhorov et al., 2016). This is supported by the demonstration of the role of ROCK signaling in T-cell development and function, including adhesion, chemotactic responses, and antigen-dependent activation, as well as the beneficial effect of ROCK inhibition in experimental models of rheumatoid arthritis and lupus (LoGrasso et al., 2009; Yoshimi et al., 2010; Stirzaker et al., 2012). The inhibitory effect of Fasudil on T-cell migration might expand its clinical application as a new therapy for multiple sclerosis (Yu et al., 2010). Accumulating evidence also demonstrates that ROCK plays a key role in regulating three essential factors for pathogenesis of inflammatory bowel disease (IBD): disruptions of the intestinal barrier, exposure of the luminal content to mucosal immune cells and an abnormal immune response (Huang et al., 2015). The clinical use of ROCK inhibitors is under scrutiny also in psoriasis (Yiu and Warren, 2016).

There are several lines of evidence that ROCKs play a role in the pathology of diabetes. Indeed, ROCK1 KO mice exhibit insulin resistance and can have a significant increase in glucose-induced insulin secretion, leading to hyperinsulinemia (Lee et al., 2009). In addition, studies in models of type 1 and type 2 diabetes have indicated blood pressure-independent nephroprotective actions of ROCKi in diabetic kidney disease (Komers, 2013).

There is now substantial evidence that ROCK is involved in many of the pathways that contribute to the pathologies associated with several acute and chronic pulmonary diseases, including asthma, COPD, bronchiectasis and ARDS/ALI. Given the biological effect of ROCK, selective inhibitors have the potential to treat a number of pathological mechanisms in respiratory diseases, such as smooth muscle hyper-reactivity, bronchoconstriction, airway inflammation and airway remodeling, neuromodulation and exacerbations due to respiratory tract viral infection (Fernandes et al., 2007). Indeed the Rho kinase inhibitor Y-27632 causes bronchodilatation and reduces pulmonary eosinophilia trafficking and airways hyperresponsiveness (Gosens et al., 2006). Pulmonary ROCK activation has been demonstrated in humans with idiopathic pulmonary fibrosis (IPF) and in animal models of this disease. ROCK inhibitors can prevent fibrosis in these models, and more importantly, induce the regression of already established fibrosis, thus indicating ROCK inhibitors as potential powerful pharmacological agents to halt progression of pulmonary fibrosis (Jiang et al., 2012).

Accumulating evidence supports the concept that ROCK plays important roles in tumor development and progression through regulating many key cellular functions associated with malignancy, including tumorigenicity, tumor growth, metastasis, angiogenesis, tumor cell apoptosis/survival and chemoresistance (Wei et al., 2016). Thus, indicating ROCK inhibitors also as potential powerful pharmacological agents in cancer.

The administration of an oral ROCK inhibitor effectively ameliorates clinical manifestations in experimental models of graft-vs.-host disease (GVHD). (Biol Blood Marrow Transplant. 2014; 20(8):1104-11; Blood. 2016; 127(17): 2144-54). Further findings highlight the Rho kinases as rational therapeutic targets to combat tau accumulation in Progressive Supranuclear Palsy (PSP) and Corticobasal Degeneration (CBD). (Gentry et al., J Neurosci. 2016; 36(4):1316-23).

In various disorders of the central nervous system there is an abnormal activation of the Rho/ROCK pathway. ROCK is activated upon injury to the adult brain and spinal cord and inhibition of ROCKs results in accelerated regeneration and enhanced functional recovery after spinal-cord injury (Kubo et al., 2007). Inhibition of the Rho/ROCK pathway has also proved to be efficacious in animal models of stroke, inflammatory and demyelinating diseases, Alzheimer's disease and neuropathic pain (reviewed by Muller et al., 2005).

Various compounds have been described in the literature as Rho Kinase Inhibitors. See e.g. WO2004/039796; WO2006/009889; WO2010/032875; WO2009/079008; WO2014/118133.

There remains a potential for developing novel and pharmacologically improved ROCK inhibitors in many therapeutic areas such as: cardiovascular and respiratory diseases, erectile dysfunction, fibrotic diseases, insulin resistance, kidney failure, central nervous system disorders, auto-immune diseases and oncology.

In view of the number of pathological responses which are mediated by ROCK enzymes, there is a continuing need for inhibitors of such enzymes which can be useful in the treatment of many disorders. The present invention relates to novel compounds which are inhibitors of ROCK-I and ROCK-II isoforms of the Rho-associated coiled-coil forming protein kinase (ROCK) that have therapeutically desirable characteristics, particularly promising for some pulmonary diseases including asthma, chronic obstructive pulmonary disease (COPD), idiopathic pulmonary fibrosis (IPF) and pulmonary hypertension (PH) and specifically pulmonary arterial hypertension (PAH).

SUMMARY OF THE INVENTION

The present invention is directed to compounds of formula (I)

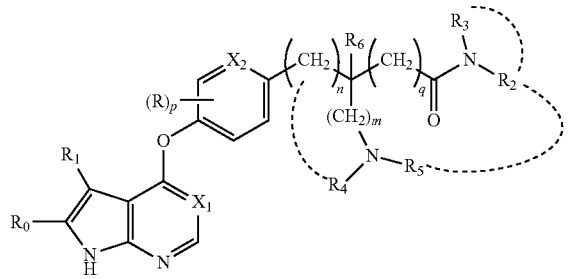

wherein $X_1$, $X_2$, R, $R_0$, $R_1$, $R_2$, $R_3$, $R_4$, $R_5$, $R_6$, p, m, n and q are as reported below in the detailed description of the invention, acting as ROCK inhibitors, to processes for the preparation thereof, pharmaceutical compositions comprising them either alone or in combination with one or more active ingredient, in admixture with one or more pharmaceutically acceptable carrier.

In one aspect, the invention provides the use of a compound of formula (I) for the manufacture of a medicament.

In a further aspect, the invention provides the use of a compound of formula (I) for the preparation of a medicament for the treatment of any disease characterized by ROCK enzyme aberrant activity and/or wherein an inhibition of activity is desirable and in particular through the selective inhibition of the ROCK enzyme isoforms over other Kinases.

Moreover the t invention provides a method for prevention and/or treatment of any disease wherein a ROCK enzyme inhibition is desirable, said method comprises administering to a patient in need of such treatment a therapeutically effective amount of a compound of formula (I).

In particular the compounds of the invention alone or combined with other active ingredients may be administered for the prevention and/or treatment of a pulmonary disease including asthma, chronic obstructive pulmonary disease (COPD), idiopathic pulmonary fibrosis (IPF) and pulmonary hypertension (PH) and specifically pulmonary arterial hypertension (PAH).

DETAILED DESCRIPTION OF THE INVENTION

The invention relates to compounds of formula (I)

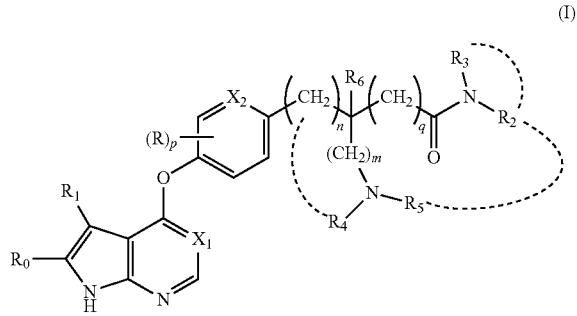

wherein
$X_1$, and $X_2$ are at each occurrence independently a CH group or a nitrogen atom;

p is zero or an integer from 1 to 3;

n, q and m are zero or an integer from 1 to 2;

each R, when present, is an halogen;

$R_0$ and $R_1$ are independently selected from the group consisting of

—H, halogen,

—$NR_7R_8$,

—CN, ($C_1$-$C_6$) alkyl, ($C_1$-$C_6$) haloalkyl, ($C_1$-$C_6$) hydroxyalkyl, ($C_1$-$C_6$) aminoalkyl, ($C_1$-$C_6$) alkoxy-($C_1$-$C_6$) alkyl ($C_3$-$C_{10}$) cycloalkyl, ($C_2$-$C_6$) alkenyl, ($C_5$-$C_7$) cycloalkenyl, ($C_2$-$C_6$) alkynyl, ($C_2$-$C_6$) hydroxyalkynyl, aryl, heteroaryl and ($C_3$-$C_6$) heterocycloalkyl each of which aryl, heteroaryl and ($C_3$-$C_6$) heterocycloalkyl being in its turn optionally and independently substituted with one or more groups selected from halogen,

—OH,

—CN,

—$NR_7R_8$,

—$CH_2NR_7R_8$, ($C_1$-$C_6$) alkyl, ($C_1$-$C_6$) haloalkyl, ($C_1$-$C_6$) hydroxyalkyl, ($C_2$-$C_6$) alkenyl, ($C_2$-$C_6$) alkynyl, ($C_2$-$C_6$) hydroxyalkynyl;

$R_2$ and $R_3$, the same or different, are selected from the group consisting of

—H, ($C_1$-$C_6$) alkyl, ($C_1$-$C_6$) haloalkyl, ($C_1$-$C_6$) hydroxyalkyl, ($C_1$-$C_6$) aminoalkyl, ($C_1$-$C_6$) alkoxy ($C_1$-$C_6$) alkyl, ($C_3$-$C_{10}$)cycloalkyl, ($C_3$-$C_8$)heterocycloalkyl, aryl, heteroaryl, aryl($C_1$-$C_6$)alkyl, aryl oxyl (C1-C6) alkyl, heteroaryl($C_1$-$C_6$)alkyl, ($C_3$-$C_8$)cycloalkyl($C_1$-$C_6$)alkyl, ($C_3$-$C_8$)heterocycloalkyl-($C_1$-$C_6$)alkyl each of said aryl, heteroaryl, cycloalkyl, heterocycloalkyl is further optionally substituted by one or more group selected independently from halogen, —CN, —OH, ($C_1$-$C_8$) alkyl, ($C_1$-$C_6$) haloalkyl, ($C_1$-$C_{10}$)alkoxy, aryl, aryl($C_1$-$C_6$) alkyl, carbamoyl, ($C_1$-$C_6$) aminoalkyl, ($C_1$-$C_6$) hydroxyalkyl; or, alternatively, $R_2$ and $R_3$, taken together with the nitrogen atom they are linked to, form a mono- or bi-cyclic saturated or partially saturated heterocyclic radical, preferably a 4 to 6 membered monocyclic radical, wherein at least one further ring carbon atom in the said heterocyclic radical is optionally replaced by at least one further group independently selected from N, NH, S or O and/or may bear an -oxo (=O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic, ring;

said heterocyclic radical being optionally in its turn further substituted with one or more groups selected from the group consisting of halogen, hydroxyl,

—$NR_7R_8$,

—$CH_2NR_7R_8$, ($C_1$-$C_6$) alkyl, ($C_1$-$C_6$) haloalkyl, ($C_1$-$C_6$) hydroxyalkyl, ($C_2$-$C_6$) alkenyl, ($C_2$-$C_6$) alkynyl, ($C_2$-$C_6$) hydroxyalkynyl, ($C_1$-$C_6$) alkoxy ($C_1$-$C_6$) alkyl, ($C_1$-$C_6$) alkanoyl, carbamoyl, ($C_3$-$C_6$) cycloalkyl-carbonyl, ($C_3$-$C_6$) heterocycloalkyl-carbonyl, aryl($C_1$-$C_6$)alkyl, aryl alkanoyl, arylsulfonyl, heteroaryl($C_1$-$C_6$)alkyl, heteroaryl-carbonyl, heteroaryloxyl, ($C_3$-$C_6$) cycloalkyl, ($C_3$-$C_8$)cycloalkyl($C_1$-$C_6$)alkyl, ($C_3$-$C_6$) heterocycloalkyl-($C_1$-$C_6$) alkyl, aryl and heteroaryl each of said cycloalkyl, aryl and heteroaryl being further optionally substituted by halogen, ($C_1$-$C_8$)alkyl, ($C_1$-$C_{10}$) alkoxy, ($C_1$-$C_6$)alkylthio, ($C_1$-$C_6$) aminoalkyl, ($C_1$-$C_6$) aminoalkoxyl, carbamoyl, ($C_1$-$C_6$)alkyl-sulfonyl;

$R_4$ and $R_5$ are at each occurrence independently selected in the group consisting of

H, ($C_1$-$C_6$) alkyl, ($C_1$-$C_6$) haloalkyl, ($C_1$-$C_6$) hydroxyalkyl, ($C_1$-$C_6$) aminoalkyl, ($C_1$-$C_6$) alkoxyl, ($C_1$-$C_6$) alkoxy-($C_1$-$C_6$) alkyl, ($C_3$-$C_6$) cycloalkyl-($C_1$-$C_6$) alkyl ($C_3$-$C_6$) heterocycloalkyl-($C_1$-$C_6$) alkyl, ($C_3$-$C_6$) cycloalkyl-carbonyl ($C_3$-$C_6$) heterocycloalkyl-carbonyl, aryl, heteroaryl and ($C_3$-$C_6$) heterocycloalkyl;

wherein any of said ($C_3$-$C_6$) cycloalkyl, aryl, heteroaryl and ($C_3$-$C_6$) heterocycloalkyl in its turn is optionally and independently substituted with one or more groups selected from halogen,

—OH, ($C_1$-$C_6$) alkyl;

—$NR_7R_8$;

or when $R_6$ is H, n is 1 and q is 0, $R_4$ can optionally be linked to the carbon atom of the methylene group —$(CH_2)_n$- via a divalent bridge —$CH_2$— when m is 1, or via a —$CH_2$—$CH_2$-bridge when m is 0, thus forming a pyrrolidine divalent group a1, or a2

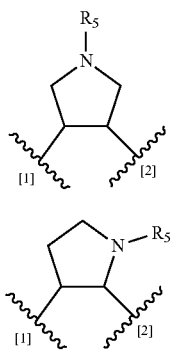

(a1)

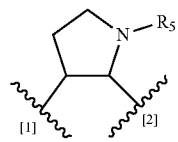

(a2)

[1] and [2] being respectively the point of attachment to the phenyl and carboxamide group; or when $R_6$ is H, $R_5$ can optionally be linked to the group $R_2$ to form a methylene —$CH_2$— bridge, thus forming a tetrahydropyrimidinone divalent group b1 when q is one and m and n are zero, or b2 when m and n are 1 and q is zero

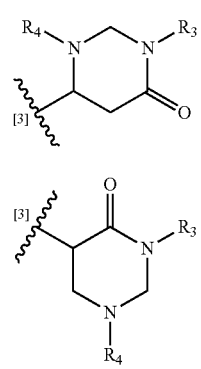

(b1)

(b2)

[3] being the point of attachment to the rest of molecule;

$R_6$ is selected from the group consisting of —H, $(C_1-C_6)$ alkyl, $(C_1-C_6)$ haloalkyl;

$R_7$ and $R_8$ are at each occurrence independently selected in the group

H,
$(C_1-C_6)$ alkyl,
$(C_1-C_6)$ haloalkyl,
$(C_1-C_6)$ hydroxyalkyl,
$(C_1-C_6)$ aminoalkyl,
$(C_1-C_6)$ alkoxyl,
$(C_1-C_6)$ alkoxy-$(C_1-C_6)$ alkyl,
$(C_3-C_6)$ heterocycloalkyl-$(C_1-C_6)$ alkyl,
aryl, heteroaryl and $(C_3-C_6)$ heterocycloalkyl;

wherein any of said aryl, heteroaryl and $(C_3-C_6)$ heterocycloalkyl in its turn is optionally and independently substituted with one or more groups selected from halogen,
—OH,
$(C_1-C_6)$ alkyl; or $R_7$ and $R_8$ are taken together with the nitrogen atom they are linked to, to form a 4 to 6 membered heterocyclic radical, wherein at least one further ring carbon atom in the said heterocyclic radical may be replaced by at least one group selected from N, S or O; said heterocyclic radical can be further optionally substituted by a group selected from H,
—CN,
halogen,
-oxo,
—$NR_7R_8$
$(C_1-C_6)$ alkyl,
$(C_1-C_6)$ haloalkyl,
$(C_1-C_6)$ hydroxyalkyl,
$(C_1-C_6)$ aminoalkyl,
$(C_1-C_6)$ alkoxyl,
$(C_1-C_6)$ alkoxy-$(C_1-C_6)$ alkyl,
alkanoyl;

or pharmaceutically acceptable salts and solvates thereof.

Definitions

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "halogen" or "halogen atoms" as used herein includes fluorine, chlorine, bromine, and iodine atom, preferably chlorine or fluorine.

The term "$(C_1-C_6)$ alkyl" refers to straight-chained or branched alkyl groups wherein the number of carbon atoms is in the range 1 to 6. Particular alkyl groups are methyl, ethyl, n-propyl, isopropyl and t-butyl.

The expressions "$(C_1-C_6)$ haloalkyl" refer to the above defined "$(C_1-C_6)$alkyl" groups wherein one or more hydrogen atoms are replaced by one or more halogen atoms, which can be the same or different.

Examples of said $(C_1-C_6)$ haloalkyl groups may thus include halogenated, poly-halogenated and fully halogenated alkyl groups wherein all of the hydrogen atoms are replaced by halogen atoms, e.g. trifluoromethyl or difluoro methyl groups.

By way of analogy, the terms "$(C_1-C_6)$ hydroxyalkyl" or "$(C_1-C_6)$ aminoalkyl" refer to the above defined "$(C_1-C_6)$ alkyl" groups wherein one or more hydrogen atoms are replaced by one or more hydroxy (OH) or amino group respectively. Examples include respectively hydroxymethyl, aminomethyl, dimethylaminopropyl and the like.

In the present description, unless otherwise provided, the definition of aminoalkyl encompasses alkyl groups (i.e. "$(C_1-C_6)$ alkyl" groups) substituted by one or more amino group ($NR_7R_8$). Thus, an example of aminoalkyl is a monoaminoalkyl group such as $R_7R_8N$—$(C_1-C_6)$ alkyl.

With reference to the substituent $R_7$ and $R_8$ as defined above and below, when $R_7$ and $R_8$ are taken together with the nitrogen atom they are linked to form a 4 to 6 membered heterocyclic radical, at least one further ring carbon atom in the said heterocyclic radical is optionally replaced by at least one heteroatom (e.g. N, S or O) and/or may bear -oxo (=O)

substituent groups. It is understood that the said heterocyclic radical might be further optionally substituted on any available position in the ring, namely on a carbon atom, or on any heteroatom available for substitution. Substitution on a carbon atom includes spiro disubstitution as well as substitution on two adjacent carbon atoms, in both cases thus form an additional 5 to 6 membered heterocyclic ring. Examples of said heterocycle radicals are 1-pyrrolidinyl, 1-piperidinyl, 1-piperazinyl, 4-morpholinyl, piperazin-4yl-2-one, 4-methylpiperazine-1-yl, 4-metylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, (3aR,6aS)-5-methyl-octahydropyrrolo[3,4-c]pyrrol-2-yl, 8-methyl-2,8-diazaspiro[4.5]decane-2-yl, 5-methyloctahydropyrrolo[3,4.5]decane-2-yl, 1,1-dioxidothiomorpholin-4yl.

The term "($C_3$-$C_{10}$) cycloalkyl" likewise "($C_3$-$C_6$) cycloalkyl" refers to saturated cyclic hydrocarbon groups containing the indicated number of ring carbon atoms. Examples include cyclopropyl, cyclobutyl, cyclopentyl, cyclohexyl, cycloheptyl, and polycyclic ring systems such as adamantan-yl.

The term "($C_2$-$C_6$) alkenyl" refers to straight or branched carbon chains with one or more double bonds, conjugated or not conjugated, in cis or trans configuration, wherein the number atoms is in the range 2 to 6.

By way of analogy, the terms "($C_5$-$C_7$) cycloalkenyl" refers to cyclic hydrocarbon groups containing from 5 to 7 ring carbon atoms and one or two double bonds.

The term "($C_2$-$C_6$) alkynyl" refers to straight or branched carbon chains with one or more triple bonds wherein the number atoms is in the range 2 to 6.

The term "($C_2$-$C_6$) hydroxyalkynyl" refers to the above defined "($C_1$-$C_6$) alkynyl" groups wherein one or more hydrogen atoms are replaced by one or more hydroxy (OH) group.

The term "($C_2$-$C_6$) aminoalkynyl" refers to the above defined "($C_1$-$C_6$) alkynyl" groups wherein one or more hydrogen atoms are replaced by one or more (—$NR_7R_8$) groups.

The expression "aryl" refers to mono, bi- or tri-cyclic carbon ring systems which have 6 to 20, preferably from 6 to 15 ring atoms, wherein at least one ring is aromatic. The expression "heteroaryl" refers to mono-, bi- or tri-cyclic ring systems with 5 to 20, preferably from 5 to 15 ring atoms, in which at least one ring is aromatic and in which at least one ring atom is a heteroatom (e.g. N, S or O).

Examples of suitable aryl or heteroaryl monocyclic ring systems include, for instance, phenyl, thienyl, pyrrolyl, pyrazolyl, imidazolyl, isoxazolyl, oxazolyl, isothiazolyl, thiazolyl, pyridinyl, pyrimidinyl, pyrazinyl, triazinyl, furanyl radicals and the like.

Examples of suitable aryl or heteroaryl bicyclic ring systems include naphthalenyl, biphenylenyl, purinyl, pteridinyl, pyrazolopyrimidinyl, benzotriazolyl, benzoimidazole-yl, quinolinyl, isoquinolinyl, indolyl, isoindolyl, benzothiopheneyl, benzodioxinyl, dihydrobenzodioxinyl, indenyl, dihydro-indenyl, dihydrobenzo[1,4]dioxinyl, benzothiazole-2-yl, dihydrobenzodioxepinyl, benzooxazinyl radicals and the like.

Examples of suitable aryl or heteroaryl tricyclic ring systems include fluorenyl radicals as well as benzocondensed derivatives of the aforementioned heteroaryl bicyclic ring systems.

In an analogous manner, the expressions "arylene" and "heteroarylene" refer to divalent groups, such a phenylene, biphenylene and thienylene. Such groups are also commonly named as "arenediyl" or "heteroarenediyl" groups. For example o-phenylene is also named benzene-1,2-diyl. Thienyl-ene is alternatively named thiophenediyl.

The expression "($C_3$-$C_6$) heterocycloalkyl" refers to saturated or partially unsaturated monocyclic ($C_3$-$C_6$) cycloalkyl groups in which at least one ring carbon atom is replaced by at least one heteroatom (e.g. N, S or O) or may bear an -oxo (=O) substituent group. Said heterocycloalkyl (i.e. heterocyclic radical or group) may be further optionally substituted on the available position in the ring, namely on a carbon atom, or on an heteroatom available for substitution. Substitution on a carbon atom includes spiro disubstitution as well as substitution on two adjacent carbon atoms, in both cases thus form additional condensed 5 to 6 membered heterocyclic ring. Examples of ($C_3$-$C_6$) heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydropyranyl, pyranyl, 2H- or 4H-pyranyl, dihydro- or tetrahydrofuranyl, dihydroisoxazolyl, pyrrolidin-2-one-yl, dihydropyrrolyl radicals and the like.

Specific examples of said heterocycle radicals are 1-pyrrolidinyl, 1-methyl-2-pyrrolidinyl, 1-piperidinyl, 1-piperazinyl, 4-morpholinyl, piperazin-4yl-2-one, 4-methylpiperazine-1-yl, 1-methylpiperidin-4yl, 4-metylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, and (3aR,6aS)-5-methyl-octahydropyrrolo[3,4-c]pyrrol-2-yl.

The term "aryl ($C_1$-$C_6$) alkyl" refers to an aryl ring linked to a straight-chained or branched alkyl groups wherein the number of carbon atoms is from 1 to 6, e.g. phenylmethyl (i.e. benzyl), phenylethyl or phenylpropyl.

Likewise the term "heteroaryl ($C_1$-$C_6$) alkyl" refers to an heteroaryl ring linked to a straight-chained or branched alkyl groups wherein the number of carbon atoms is from 1 to 6, e.g. furanylmethyl.

The term "alkanoyl", refers to HC(O)— or to alkylcarbonyl groups (e.g. ($C_1$-$C_6$)alkyC(O)— wherein the group "alkyl" has the meaning above defined. Examples include formyl, acetyl, propanoyl, butanoyl.

Likewise "($C_1$-$C_6$)alkyl-sulfonyl" refers to a "($C_1$-$C_6$) alkyl-S(O)$_2$ group wherein alkyl has the meaning above defined. An example is represented by methylsulfonyl.

The term "carbamoyl" refers to amino carbonyl derived groups —C(O)$NR_7R_8$, wherein $R_7$ and $R_8$ are as defined above in the definition of aminoalkyl groups and including substituted (preferred aminoalkyl substituted) and spiro substituted derivatives. Examples of such carbamoyl groups include aminocarbonyl, piperazine-1-carbonyl, morpholine-N-carbonyl, morpholine-N-carbonyl, N-(2-(dimethylamino) ethyl)aminocarbonyl, N-(2-(dimethylamino)ethyl)-N-methylaminocarbonyl, N-(3-(dimethylamino)propyl)-N-methylaminocarbonyl, 4-methylpiperazine-1-carbonyl, 4-(dimethylamino)piperidin-1-carbonyl, N-(2-(4-methylpiperazin-1-yl)ethyl)aminocarbonyl, (2-morpholino-ethyl) aminocarbonyl, N-methyl-N-(2 morpholino-ethyl) aminocarbonyl, N-(2-(piperidin-1-yl)ethyl)aminocarbonyl, N-methyl-N-(2-(piperidin-1-yl)ethyl)aminocarbonyl, N-(1-methylpiperidin-4-yl-methyl)aminocarbonyl, N-methyl-N-(1-methylpiperidin-4-yl)aminocarbonyl, N-methyl-N-(1-methylpiperidin-4-yl)aminocarbonyl, 5-methyloctahydropyrrolo[3,4-c]pyrrole-2 carbonyl.

The term "hydroxycarbonyl" refers to a terminal group HOC(O)—.

The term "($C_1$-$C_{10}$) alkoxy" or "($C_1$-$C_{10}$) alkoxyl", likewise "($C_1$-$C_6$) alkoxy" or "($C_1$-$C_6$) alkoxyl" etc., refers to a straight or branched hydrocarbon of the indicated number of carbons, attached to the rest of the molecule through an oxygen bridge. Likewise "$(C_1-C_6)$alkylthio" refers to the above hydrocarbon attached through a sulfur bridge.

The expression "$(C_1-C_6)$ haloalkoxy" or "$(C_1-C_6)$ haloalkoxyl" refers to the above defined haloalkyl, attached through an oxygen bridge, e.g. trifluoromethoxy.

By analogy, the expressions "$(C_3-C_6)$ heterocycloalkyloxyl" and "$(C_3-C_6)$ heterocycloalkyl $(C_1-C_6)$ alkoxyl" refer to heterocycloalkyl groups attached through an oxygen bridge and chained heterocycloalkyl-alkoxyl groups respectively. Examples of such $(C_3-C_6)$ heterocycloalkyloxyl and $(C_3-C_6)$ heterocycloalkyl $(C_1-C_6)$ alkoxyl groups are respectively (piperidin-4-yl)oxy, 1-methylpiperidin-4-yl)oxy, 2-(piperidin-4-yl)ethoxyl, 2-(1-methylpiperidin-4-yl) ethoxy, and 2-(4-morpholino)ethoxy.

The expressions "Aryloxyl" and "Aryl $(C_1-C_6)$ alkoxyl" likewise "heteroAryloxyl" and "Heteroaryl $(C_1-C_6)$ alkoxyl" refer to Aryl or Heteroaryl groups attached through an oxygen bridge and chained Aryl-alkoxyl or HeteroAryl-alkoxyl groups. Examples of such groups are phenyloxy, benzyloxy and pyridinyloxy respectively.

Likewise, the expressions "$(C_3-C_6)$ heterocycloalkyl-$(C_1-C_6)$ alkyl" and "$(C_3-C_6)$ cycloalkyl-$(C_1-C_6)$ alkyl" refer to the above defined heterocycloalkyl and cycloalkyl groups attached to the rest of the molecule via an alkyl group of the indicated number of carbons. Examples include piperidin-4-yl-methyl and cyclohexylethyl.

The expression "$(C_1-C_6)$ alkoxy-$(C_1-C_6)$ alkyl" refers to the above defined alkoxy group attached to the rest of the molecule via an alkyl group of the indicated number of carbons. Examples include methoxymethyl and methoxypropyl.

The expression "$(C_1-C_6)$ alkoxycarbonyl" refers to the above defined alkoxy group attached to the rest of the molecule via a carbonyl group, e.g. ethoxycarbonyl.

The expression like "$(C_1-C_6)$ alkoxycarbonyl-amino" refers to the above defined alkoxy group attached to the rest of the molecule via a carbonyl group followed by an amino group (—$NR_7$—), e.g. tert-butoxy-carbonyl-amino-.

"$(C_1-C_6)$ alkoxycarbonyl $(C_3-C_6)$ heterocycloalkyl $(C_1-C_6)$ alkyl" refers to alkoxy carbonyl heterocycloalkyl substituents enchained in the said order and attached to the rest of the molecule via an alkyl group of the indicated number of carbons, e.g. (tert-butyl piperidine-1-carboxylate)-4 yl-methyl.

The expression "$(C_1-C_6)$ aminoalkoxyl" refers to $(C_1-C_6)$ aminoalkyl groups as defined above attached through an oxygen bridge, e.g. (2-(dimethylamino)ethoxy.

The expression "$(C_1-C_6)$ hydroxyalkoxyl" refers to hydroxyalkyl groups as defined above attached to the rest of the molecule through an oxygen bridge, e.g. hydroxyethoxy.

The expression "$(C_1-C_6)$ aminoalkylcarbamoyl" refers to a "carbamoyl" group, as defined above, substituted with a $(C_1-C_6)$ aminoalkyl group (i.e. —C(O)$NR_7R_8$ wherein e.g. $R_8$ is an $(C_1-C_6)$ aminoalkyl), e.g. 2-(dimethylamino) ethyl carbamoyl.

The term "aryl oxyl $(C_1-C_6)$ alkyl" refers to an aryl-O— wherein aryl has the meaning above defined attached to the rest of the molecule via an alkyl group of the indicated number of carbons, e.g. phenoxyethyl.

The term "aryl alkanoyl" refers to an aryC(O) or arylalkylcarbonyl group [e.g. Aryl($C_1-C_6$)alkylC(O)—] wherein aryl and alkyl have the meaning above defined. Examples are represented by benzoyl, phenylacetyl, phenylpropanoyl or phenylbutanoyl radicals. Likewise "aryl sulfonyl" refers to an aryS(O)$_2$ group wherein aryl has the meaning above defined, e.g. phenylsulfonyl.

Likewise, enchained substituents derive their definition from the composing fragments, like in the above reported definitions, such as "$(C_3-C_6)$ cycloalkyl-carbonyl", "$(C_3-C_6)$ heterocycloalkyl-carbonyl", "heteroaryl-carbonyl"; referring to the above defined fragments attached to the rest of the molecule via a carbonyl group. Examples of such groups include cyclopropanecarbonyl, pyrrolidine-3-carbonyl, (pyridin-3-yl)carbonyl.

The expression "saturated, partially unsaturated or aromatic, five or six membered cycloalkane-diyl, arylene-diyl or heterocycle-diyl" refers to suitable disubstituted cycloalkane or heterocycle or aromatic residue with five or six elements including 1,2-, 1,3- or 1,4-benzene-diyl; 2,3-, 3,4-, 4,5- or 5,6-pyridine-diyl; 3,4-, 4,5- or 5,6-pyridazine-diyl; 4,5- or 5,6-pyrimidine-diyl; 2,3-pyrazinediyl; 2,3-, 3,4- or 4,5-thiophene-diyl/furane-diyl/pyrrole-diyl; 4,5-imidazole-diyl/oxazole-diyl/thiazolediyl; 3,4- or 4,5-pyrazole-diyl/isoxazolediyl/isothiazole-diyl their saturated or partially unsaturated analogues and the like. Other non vicinal disubstituted residues (diradical) are included too, such as 4,6-pyrimidine-diyl, and the like.

The expression "ring system" refers to mono- or bicyclic or polycyclic ring systems which may be saturated, partially unsaturated or unsaturated, such as aryl, $(C_3-C_{10})$ cycloalkyl, $(C_3-C_6)$heterocycloalkyl or heteroaryl.

The terms "group", "radical" or "fragment" or "substituent" are synonymous and are intended to indicate functional groups or fragments of molecules attachable to a bond or other fragments or molecules. Thus, as an example, a "heterocyclic radical" herein refers to a mono- or bi-cyclic saturated or partially saturated heterocyclic moiety (group, radical), preferably a 4 to 11 membered monocyclic radical, at least one further ring carbon atom in the said heterocyclic radical is optionally replaced by at least one further heteroatom independently selected from N, S or O and/or may bear an -oxo (=O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic ring. Examples of said heterocycle radicals are 1-pyrrolidinyl, 1-piperidinyl, 1-piperazinyl, 4-morpholinyl, piperazin-4-yl-2-one, 4-methylpiperazine-1-yl, 4-metylpiperazine-1-yl-2-one, 7-methyl-2,7-diazaspiro-[3.5]nonan-2-yl, 2-methyl-2,9-diazaspiro[5.5]undecan-9-yl, 9-methyl-3,9-diazaspiro[5.5]-undecan-3-yl, and (3aR,6aS)-5-methyl-octahydropyrrolo[3,4-c]pyrrol-2-yl and the like.

A dash ("-") that is not between two letters or symbols is meant to represent the point of attachment for a substituent. When graphically represented the point of attachment in a cyclic functional group is indicated with a dot ("•") localized in one of the available ring atom where the functional group is attachable to a bond or other fragment of molecules.

An oxo moiety is represented by (O) as an alternative to the other common representation, e.g. (=O). Thus, in terms of general formula, the carbonyl group is herein preferably represented as —C(O)— as an alternative to the other common representations such as —CO—, —(CO)— or —C(=O)—. In general, the bracketed group is a lateral group, not included into the chain, and brackets are used, when deemed useful, to help disambiguating linear chemical formulas; e.g. the sulfonyl group —$SO_2$— might be also represented as —$S(O)_2$— to disambiguate e.g. with respect to the sulfinic group —S(O)O—.

When a numerical index is used like in the statement "p is zero or an integer from 1 to 3" the statement (value) "p is zero" means that the substituent R is absent, that is to say there is no substituent R on the ring.

Whenever basic amino or quaternary ammonium groups are present in the compounds of formula I, physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups such as COOH groups, corresponding physiological cation salts may be present as well, for instance including alkaline or alkaline earth metal ions.

It will be apparent that compounds of formula (I) when contain one or more stereogenic center, may exist as optical stereoisomers.

Where the compounds according to the invention have at least one stereogenic center, they may accordingly exist as enantiomers. Where the compounds according to the invention possess two or more stereogenic centers, they may additionally exist as diastereoisomers. All such single enantiomers, diastereoisomers and mixtures thereof in any proportion are encompassed within the scope of the present invention. The absolute configuration (R) or (S) for carbon bearing a stereogenic center is assigned on the basis of Cahn-Ingold-Prelog nomenclature rules based on groups' priorities.

The invention further concerns the corresponding deuterated derivatives of compounds of formula (I).

All preferred groups or embodiments described above and herebelow for compounds of formula I may be combined among each other and apply as well mutatis mutandis.

In a preferred embodiment, the invention is directed to compounds of formula (I) as defined above wherein each of $X_1$ and $X_2$ is a CH; represented by the formula Ia:

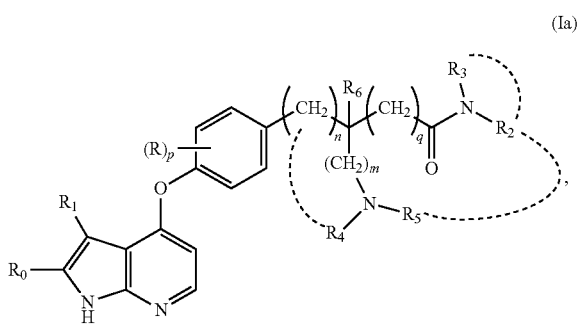

(Ia)

In a second preferred embodiment, the invention is directed to compounds of formula (I) as defined above:

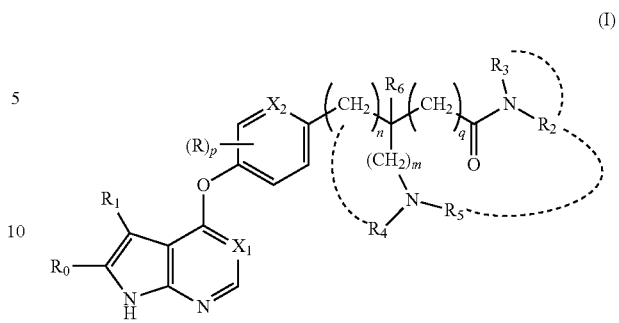

(I)

wherein $X_1$, and $X_2$ are both a CH group;

p is zero or 1;

n, q and m are zero or an integer from 1 to 2;

each R, when present, is halogen;

$R_0$ and $R_1$ are independently selected from the group consisting of

—H,

—CN, ($C_1$-$C_6$) alkyl;

$R_2$ and $R_3$, the same or different, are selected from the group consisting of

—H, ($C_1$-$C_6$) alkyl, ($C_1$-$C_6$) aminoalkyl, ($C_1$-$C_6$) alkoxy ($C_1$-$C_6$) alky, ($C_3$-$C_{10}$)cycloalkyl, ($C_3$-$C_8$)heterocycloalkyl, Aryl, each of said aryl, cycloalkyl, heterocycloalkyl is further optionally substituted by one or more group selected independently from ($C_1$-$C_8$) alkyl, and ($C_1$-$C_6$) haloalkyl, or $R_2$ and $R_3$, in the alternative, taken together with the nitrogen atom they are linked to, form a mono- or bi-cyclic saturated, at least one further ring carbon atom in the said heterocyclic radical is optionally replaced by at least one further group selected from N and NH;

said heterocyclic radical being optionally in its turn further substituted with one or more groups selected from the group consisting of ($C_1$-$C_6$) alkyl, aryl($C_1$-$C_6$)alkyl, heteroaryl($C_1$-$C_6$)alkyl, ($C_3$-$C_6$) cycloalkyl, $R_4$ and $R_5$ are at each occurrence independently selected in the group consisting of

H, ($C_1$-$C_6$) alkyl, $R_6$ is —H;

$R_7$ and $R_8$ are H.

In a third preferred embodiment, the invention is directed to compounds of formula (I) as defined above:

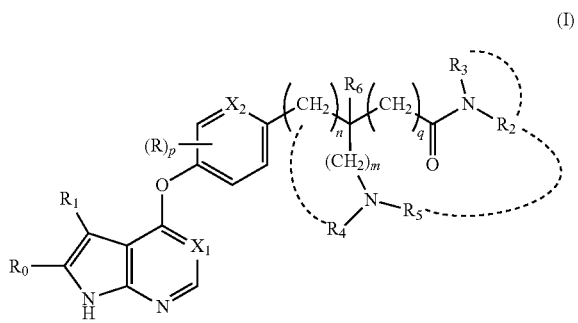

(I)

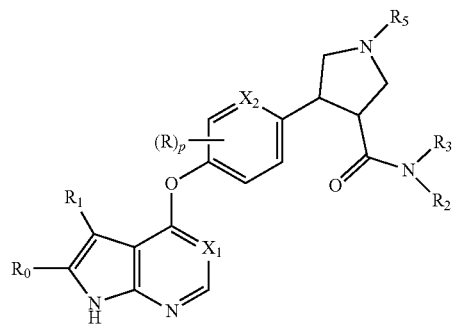

(Ib)

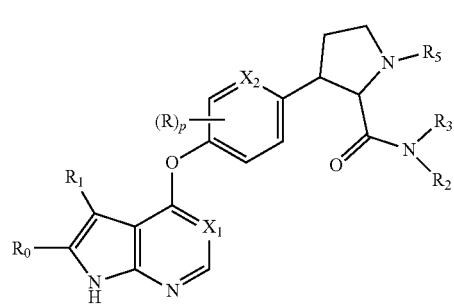

(Ic)

wherein $X_1$, and $X_2$ are both a CH group;

p is zero or 1;

n, q and m are zero or an integer from 1 to 2;

each R, when present, is fluorine;

$R_0$ and $R_1$ are independently selected from the group consisting of

—H,

—CN, ($C_1$-$C_6$) alkyl, which is methyl, $R_2$ and $R_3$, the same or different, are selected from the group consisting of

—H, ($C_1$-$C_6$) alkyl which is methyl, ($C_1$-$C_6$) aminoalkyl which is dimethylaminopropyl, ($C_1$-$C_6$) alkoxy ($C_1$-$C_6$) alkyl which is methoxypropyl, ($C_3$-$C_{10}$)cycloalkyl which is cyclohexyl, ($C_3$-$C_8$)heterocycloalkyl which is piperidinyl, tetrahydropyranyl, aryl which is phenyl, each of said aryl, cycloalkyl, heterocycloalkyl is further optionally substituted by one or more group selected independently from methyl and trifluoromethyl, or $R_2$ and $R_3$, in the alternative, taken together with the nitrogen atom they are linked to, form a mono- or bi-cyclic saturated, at least one further ring carbon atom in the said heterocyclic radical is optionally replaced by at least one further heteroatom which is N, said heterocyclic radical being optionally in its turn further substituted with one or more groups selected from the group consisting of ($C_1$-$C_6$) alkyl which is methyl, aryl($C_1$-$C_6$)alkyl which is phenylmethyl, heteroaryl($C_1$-$C_6$)alkyl which is (pyridinyl)methyl, ($C_3$-$C_6$) cycloalkyl which is cyclopropyl;

$R_4$ and $R_5$ are at each occurrence independently selected in the group consisting of

H, ($C_1$-$C_6$) alkyl which is methyl, $R_6$ is —H, $R_7$ and $R_8$ are H.

In a further preferred embodiment, the invention is directed to compounds of formula (I) as defined above, wherein, when $R_6$ is H, n is 1 and q is 0, $R_4$ links to the carbon atom of the methylene group via a divalent bridge —$CH_2$— when m is 1, or via a —$CH_2$—$CH_2$— when m is 0, forming a pyrrolidine divalent group, represented by formulae (Ib) and (Ic):

wherein $X_1$, and $X_2$ are both a CH group;

p is zero;

$R_0$ and $R_1$ are independently selected from the group consisting of

—H, ($C_1$-$C_6$) alkyl, $R_2$ and $R_3$, the same or different, are selected from the group consisting of

—H, ($C_1$-$C_6$) alkyl, ($C_1$-$C_6$) aminoalkyl ($C_1$-$C_6$) alkoxy ($C_1$-$C_6$) alkyl, ($C_3$-$C_8$)heterocycloalkyl, aryl($C_1$-$C_6$)alkyl, aryl oxyl (C1-C6) alkyl, heteroaryl($C_1$-$C_6$)alkyl, each of said heterocycloalkyl is further optionally substituted by one or more ($C_1$-$C_8$) alkyl group, or $R_2$ and $R_3$, in the alternative, taken together with the nitrogen atom they are linked to, form a mono-cyclic saturated ring, wherein at least one further ring carbon atom in the said heterocyclic radical is optionally replaced by at least one further group selected from N and NH, $R_5$ is selected in the group consisting of

H, ($C_1$-$C_6$) alkyl.

In a further preferred embodiment, the invention is directed to compounds of formula (I) as defined above, wherein, when $R_6$ is H, n is 1 and q is 0, $R_4$ links to the carbon atom of the methylene group via a divalent bridge —$CH_2$— when m is 1, or via a —$CH_2$—$CH_2$— when m is 0, forming a pyrrolidine divalent group, represented by the formula (Ib) and (Ic):

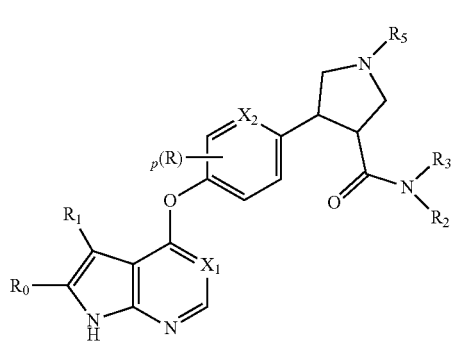

(Ib)

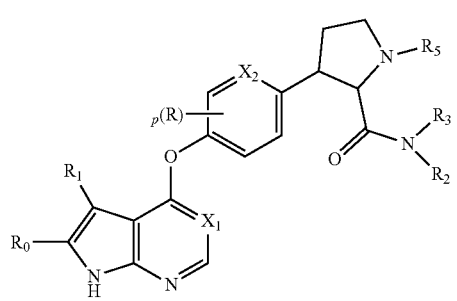

(Ic)

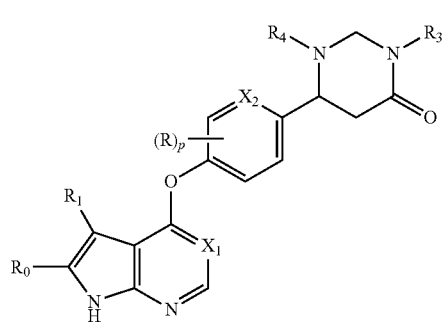

(Id)

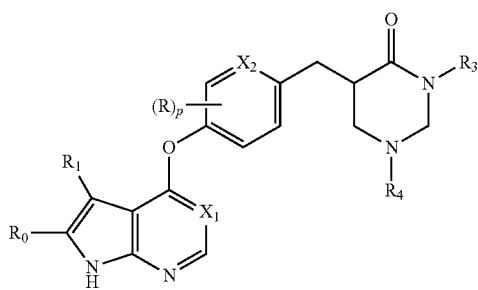

(Ie)

wherein $X_1$, and $X_2$ are both a CH group;

p is zero;

$R_0$ and $R_1$ are independently selected from the group consisting of

—H, $(C_1-C_6)$ alkyl which is methyl, $R_2$ and $R_3$, the same or different, are selected from the group consisting of

—H, $(C_1-C_6)$ alkyl which is methyl, $(C_1-C_6)$ aminoalkyl which is dimethylaminopropyl, $(C_1-C_6)$ alkoxy $(C_1-C_6)$ alkyl which is methoxypropyl, $(C_3-C_8)$heterocycloalkyl which is piperidinyl, tetrahydropyranyl, aryl$(C_1-C_6)$alkyl which is phenylmethyl, phenylethyl, aryl oxyl (C1-C6) alkyl which is phenoxyethyl, heteroaryl$(C_1-C_6)$alkyl which is (pyridinyl)ethyl, each of said heterocycloalkyl is further optionally substituted by one or more methyl group, or $R_2$ and $R_3$, in the alternative, taken together with the nitrogen atom they are linked to, form a mono-cyclic saturated, wherein at least one further ring carbon atom in the said heterocyclic radical is optionally replaced by NH, $R_5$ is selected in the group consisting of

H;

methyl.

In a further preferred embodiment, the invention is directed to compounds of formula (I) as defined above, wherein, when $R_6$ is H, $R_5$ links to the group $R_2$ to form a methylene —CH$_2$— bridge, thus forming a tetrahydropyrimidinone divalent group, represented by the formula (Id) when q is 1, m and n are zero, and (Ie) when m and n are 1 and q is zero:

wherein $X_1$, and $X_2$ are both a CH group;

p is zero or 1;

each R, when present, is halogen;

$R_0$ and $R_1$ are independently selected from the group consisting of

—H,

—CN, $(C_1-C_6)$ alkyl, $R_3$, is selected from the group consisting of $(C_1-C_6)$ aminoalkyl, $(C_1-C_6)$ alkoxy $(C_1-C_6)$ alkyl, $(C_3-C_8)$heterocycloalkyl, heteroaryl$(C_1-C_6)$alkyl, each of said heterocycloalkyl is further optionally substituted by one or more $(C_1-C_8)$ alkyl group;

$R_4$ is selected in group consisting of

H, $(C_1-C_6)$ alkyl.

In a further preferred embodiment, the invention is directed to compounds of formula (I) as defined above, wherein, when $R_6$ is H, $R_5$ links to the group $R_2$ to form a methylene —CH$_2$— bridge, forming a tetrahydropyrimidinone divalent group, represented by the formula (Id) when q is 1, m and n are zero, and (Ie) when m and n are 1 and q is zero:

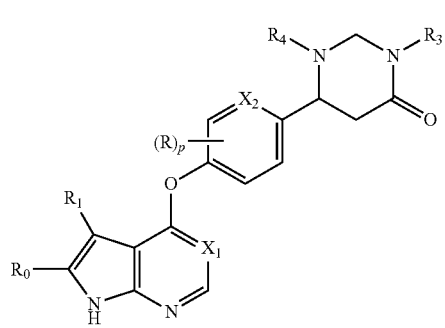

(Id)

-continued

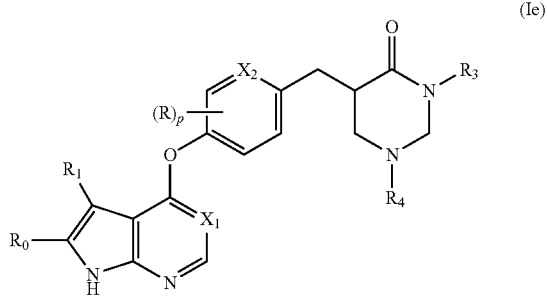

(Ie)

wherein
$X_1$, and $X_2$ are both a CH group;
p is zero or 1;
each R, when present, is fluorine;
$R_0$ and $R_1$ are independently selected from the group consisting of
—H,
—CN,
$(C_1-C_6)$ alkyl which is methyl,
$R_3$, is selected from the group consisting of
$(C_1-C_6)$ aminoalkyl which is dimethylaminopropyl,
$(C_1-C_6)$ alkoxy $(C_1-C_6)$ alkyl which is methoxypropyl,
$(C_3-C_8)$heterocycloalkyl which is piperidinyl,
heteroaryl$(C_1-C_6)$alkyl which is (pyridinyl)ethyl,
each of said heterocycloalkyl is further optionally substituted by one or more methyl group;
$R_4$ is H.

The present invention also provides a pharmaceutical composition comprising a compound of formula I, or a pharmaceutically acceptable salt thereof in admixture with one or more pharmaceutically acceptable carrier or excipient, either alone or in combination with one or more further active ingredient.

In one aspect, the invention provides a compound according to the invention for use as a medicament.

In a further aspect, the invention provides the use of a compound of the invention, or a pharmaceutically acceptable salt thereof, in the manufacture of a medicament for the treatment of disorders associated with ROCK enzymes mechanisms, particularly for the treatment of disorders such as pulmonary diseases.

In particular, the invention provides compounds of formula (I) for use in the prevention and/or treatment of pulmonary disease selected from the group consisting of asthma, chronic obstructive pulmonary disease COPD, idiopathic pulmonary fibrosis (IPF), pulmonary hypertension (PH) and specifically Pulmonary Arterial Hypertension (PAH).

The invention also provides a method for the prevention and/or treatment of disorders associated with ROCK enzymes mechanisms, said method comprising administering to a patient in need of such treatment a therapeutically effective amount of a compound of the invention.

In particular the invention provides methods for the prevention and/or treatment wherein the disorder is asthma, chronic obstructive pulmonary disease COPD idiopathic pulmonary fibrosis (IPF), Pulmonary hypertension (PH) and specifically Pulmonary Arterial Hypertension (PAH).

According to specific embodiments, the invention provides the compounds listed in the table below and pharmaceutical acceptable salts thereof.

| Ex. N. | Chemical Name |
|---|---|
| 1 | 3-amino-2-(4-((3-methyl-1H-pyrrolo[2,3-b]pyridin-4-yl)oxy)benzyl)-1-(4-methylpiperazin-1-yl)propan-1-one |
| 2 | 3-amino-1-(4-cyclopropylpiperazin-1-yl)-2-(4-((3-methyl-1H-pyrrolo[2,3-b]pyridin-4-yl)oxy)benzyl)propan-1-one |
| 3 | 3-amino-2-(3-fluoro-4-((3-methyl-1H-pyrrolo[2,3-b]pyridin-4-yl)oxy)benzyl)-N-(1-methylpiperidin-4-yl)propanamide |
| 4 | 3-amino-2-(3-fluoro-4-((3-methyl-1H-pyrrolo[2,3-b]pyridin-4-yl)oxy)benzyl)-1-((1S,4S)-5-methyl-2,5-diazabicyclo[2.2.1]heptan-2-yl)propan-1-one |
| 5 | 3-amino-2-(3-fluoro-4-((3-methyl-1H-pyrrolo[2,3-b]pyridin-4-yl)oxy)benzyl)-1-(4-(pyridin-2-ylmethyl)piperazin-1-yl)propan-1-one |
| 6 | 3-amino-1-(4-benzylpiperazin-1-yl)-2-(4-((2-methyl-1H-pyrrolo[2,3-b]pyridin-4-yl)oxy)benzyl)propan-1-one |
| 7 | 3-amino-1-(4-benzylpiperazin-1-yl)-3-(4-((3-methyl-1H-pyrrolo[2,3-b]pyridin-4-yl)oxy)phenyl)propan-1-one |
| 8 | 2-(4-((1H-pyrrolo[2,3-b]pyridin-4-yl)oxy)phenyl)-2-amino-N-cyclohexylacetamide |
| 9 | 2-(4-((1H-pyrrolo[2,3-b]pyridin-4-yl)oxy)phenyl)-2-amino-N-phenylacetamide |
| 10 | 2-(4-((1H-pyrrolo[2,3-b]pyridin-4-yl)oxy)phenyl)-2-amino-N-(4-(trifluoromethyl)phenyl)acetamide |
| 11 | 2-(4-((1H-pyrrolo[2,3-b]pyridin-4-yl)oxy)phenyl)-2-amino-1-(4-methylpiperazin-1-yl)ethanone |
| 12 | 2-(4-((1H-pyrrolo[2,3-b]pyridin-4-yl)oxy)phenyl)-2-amino-N,N-dimethylacetamide |
| 13 | 2-(4-((1H-pyrrolo[2,3-b]pyridin-4-yl)oxy)phenyl)-2-amino-N-(tetrahydro-2H-pyran-4-yl)acetamide |
| 14 | 2-(4-((1H-pyrrolo[2,3-b]pyridin-4-yl)oxy)phenyl)-2-amino-N-(1-methylpiperidin-4-yl)acetamide |
| 15 | 4-amino-1-(4-benzylpiperazin-1-yl)-3-(4-((3-methyl-1H-pyrrolo[2,3-b]pyridin-4-yl)oxy)phenyl)butan-1-one |
| 16 | 4-amino-1-(4-cyclopropylpiperazin-1-yl)-3-(4-((3-methyl-1H-pyrrolo[2,3-b]pyridin-4-yl)oxy)phenyl)butan-1-one |
| 17 | rac-(3R,4S)-N-benzyl-4-(4-((3-methyl-1H-pyrrolo[2,3-b]pyridin-4-yl)oxy)phenyl)pyrrolidine-3-carboxamide |
| 18 | rac-(3R,4S)-N-benzyl-N-methyl-4-(4-((3-methyl-1H-pyrrolo[2,3-b]pyridin-4-yl)oxy)phenyl)pyrrolidine-3-carboxamide |
| 19 | rac-(2S,3R)-N-benzyl-3-(4-((3-methyl-1H-pyrrolo[2,3-b]pyridin-4-yl)oxy)phenyl)pyrrolidine-2-carboxamide |
| 20 | rac-(2S,3R)-3-(4-((3-methyl-1H-pyrrolo[2,3-b]pyridin-4-yl)oxy)phenyl)-N-(2-(pyridin-4-yl)ethyl)pyrrolidine-2-carboxamide |
| 21 | rac-(2S,3R)-N-(3-methoxypropyl)-3-(4-((3-methyl-1H-pyrrolo[2,3-b]pyridin-4-yl)oxy)phenyl)pyrrolidine-2-carboxamide |
| 22 | rac-(2S,3R)-3-(4-((3-methyl-1H-pyrrolo[2,3-b]pyridin-4-yl)oxy)phenyl)-N-phenethylpyrrolidine-2-carboxamide |
| 23 | rac-(2S,3R)-3-(4-((3-methyl-1H-pyrrolo[2,3-b]pyridin-4-yl)oxy)phenyl)-N-(2-phenoxyethyl)pyrrolidine-2-carboxamide |
| 24 | rac-(2S,3R)-3-(4-((3-methyl-1H-pyrrolo[2,3-b]pyridin-4-yl)oxy)phenyl)-N-(tetrahydro-2H-pyran-4-yl)pyrrolidine-2-carboxamide |
| 25 | rac-(2S,3R)-3-(4-((3-methyl-1H-pyrrolo[2,3-b]pyridin-4-yl)oxy)phenyl)-N-(1-methylpiperidin-4-yl)pyrrolidine-2-carboxamide |
| 26 | rac-(2R,3S)-N-(3-(dimethylamino)propyl)-3-(4-((3-methyl-1H-pyrrolo[2,3-b]pyridin-4-yl)oxy)phenyl)pyrrolidine-2-carboxamide |
| 27 | rac-((2S,3R)-3-(4-((3-methyl-1H-pyrrolo[2,3-b]pyridin-4-yl)oxy)phenyl)pyrrolidin-2-yl)(piperazin-1-yl)methanone |
| 28 | 3-amino-N-cyclohexyl-2-(3-fluoro-4-((3-methyl-1H-pyrrolo[2,3-b]pyridin-4-yl)oxy)benzyl)propanamide |

| Ex. N. | Chemical Name |
|---|---|
| 29 | 3-amino-1-(4-benzylpiperazin-1-yl)-2-(3-fluoro-4-((3-methyl-1H-pyrrolo[2,3-b]pyridin-4-yl)oxy)benzyl)propan-1-one |
| 30 | 3-amino-1-(4-benzylpiperazin-1-yl)-2-(4-((3-methyl-1H-pyrrolo[2,3-b]pyridin-4-yl)oxy)benzyl)propan-1-one |
| 31 | 3-amino-N-cyclohexyl-2-(4-((3-methyl-1H-pyrrolo[2,3-b]pyridin-4-yl)oxy)benzyl)propanamide |
| 32 | 2-(4-((1H-pyrrolo[2,3-b]pyridin-4-yl)oxy)benzyl)-3-amino-1-(4-benzylpiperazin-1-yl)propan-1-one |
| 33 | 2-(4-((1H-pyrrolo[2,3-b]pyridin-4-yl)oxy)benzyl)-3-amino-N-cyclohexylpropanamide |
| 34 | 2-(4-((1H-pyrrolo[2,3-b]pyridin-4-yl)oxy)benzyl)-3-amino-N-(tetrahydro-2H-pyran-4-yl)propanamide |
| 35 | 2-(4-((1H-pyrrolo[2,3-b]pyridin-4-yl)oxy)benzyl)-3-amino-N-(3-methoxypropyl)propanamide |
| 36 | 1-(4-benzylpiperazin-1-yl)-2-(4-((3-methyl-1H-pyrrolo[2,3-b]pyridin-4-yl)oxy)benzyl)-3-(methylamino)propan-1-one |
| 37 | 1-(4-benzylpiperazin-1-yl)-3-(dimethylamino)-2-(4-((3-methyl-1H-pyrrolo[2,3-b]pyridin-4-yl)oxy)benzyl)propan-1-one |
| 38 | 3-(3-(dimethylamino)propyl)-6-(4-((3-methyl-1H-pyrrolo[2,3-b]pyridin-4-yl)oxy)phenyl)tetrahydropyrimidin-4(1H)-one |
| 39 | 3-(3-methoxypropyl)-6-(4-((3-methyl-1H-pyrrolo[2,3-b]pyridin-4-yl)oxy)phenyl)tetrahydropyrimidin-4(1H)-one |
| 40 | 6-(4-((3-methyl-1H-pyrrolo[2,3-b]pyridin-4-yl)oxy)phenyl)-3-(2-(pyridin-4-yl)ethyl)tetrahydropyrimidin-4(1H)-one |
| 41 | 3-(3-(dimethylamino)propyl)-5-(3-fluoro-4-((3-methyl-1H-pyrrolo[2,3-b]pyridin-4-yl)oxy)benzyl)tetrahydropyrimidin-4(1H)-one |
| 42 | 5-(3-fluoro-4-((3-methyl-1H-pyrrolo[2,3-b]pyridin-4-yl)oxy)benzyl)-3-(3-methoxypropyl)tetrahydropyrimidin-4(1H)-one |
| 43 | 5-(3-fluoro-4-((3-methyl-1H-pyrrolo[2,3-b]pyridin-4-yl)oxy)benzyl)-3-(2-(pyridin-4-yl)ethyl)tetrahydropyrimidin-4(1H)-one |
| 44 | 3-amino-2-(4-((3-cyano-1H-pyrrolo[2,3-b]pyridin-4-yl)oxy)benzyl)-N-(3-(dimethylamino)propyl)propanamide |
| 45 | 4-(4-((1-(3-(dimethylamino)propyl)-6-oxohexahydropyrimidin-5-yl)methyl)phenoxy)-1H-pyrrolo[2,3-b]pyridine-3-carbonitrile |
| 46 | 3-amino-2-(4-((3-cyano-1H-pyrrolo[2,3-b]pyridin-4-yl)oxy)benzyl)-N-(1-methylpiperidin-4-yl)propanamide |
| 47 | 4-(4-((1-(1-methylpiperidin-4-yl)-6-oxohexahydropyrimidin-5-yl)methyl)phenoxy)-1H-pyrrolo[2,3-b]pyridine-3-carbonitrile |
| 48 | 4-(4-(2-(aminomethyl)-3-((1S,4S)-5-methyl-2,5-diazabicyclo[2.2.1]heptan-2-yl)-3-oxopropyl)phenoxy)-1H-pyrrolo[2,3-b]pyridine-3-carbonitrile |
| 49 | 4-(4-(2-(aminomethyl)-3-oxo-3-(4-(pyridin-2-ylmethyl)piperazin-1-yl)propyl)phenoxy)-1H-pyrrolo[2,3-b]pyridine-3-carbonitrile |
| 50 | rac-(3R,4S)-N-benzyl-1-methyl-4-(4-((3-methyl-1H-pyrrolo[2,3-b]pyridin-4-yl)oxy)phenyl)pyrrolidine-3-carboxamide |
| 4A | (1st eluting) 3-amino-2-(3-fluoro-4-((3-methyl-1H-pyrrolo[2,3-b]pyridin-4-yl)oxy)benzyl)-1-((1S,4S)-5-methyl-2,5-diazabicyclo[2.2.1]heptan-2-yl)propan-1-one |
| 4B | (2nd eluting) 3-amino-2-(3-fluoro-4-((3-methyl-1H-pyrrolo[2,3-b]pyridin-4-yl)oxy)benzyl)-1-((1S,4S)-5-methyl-2,5-diazabicyclo[2.2.1]heptan-2-yl)propan-1-one |
| 5A | (1st eluting) 3-amino-2-(3-fluoro-4-((3-methyl-1H-pyrrolo[2,3-b]pyridin-4-yl)oxy)benzyl)-1-(4-(pyridin-2-ylmethyl)piperazin-1-yl)propan-1-one |
| 5B | (2nd eluting) 3-amino-2-(3-fluoro-4-((3-methyl-1H-pyrrolo[2,3-b]pyridin-4-yl)oxy)benzyl)-1-(4-(pyridin-2-ylmethyl)piperazin-1-yl)propan-1-one |
| 7A | (1st eluting) 3-amino-1-(4-benzylpiperazin-1-yl)-3-(4-((3-methyl-1H-pyrrolo[2,3-b]pyridin-4-yl)oxy)phenyl)propan-1-one |
| 7B | (2nd eluting) 3-amino-1-(4-benzylpiperazin-1-yl)-3-(4-((3-methyl-1H-pyrrolo[2,3-b]pyridin-4-yl)oxy)phenyl)propan-1-one |
| 29A | (1st eluting) 3-amino-1-(4-benzylpiperazin-1-yl)-2-(3-fluoro-4-((3-methyl-1H-pyrrolo[2,3-b]pyridin-4-yl)oxy)benzyl)propan-1-one |
| 29B | (2nd eluting) 3-amino-1-(4-benzylpiperazin-1-yl)-2-(3-fluoro-4-((3-methyl-1H-pyrrolo[2,3-b]pyridin-4-yl)oxy)benzyl)propan-1-one |
| 32A | (1st eluting) 2-(4-((1H-pyrrolo[2,3-b]pyridin-4-yl)oxy)benzyl)-3-amino-1-(4-benzylpiperazin-1-yl)propan-1-one |
| 32B | (2nd eluting) 2-(4-((1H-pyrrolo[2,3-b]pyridin-4-yl)oxy)benzyl)-3-amino-1-(4-benzylpiperazin-1-yl)propan-1-one |
| 17A | (1st eluting) (3R,4S)-N-benzyl-4-(4-((3-methyl-1H-pyrrolo[2,3-b]pyridin-4-yl)oxy)phenyl)pyrrolidine-3-carboxamide |
| 17B | (2nd eluting) (3R,4S)-N-benzyl-4-(4-((3-methyl-1H-pyrrolo[2,3-b]pyridin-4-yl)oxy)phenyl)pyrrolidine-3-carboxamide |

The compounds of the invention, including all the compounds hereabove listed, can be prepared from readily available starting materials using the following general methods and procedures or by using slightly modified processes readily available to those of ordinary skill in the art. Although a particular embodiment of the present invention may be shown or described herein, those skilled in the art will recognize that all embodiments or aspects of the present invention can be obtained using the methods described herein or by using other known methods, reagents and starting materials. When typical or preferred process conditions (i.e. reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by those skilled in the art by routine optimization procedures.

Thus, processes described below and reported in the following schemes should not be viewed as limiting the scope of the synthetic methods available for the preparation of the compounds of the invention.

In some cases, generally known protective groups (PG) could be employed when needed to mask or protect sensitive or reactive moieties, in accordance to general principles of chemistry (Protective group in organic syntheses, 3rd ed. T. W. Greene, P. G. M. Wuts).

The compounds of formula I, including all the compounds here above listed, can be generally prepared according to the procedures shown in the schemes below. Where a specific synthetic step differs from what is described in the general schemes, it has been detailed in the specific examples, and/or in additional schemes.

Compounds of formula I contain at least one stereogenic centre, as marked by an asterisk * in the picture below.

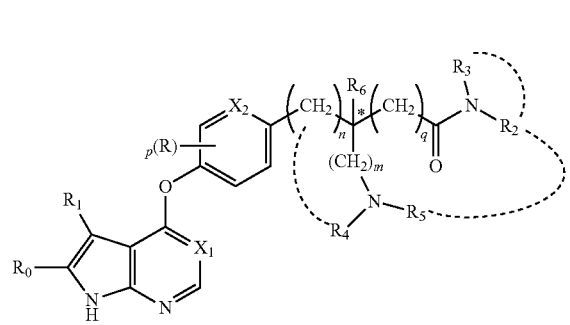

In a preferred embodiment, the invention is directed to compounds of formula I as defined above, wherein, when $R_6$ is H, n is 1 and q is 0, $R_4$ links the nitrogen atom to which it is attached to the carbon atom of the methylene group —(CH$_2$)n-, via a divalent bridge —CH$_2$— when m is 1, or via a —CH$_2$—CH$_2$— when m is 0, forming a pyrrolidine divalent group, represented by the formula Ib and Ic:

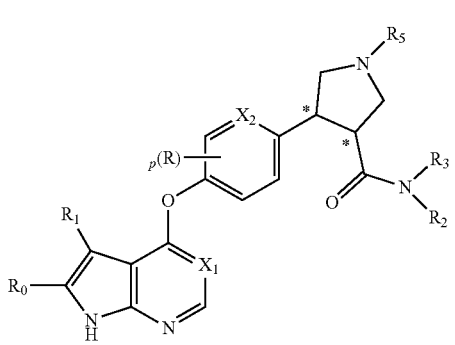

(Ib)

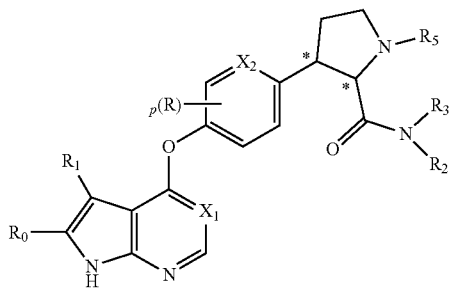

(Ic)

Compounds of formula Ib and Ic contain at least two stereogenic centres, as indicated by the asterisk (*) in the picture above. They may exist as two diastereoisomers, each of them present as a pair of enantiomers. For the sake of graphical representation, a racemic diastereoisomer is drawn as a single absolute configuration with the tag "rac" (in the chemical structure and before the chemical name) indicating the occurrence of a racemic mixture. As an example the compound: rac-(3R,4S)-N-Benzyl-4-(4-((3-methyl-1H-pyrrolo[2,3-b]pyridin-4-yl)oxy)phenyl)pyrrolidine-3-carboxamide (example 17) graphically represented as follows:

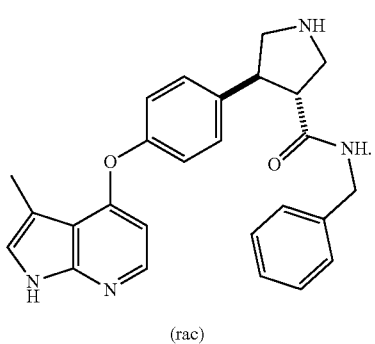

(rac)

indicates the racemic mixture of the two trans diastereoisomers (3R,4S) and (3S, 4R), having the following formulae:

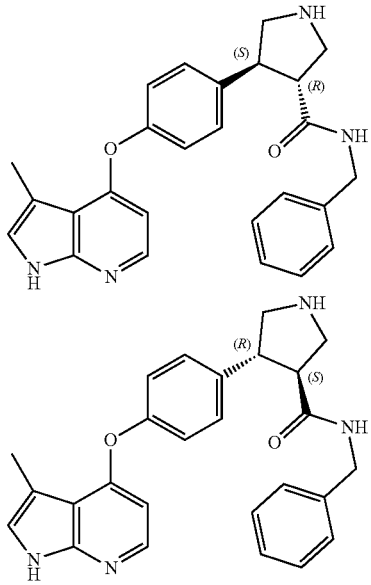

In a further preferred embodiment, the invention is directed to compounds of formula (I) as defined above, wherein when $R_4$ is H or methyl, $R_6$ is H, $R_5$ links to the group $R_2$ to form a methylene —$CH_2$— bridge, forming a tetrahydropyrimidinone divalent group, represented by the formula Id when q is 1, m and n are zero, and Ie when m and n are 1 and q is zero:

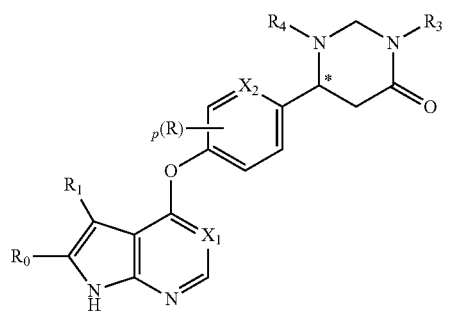

(Id)

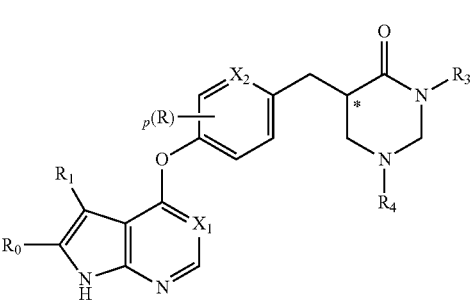

(Ie)

Enantiomerically pure compounds can be prepared according to the reactions described below, by means of enantiomerically pure starting materials and intermediates. Preparation of enantiomerically pure compounds of formula I on the carbon carrying —$R_6$ may be accomplished by means of enantiomerically pure intermediates III and VI as found in the following schemes. These intermediates may be commercially available or readily prepared from commercial sources.

In another approach, enantiomerically pure compounds can be obtained from the corresponding racemates by means of chiral chromatography. Whenever, in compounds of formula I, there are two or more stereogenic centres, the structure is then characterized by different stereoisomers. Stereochemically pure compounds may be obtained by chiral separation from a diastereoisomeric mixture, or stepwise by chromatographic separation of diastereoisomers followed by further chiral separation into single stereoisomers.

Compounds of formula I, wherein $R_5$ and $R_2$ are not taken together to form a cycle, may be prepared according to SCHEME 1 as described hereinafter. SCHEME 1 provides at least one non-limiting synthetic route for the preparation of examples 1 to 35.

Typical protective groups ($PG_1$) for protection of the NH of the 5-membered ring of the bicyclic intermediate II can be 2-[(trimethylsilyl)ethoxy]methyl (SEM), 4-toluenesulfonyl (Ts) and p-methoxybenzil (PMB), as examples of PG1 or other suitable protective groups. Intermediate II may be prepared from the corresponding unprotected heterocycle and a suitable reagent, for example Ts-Cl (tosyl chloride), SEM-Cl ([2-(trimethylsilyl)ethoxy]methyl chloride) or PMB-Br (p-methoxybenzyl bromide). The reaction between said components may be carried out in a polar organic solvent such as DMF or DCM, in the presence of a strong base, such as NaH, at RT or lower.

The carboxylic acid of intermediate III may be suitably protected as an ester with $PG_2$ (for example as the methyl ester) and the amino group protected as a carbamate with $PG_3$ (for example a Boc group). These transformations may be achieved by using known methods starting from commercially available unprotected amino acid derivatives (Protective group in organic syntheses, 3rd ed. T. W. Greene, P. G. M. Wuts).

According to SCHEME 1, intermediate IV may be obtained from Intermediates III and II through a palladium catalyzed O-arylation. For example, the reaction may be carried out by reacting the aryl halide intermediate II and the phenol derivative III in a suitable organic solvent such as toluene or THF, in the presence of an inorganic base such as $K_2CO_3$, with a suitable palladium catalytic system such as $Pd_2dba_3$/XPhos or another palladium source/phosphine based ligand at high temperature (around 100° C.) for a few hours.

Removal of $PG_2$ (when $PG_2$ is a methyl) from intermediate IV to give the intermediate Va, whilst not affecting other protections ($PG_1$: SEM or Ts and $PG_3$: Boc), may be carried out by hydrolysis using an inorganic base such as LiOH in a mixture of methanol/water, generally at RT and for a time ranging from 1 h to overnight. In some cases, for synthetic convenience, the hydrolysis may be carried out at a temperature equal to or higher than 50-60° C. and may lead to concurrent $PG_1$ cleavage (where $PG_1$ is Ts) to give intermediate Vb.

SCHEME 1

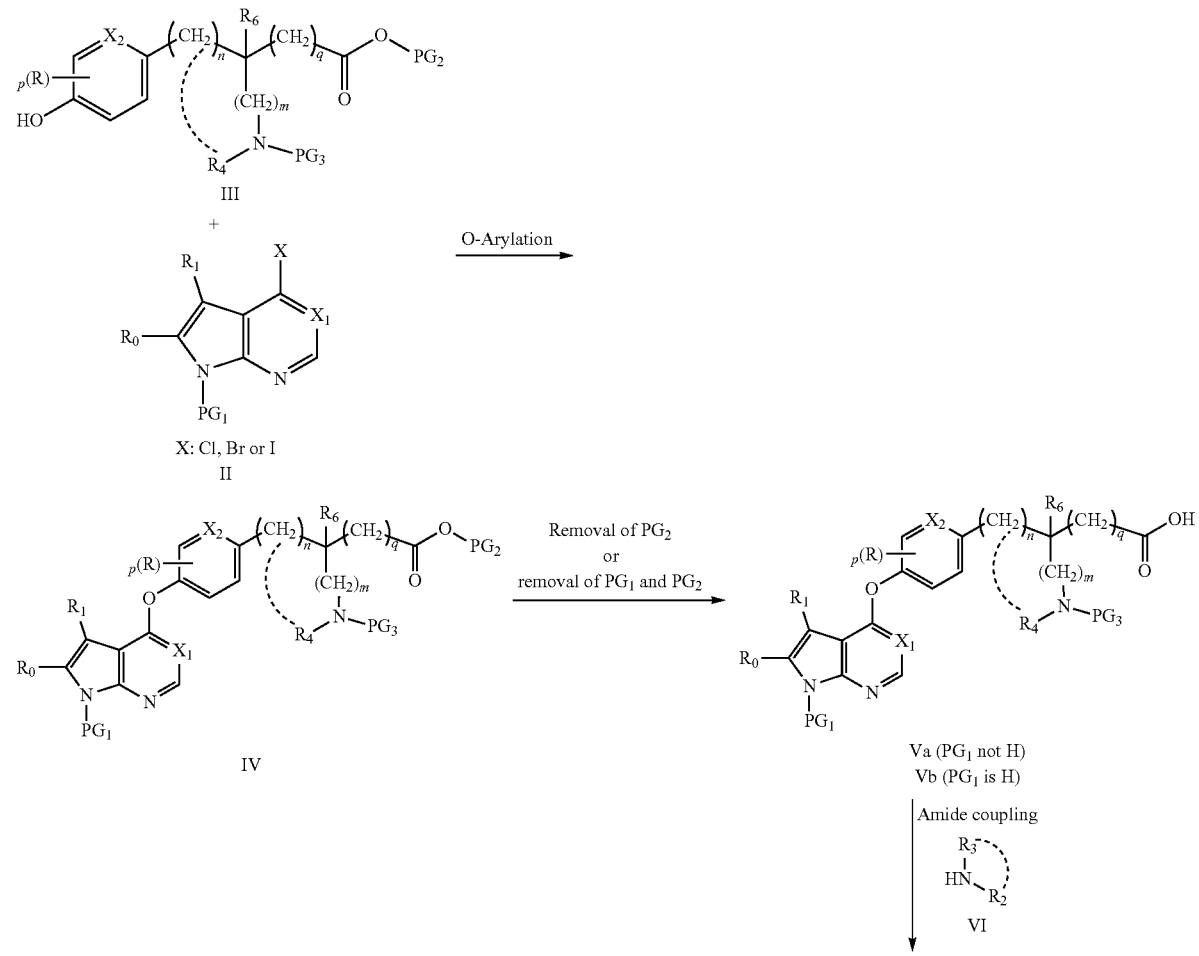

-continued

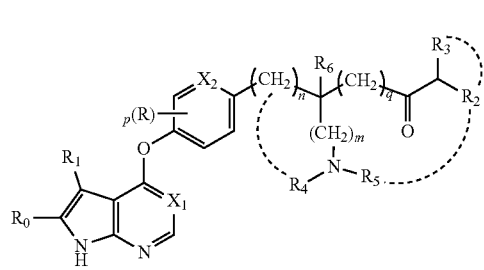

I
(wherein R5 and R2 are not taken together to form a cycle)

Removal of PG$_2$ and PG$_3$
or
removal of PG$_3$

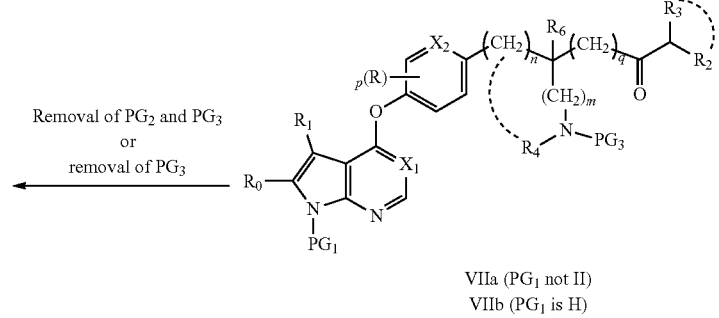

VIIa (PG$_1$ not H)
VIIb (PG$_1$ is H)

Compounds of formula I (wherein $R_5$ and $R_2$ are not taken together to form a cycle) may be prepared from intermediate Va (or Vb) and intermediate VI in a two step synthesis that requires first a amide coupling reaction between acid intermediate Va (or Vb) and amine intermediate VI to give respectively VIIa (or VIIb) and followed by removal of PG$_3$ and PG$_1$ (or PG$_3$). For example, the amide coupling to give VIIa (or VIIb) may be performed by reacting intermediate Va (or Vb) and VI in the presence of an activating agent such as COMU or HATU, with an organic base such as DIPEA or TEA, in a suitable organic solvent such as DCM or DMF, and at temperature generally around RT for a time ranging from a few hours to overnight. Removal of PG$_1$ and PG$_3$ from VIIa (or for VIIb PG$_3$ only) may be achieved stepwise or concurrently according to the cleavage conditions used (Protective group in organic syntheses, 3rd ed. T. W. Greene, P. G. M. Wuts). For example, an acidic cleavage using a mixture of TFA in an organic solvent such as DCM, can deprotect Boc, while SEM may require an extra treatment in concentrated methanolic ammonia, LiOH or NaOH. The tosyl group (Ts) may be hydrolysed in a solution of inorganic base such as LiOH in water/methanol at a temperature equal to or higher that 50° C.

In another embodiment, compounds of formula I (wherein $R_1$ is CN) may be prepared according to SCHEME 2. An intermediate of formula VIII, prepared as previously reported for intermediate IV (wherein $R_1$ is H) in SCHEME 1, may be converted into the intermediate IX (where X is Cl, Br or I) by an electrophilic halogenation with the corresponding NXS (N-halosuccinimide, X: Cl, Br or I) carried out in an organic solvent such as MeCN and at temperature around RT for a few hours. Intermediate IX (where X is Cl, Br or I) may be converted into intermediate X (where X is Cl, Br or I) in the same way as described in SCHEME 1 for intermediate VIIa or VIIb. Intermediate VIIc (where $R_1$ is CN) may be obtained from intermediate X (where X is Cl, Br or I) by a metal catalyzed cyanation, for example using zinc cyanide in the presence of a Pd catalyst, such as Pd$_2$(dba)$_3$/1,1'-ferrocenediylbis(diphenylphosphine), in an organic solvent such as DMF, and at a temperature higher than 100° C. for times up to overnight or longer. Compounds of formula I (wherein $R_1$ is CN) may be obtained from intermediate VIIc (where $R_1$ is CN) by treatment with TFA at RT for times longer than 1 h. The SCHEME 2 provides at least one non-limiting synthetic route for the preparation of examples 44 to 49.

SCHEME 2

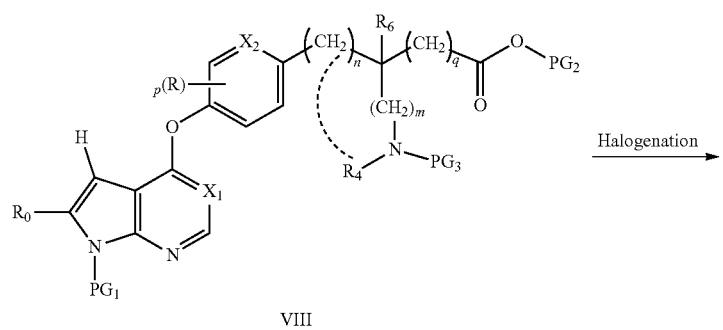

VIII

Halogenation

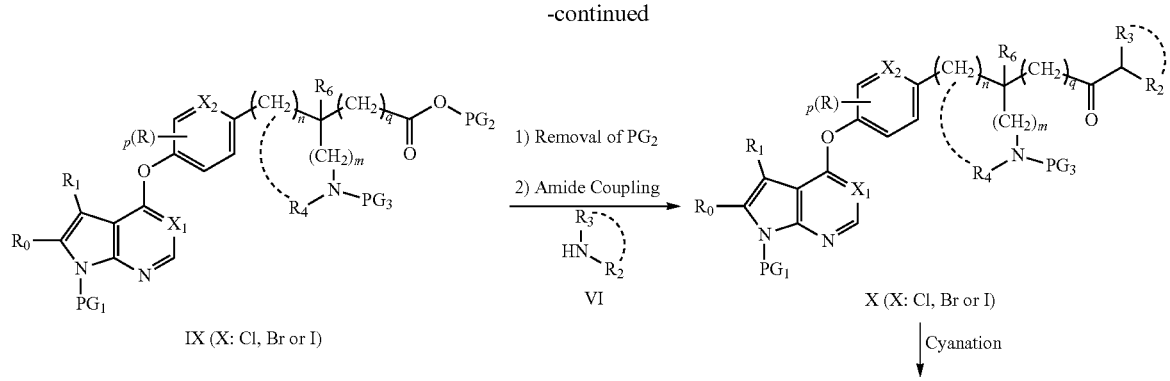

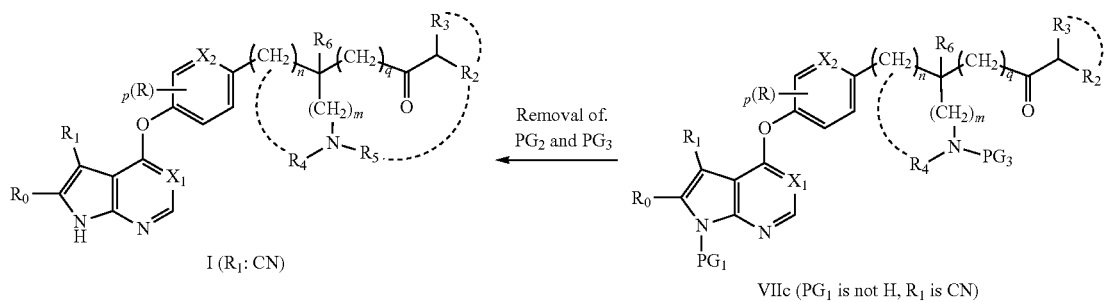

In another embodiment of the invention, compounds of formula I wherein $R_5$ links to the group $R_2$ to form a methylene —$CH_2$— bridge, thus forming a tetrahydropyrimidinone divalent group, represented by the formula Id when q is 1, m and n are zero, and Ie when m and n are 1 and q is zero, may be prepared as depicted in SCHEME 3.

Intermediate VIId (wherein $R_2$ is H, q is 1, m and n are zero) and Intermediate VIIe (wherein $R_2$ is H, m and n are 1 and q is zero) may be prepared in the same way as described for intermediate VIIa in SCHEME 1.

SCHEME 3

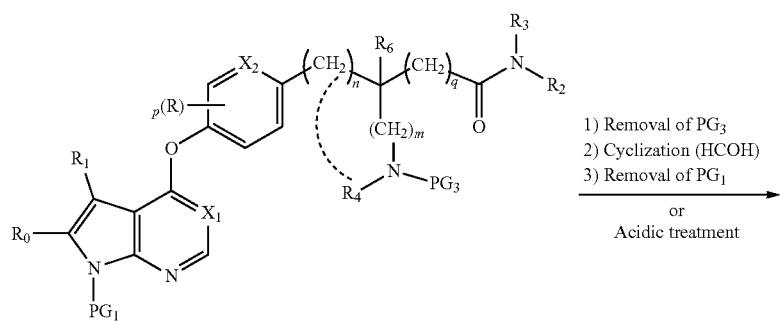

VIId
(wherein $PG_1$ is not H, $R_2$ is H, q is 1, m and n are zero)

VIIe
(wherein $PG_1$ is not H, $R_2$ is H, m and n are 1 and q is zero)

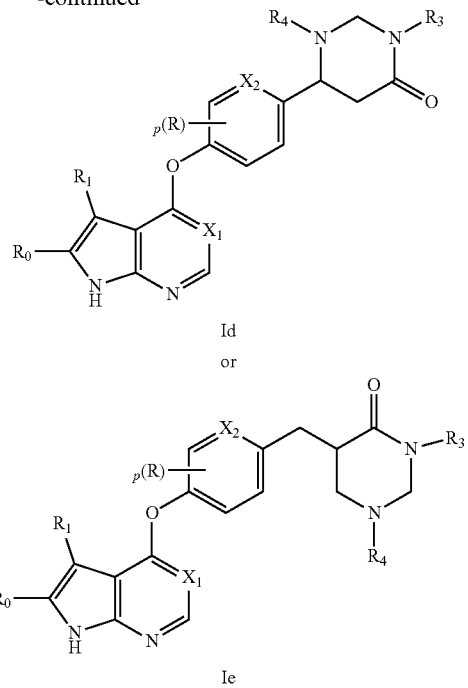

Id
or

Ie

Compound of formula Id and Ie may be prepared from intermediates VIId and VIIe, respectively, by removing $PG_3$, performing the cyclization to insert a methylene bridge and then removing $PG_1$. Removal of $PG_3$ and $PG_1$ can be performed in the same way as described for the synthesis of compounds of formula I in SCHEME 1, while a typical cyclization is performed by reacting the primary amine with a source of formaldehyde in water. SCHEME 3 provides at least one non-limiting synthetic route for the preparation of examples 38 to 43.

SCHEME 4

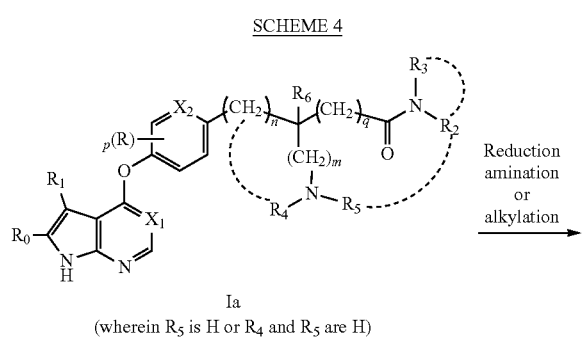

Ia
(wherein $R_5$ is H or $R_4$ and $R_5$ are H)

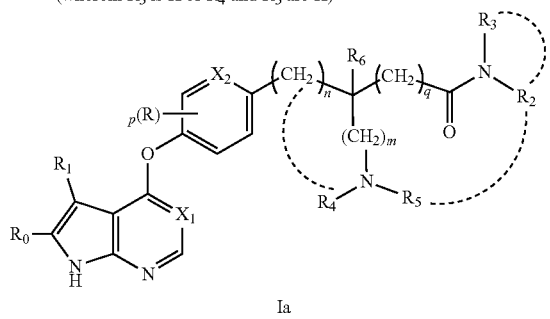

Ia
(wherein $R_5$ or $R_4$ and $R_5$ are alkyl groups)

In another embodiment of the invention, compounds of formula I (where at least $R_5$ is alkyl or $R_4$ and $R_5$ are both alkyl groups) may be prepared from corresponding compounds of formula I (where at least $R_5$ is H or $R_4$ and $R_5$ are both H) by reductive amination or alkylation, as depicted in SCHEME 4.

As an example, where $R_5$ is methyl or $R_4$ and $R_5$ are both methyl, a typical reductive amination may be performed by reacting the starting amine with a source of formaldehyde, such as paraformaldehyde, and a reducing agent such as $NaBH_4$ in an alcoholic solvent such as 1,1,1-trifluorethanol, ethanol or methanol at a temperature above 70° C. and for times up to hours. Where $R_5$ is methyl, or $R_4$ and $R_5$ are both methyl, a typical alkylation procedure may be performed by reacting the starting amine with a methylsulfonate such as trifluoromethanesulfonate in an organic protic solvent such as isopropanol, ethanol or hexafluoroisopropanol generally at room temperature for times up to hours.

The compounds of the invention are inhibitors of kinase activity, in particular Rho-kinase activity. Generally speaking, compounds which are ROCK inhibitors may be useful in the treatment of many disorders associated with ROCK enzymes mechanisms.

In one embodiment, the disorders that can be treated by the compounds of the present invention include glaucoma, inflammatory bowel disease (IBD) and pulmonary diseases selected from asthma, chronic obstructive pulmonary disease (COPD), interstitial lung disease such as idiopathic pulmonary fibrosis (IPF) and pulmonary arterial hypertension (PAH).

In another embodiment, the disorder that can be treated by the compounds of the present invention is selected from the group consisting of asthma, chronic obstructive pulmonary disease (COPD) and interstitial lung disease such as idiopathic pulmonary fibrosis (IPF) and pulmonary arterial hypertension (PAH).

In a further embodiment, the disorder is selected from idiopathic pulmonary fibrosis (IPF) and pulmonary arterial hypertension (PAH).

The methods of treatment of the invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts thereof may be administered once or according to a dosing regimen wherein a number of doses are administered at varying intervals of time for a given period of time. Typical daily dosages may vary depending upon the particular route of administration chosen.

The invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelaps, capsules, caplets, granules, lozenges and bulk powders. The compounds of the invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention can be administered as the sole active agent or in combination (i.e. as co-therapeutic agents administered in fixed dose combination or in combined therapy of separately formulated active ingredients) with other pharmaceutical active ingredients selected from organic nitrates and NO donors; inhaled NO; stimulator of soluble guanylate cyclase (sGC); prostaciclin analogue PGI2 and agonist of prostacyclin receptors; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors; human neutrophilic elastase inhibitors; compounds inhibiting the signal transduction cascade, such as tyrosine kinase and/or serine/threonine kinase inhibitors; antithrombotic agents, for example platelet aggregation inhibitors, anticoagulants or profibrinolytic substances; active substances for lowering blood pressure, for example calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists; neutral endopeptidase inhibitor; osmotic agents; ENaC blockers; anti-inflammatory including corticosteroids and antagonists of chemokine receptors; bronchodilators for example beta2agonist and muscarinic antagonists; antihistamine drugs; anti-tussive drugs; antibiotics such as macrolide and DNase drug substances and selective cleavage agents such as recombinant human deoxyribonuclease I (rhDNase); agents that inhibit ALK5 and/or ALK4 phosphorylation of Smad2 and Smad3; tryptophan hydroylase 1 (TPH1) inhibitors and multi-kinase inhibitors.

In a preferred embodiment, the compounds of the invention are dosed in combination with phosphodiesterase V such as sildenafil, vardenafil and tadalafil; organic nitrates and NO donors (for example sodium nitroprusside, nitroglycerin, isosorbide mononitrate, isosorbide dinitrate, molsidomine or SIN-1, and inhaled NO); synthetic prostaciclin analogue PGI2 such as iloprost, treprostinil, epoprostenol and beraprost; agonist of prostacyclin receptors such as selexipag and compounds of WO 2012/007539; stimulator of soluble guanylate cyclase (sGC) like riociguat and tyrosine kinase like imatinib, sorafenib and nilotinib and endothelin antagonist (for example macitentan, bosentan, sitaxentan and ambrisentan).

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage comprised between 0.001 and 1000 mg/day, preferably between 0.1 and 500 mg/day.

When the compounds of formula (I) are administered by inhalation route, they are preferably given at a dosage comprised between 0.001 and 500 mg/day, preferably between 0.1 and 100 mg/day.

A pharmaceutical composition comprising a compound of the invention suitable to be administered by inhalation, such as inhalable powders, propellant-containing metering aerosols or propellant-free inhalable formulations.

The invention is also directed to a device comprising the pharmaceutical composition comprising a compound according to the invention, which may be a single- or multi-dose dry powder inhaler, a metered dose inhaler and a soft mist nebulizer.

The following examples illustrate the invention.

PREPARATIONS OF INTERMEDIATES AND EXAMPLES

General Experimental Details

Purification by chromatography refers to purification using the CombiFlash® Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 μm and nominal 60 Å porosity. Fractions containing the required product (identified by TLC and/or LCMS analysis) were pooled and concentrated in vacuo. Where an SCX-2 cartridge was used, 'SCX-2 cartridge' refers to an Isolute® pre-packed polypropylene column containing a non-end-capped propylsulphonic acid functionalised silica strong cation exchange sorbent. Where HPLC was used for purification (Purification by MDAP) fractions containing the required product (identified by TLC and/or LCMS analysis) were pooled and the solvent removed using a Biotage EV10 Evaporator. Alternatively the pooled product fraction was lyophilised.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz or on a Bruker Fourier 300 spectrometer with a 5 mm dual probe operating at 300 MHz or on a Varian MR-400 (400 MHz) spectrometer equipped with a selfshielded z-gradient coil and a 5 mm 1H/nX broad-band probehead. Shifts are given in ppm relative to tetramethylsilane.

LC-MS Method 1

Waters Micromass ZQ2000 mass spectrometer with a C18-reverse-phase column (100×2.1 mm Acquity BEH with 1.7 μm particle size) maintained at 40° C., elution with A: water+0.1% formic acid; B: MeCN+0.1% formic acid.

Gradient:

| Gradient - Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionisation method-Electrospray (positive/negative ion).

LC-MS Method 2

Waters Micromass ZQ2000 mass spectrometer with a C18-reverse-phase column (100×2.1 mm Acquity BEH with 1.7 μm particle size) maintained at 40° C., elution with A: water+0.1% aqueous ammonia; B: MeCN+0.1% aqueous ammonia.

Gradient:

| Gradient - Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionisation method-Electrospray (positive/negative ion).

LC-MS Method 3

Quattro Micro Mass Spectrometer with a C18-reverse-phase column (100×2.1 mm Acquity BEH with 1.7 μm particle size) maintained at 40° C., elution with A: water+0.1% formic acid; B: MeCN+0.1% formic acid.

Gradient:

| Gradient - Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionisation method-Electrospray (positive/negative ion).

LC-MS Method 4

QDa Mass Spectrometer with a C18-reverse-phase column (50×2.1 mm Acquity CSH with 1.7 μm particle size) maintained at 40° C., elution with A: water+0.1% formic acid; B: MeCN+0.1% formic acid.

Gradient:

| Gradient - Time | flow (mL/min) | % A | % B |
|---|---|---|---|
| 0.00 | 1 | 97 | 3 |
| 1.50 | 1 | 1 | 99 |

-continued

| Gradient - Time | flow (mL/min) | % A | % B |
|---|---|---|---|
| 1.90 | 1 | 1 | 99 |
| 2.00 | 1 | 97 | 3 |
| 2.50 | 1 | 97 | 3 |

Detection-MS, UV PDA

MS ionisation method-Electrospray (positive/negative ion).

LC-MS Method 5

QDa Mass Spectrometer with a C18-reverse-phase column (50×2.1 mm Acquity BEH with 1.7 μm particle size) maintained at 50° C., elution with A: water+0.1% formic acid; B: MeCN+0.1% formic acid.

Gradient:

| Gradient - Time | flow (mL/min) | % A | % B |
|---|---|---|---|
| 0.00 | 1 | 97 | 3 |
| 1.50 | 1 | 1 | 99 |
| 1.90 | 1 | 1 | 99 |
| 2.00 | 1 | 97 | 3 |
| 2.50 | 1 | 97 | 3 |

Detection-MS, UV PDA

MS ionisation method-Electrospray (positive/negative ion).

LC-MS Method 6

Waters Platform LC with a C18-reverse-phase column (30×4.6 mm Phenomenex Luna 3 μm particle size), elution with A: water+0.1% formic acid; B: acetonitrile+0.1% formic acid.

Gradient:

| Gradient - Time | flow (mL/min) | % A | % B |
|---|---|---|---|
| 0.00 | 2 | 95 | 5 |
| 0.50 | 2 | 95 | 5 |
| 4.50 | 2 | 5 | 95 |
| 5.50 | 2 | 5 | 95 |
| 6.00 | 2 | 95 | 5 |

Detection-MS, ELS, UV (100 μl split to MS with in-line UV detector)

MS ionisation method-Electrospray (positive and negative ion).

LC-MS Method 7

ZQ Mass Spectrometer with a C18-reverse-phase column (30×4.6 mm Phenomenex Luna with 3 μm particle size), elution with A: water+0.1% formic acid; B: MeCN+0.1% formic acid.

Gradient:

| Gradient - Time | flow (mL/min) | % A | % B |
|---|---|---|---|
| 0.0 | 2 | 95 | 05 |
| 0.3 | 2 | 95 | 05 |
| 4.3 | 2 | 05 | 95 |
| 5.3 | 2 | 05 | 95 |

-continued

| Gradient - Time | flow (mL/min) | % A | % B |
|---|---|---|---|
| 5.8 | 2 | 95 | 05 |
| 6.0 | 2 | 95 | 05 |

Detection-MS, UV PDA

MS ionisation method-Electrospray (positive/negative ion).

LC-MS Method 8

QDa Mass Spectrometer with a C18-reverse-phase column (50×2.1 mm Acquity CSH with 1.7 μm particle size) maintained at 40° C., elution with A: 95/5 water/acetonitrile+0.05% formic acid; B: acetonitrile/water+0.05% formic acid.

Gradient:

| Gradient - Time | flow (mL/min) | % A | % B |
|---|---|---|---|
| 0.00 | 1 | 99 | 1 |
| 1.50 | 1 | 1 | 99 |
| 1.90 | 1 | 1 | 99 |
| 2.00 | 1 | 99 | 1 |

Detection-MS, UV PDA

MS ionisation method-Electrospray (positive/negative ion).

MDAP Method

Agilent Technologies 1260 Infinity purification system with an XBridge Prep C18 OBD column (19×250 mm, 5 μm OBD) maintained at RT Mobile Phase A: 0.1% aqueous ammonia Mobile Phase B: 0.1% ammonia in acetonitrile Flow Rate: 20 ml/min Gradient Program: 10%-95%, 22 min, centered on a specific focused gradient Sample: Injection of a 20-60 mg/ml solution in DMSO+ optional formic acid and water)

SFC Methods

Supercritical Fluid Chromatography (SFC) was carried out using either a Waters Thar Prep100 preparative SFC system (P200 $CO_2$ pump, 2545 modifier pump, 2998 UV/VIS detector, 2767 liquid handler with Stacked Injection Module) or a Waters Thar Investigator semi preparative system (Waters Fluid Delivery Module, 2998 UV/VIS detector, Waters Fraction Collection Module). The column and isocratic method used is indicated for each compound and the single enantiomers were analysed using the methods given. Some of the compounds may have gone through a second purification process in order to achieve the required % ee purity.

Preparative HPLC Method (Acidic Conditions)

Where compounds were purified by HPLC they were carried out on a C18-reverse-phase column (250×21.2 mm Phenomenex Kinetex with 5 μm particle size). Specific eluting mixtures are described and, unless otherwise stated, peaks were detected by UV (254 nm). Fractions containing the pure product were generally combined and freeze-dried to give a solid.

Preparative HPLC Method (Basic Conditions)

Where compounds were purified by HPLC they were carried out on a C18-reverse-phase column (250×21.2 mm Phenomenex Kinetex EVO with 5 μm particle size). Specific eluting mixtures are described and, unless otherwise stated, peaks were detected by UV (254 nm). Fractions containing the pure product were generally combined and freeze-dried to give a solid.

Abbreviations Used in the Experimental Section:

COMU=(1-Cyano-2-ethoxy-2-oxoethylidenaminooxy)-dimethylaminomorpholino-carbenium hexafluorophosphate; DCM=Dichloromethane; DIPEA=Di-isopropylethylamine; DMF=N,N-dimethylformamide; DMSO=Dimethylsulphoxide; h=Hour(s); HFIP=Hexafluoro-2-propanol; HPLC=High performance liquid chromatography; LCMS=Liquid chromatography-mass spectrometry; MDAP=Mass-directed autopurification; NIS=N-Iodosuccinimide; $Pd_2(dba)_3$=Tris(dibenzylideneacetone)dipalladium(0); dppf=1,1'-Bis(diphenylphosphino) ferrocene; Rt=Retention time; RT=Room temperature; SFC=Supercritical Fluid Chromatography; TFA=Trifluoroacetic acid; THF=Tetrahydrofuran; XPhos=2-Dicyclohexylphosphino-2',4',6'-triisopropylbiphenyl; Si=Silica gel; In the procedures that follow, some of the starting materials are identified through an "Intermediate" or "Example" number with indications on step number. This is provided merely for assistance to the skilled chemist.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The present invention will now be further described by the following examples.

Preparation of Intermediate 1A-a

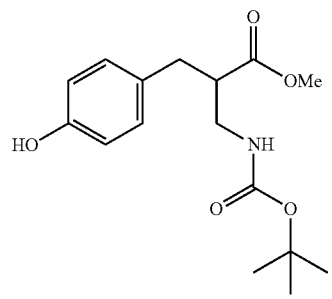 [SMILES: COC(=O)C(CNC(=O)OC(C)(C)C)Cc1ccc(O)cc1]

Methyl 3-((tert-butoxycarbonyl)amino)-2-(4-hydroxybenzyl)propanoate (Intermediate 1A-a)

Methyl 3-amino-2-(4-hydroxybenzyl)propanoate (1.0 g, 4.07 mmol) and DIPEA (2.12 μL, 12.2 mmol) were stirred at RT in DCM (50 mL) for 5 min before the addition of di-tert-butyl dicarbonate (888 mg, 4.07 mmol). The reaction mixture was stirred for a further 2 h, diluted with DCM (50 mL) and washed with water (50 mL). The organic solution was dried ($Na_2SO_4$) and evaporated in vacuo. The crude product was chromatographed on a 25 g Si cartridge eluting with 0-50% ethyl acetate in cyclohexane to give Intermediate 1A-a after evaporation of the appropriate fractions (1.29 g).

LCMS (Method 7): Rt=2.88 min, m/z 332.1 $[M+Na]^+$

Preparation of Intermediates 1A-b to 1A-f

The following intermediates were prepared in a similar manner to Intermediate 1A-a by replacing the amino ester with the indicated starting materials.

| Intermediate | Structure | Starting material | LC-MS |
|---|---|---|---|
| 1A-b | 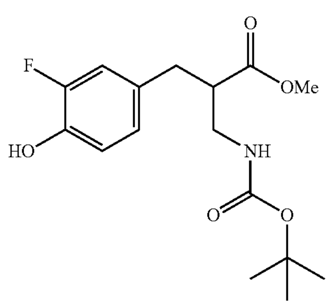 [SMILES: COC(=O)C(CNC(=O)OC(C)(C)C)Cc1ccc(O)c(F)c1] | Methyl 3-amino-2-(3-fluoro-4-hydroxybenzyl)propanoate | Rt = 1.31 min, m/z 350.1 $[M + Na]^+$ (Method 4) |
| 1A-c | 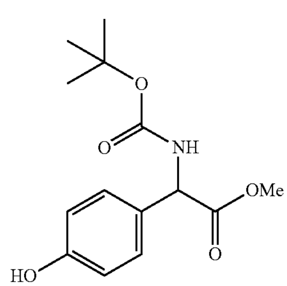 [SMILES: COC(=O)C(NC(=O)OC(C)(C)C)c1ccc(O)cc1] | Methyl 2-amino-2-(4-hydroxyphenyl)acetate | Rt = 2.95 min, m/z 280.2 $[M - H]^-$ (Method 6) |

-continued

| Intermediate | Structure | Starting material | LC-MS |
|---|---|---|---|
| 1A-d | 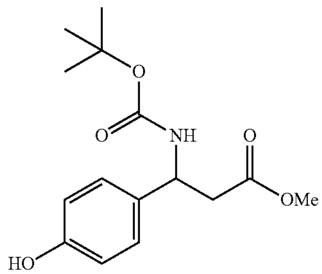 [SMILES: COC(=O)CC(NC(=O)OC(C)(C)C)c1ccc(O)cc1] | Methyl 3-amino-3-(4-hydroxyphenyl)propanoate | Rt = 1.48 min, m/z 318.2 [M + Na]+ (Method 5) |
| 1A-e | 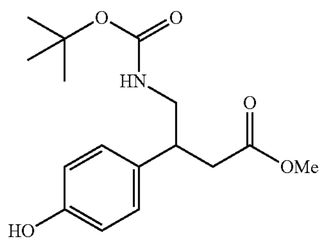 [SMILES: COC(=O)CC(CNC(=O)OC(C)(C)C)c1ccc(O)cc1] | Methyl 4-amino-3-(4-hydroxyphenyl)butanoate | Rt = 1.67 min, m/z 332.1 [M + Na]+ (Method 4) |
| 1A-f | 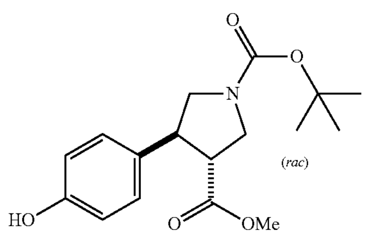 | Rac-1-(tert-butyl) 3-methyl (3R,4S)-4-(4-hydroxyphenyl)pyrrolidine-1,3-dicarboxylate | Rt = 3.06 min, m/z 320.4 [M − H]− (Method 7) |

Preparation of Intermediates 1A-g

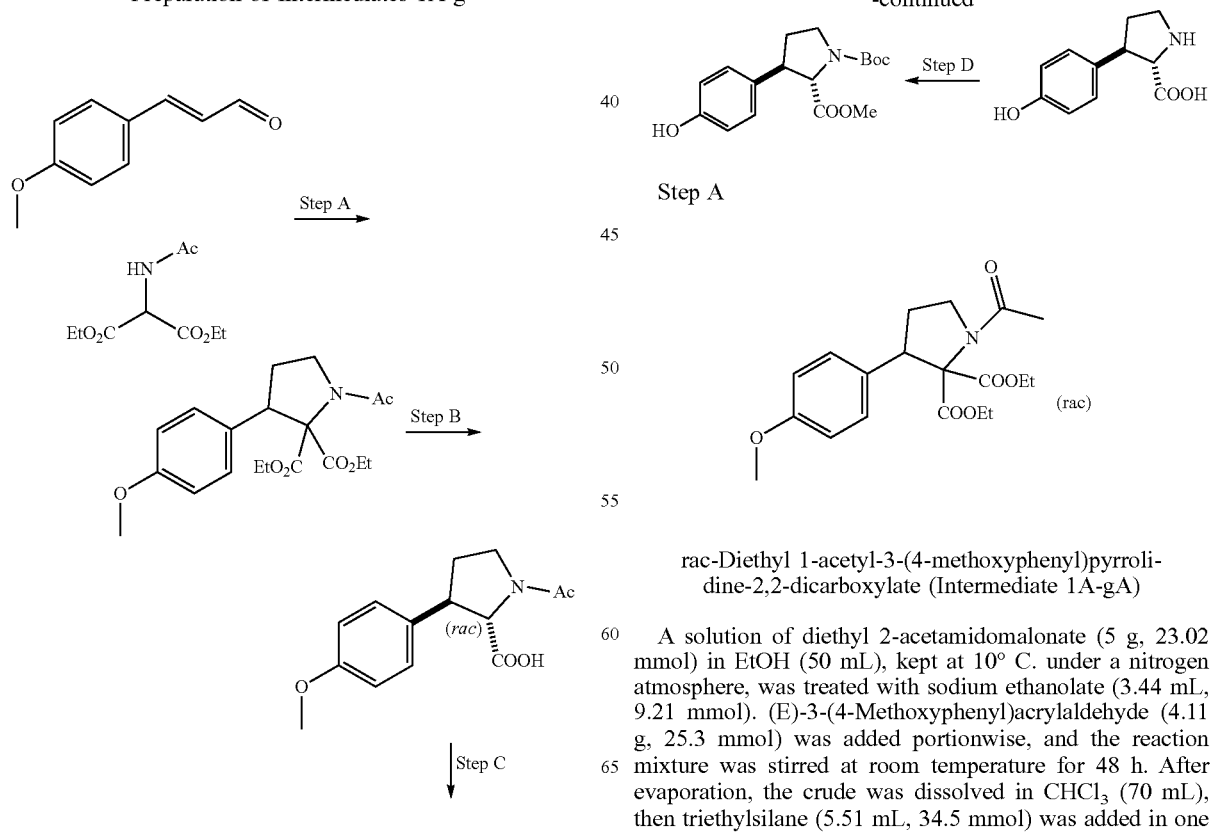

rac-Diethyl 1-acetyl-3-(4-methoxyphenyl)pyrrolidine-2,2-dicarboxylate (Intermediate 1A-gA)

A solution of diethyl 2-acetamidomalonate (5 g, 23.02 mmol) in EtOH (50 mL), kept at 10° C. under a nitrogen atmosphere, was treated with sodium ethanolate (3.44 mL, 9.21 mmol). (E)-3-(4-Methoxyphenyl)acrylaldehyde (4.11 g, 25.3 mmol) was added portionwise, and the reaction mixture was stirred at room temperature for 48 h. After evaporation, the crude was dissolved in CHCl$_3$ (70 mL), then triethylsilane (5.51 mL, 34.5 mmol) was added in one portion followed by dropwise addition of TFA (17.62 mL, 230 mmol) over 20 minutes. The mixture was stirred at room temperature for 2 h. After evaporation of the solvent, the crude residue was redissolved in EtOAc (50 mL) and then washed with sat NaHCO₃ (3×100 mL). The organic layer was washed with brine, dried (Na₂SO₄), filtered and concentrated to dryness. The crude product was chromatographed on a 100 g Si cartridge eluting with 0-10% MeOH in DCM affording the desired product (7.1 g, 85%).

LCMS (Method 8): Rt=0.90 min; m/z=364.3 [M−H]⁺

Step B

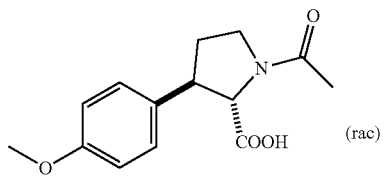

rac-(2S,3R)-1-Acetyl-3-(4-methoxyphenyl)pyrrolidine-2-carboxylic acid (Intermediate 1A-gB)

Intermediate 1A-gA (7.1 g, 19.54 mmol) was suspended in aqueous 0.5 M NaOH (200 mL, 100 mmol) and stirred at RT for 18 h. The aqueous solution was extracted once with EtOAc (30 mL) and then acidified to pH2 with aqueous 2N HCl. The insoluble residue was dissolved in CHCl₃ (30 mL) and the aqueous phase was extracted with CHCl₃ (2×30 mL). The combined organic fractions were dried (Na₂SO₄), filtered and concentrated to dryness. The crude was dissolved in toluene (100 mL) and heated at 75° C. for 1 h. After evaporation of the solvent, the residue was dissolved in 1M NaOEt in EtOH (195 mL, 195 mmol) and ethyl trifluoroacetate (2.1 mL, 19.53 mmol), and refluxed for 2 h. After cooling down to room temperature, water (13 mL) was added and the solution was stirred at room temperature for 2.5 h. Ethanol was evaporated and the aqueous phase was washed with EtOAc (2×40 mL). The pH of the aqueous phase was adjusted to ≈1 with aqueous HCl 2N, and extracted with EtOAc (2×40 mL). The organic phase was dried over Na₂SO₄, filtered and concentrated to dryness to afford the title compound (4.05 g).

LCMS (Method 8): Rt=0.66 min; m/z=364.2 [M−H]⁺

Step C

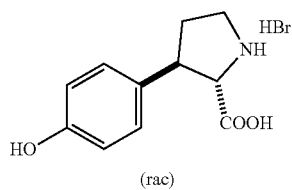

rac-(2S,3R)-3-(4-hydroxyphenyl)pyrrolidine-2-carboxylics acid hydrobromide (Intermediate 1A-gC)

Intermediate 1A-gB (4.05 g, 15.38 mmol) was dissolved in acetic acid (5 mL, 15.38 mmol) followed by the addition of hydrogen bromide 48% (22 mL, 15.38 mmol). The mixture was heated at reflux for 6 h. The crude was concentrated to dryness, then azeotroped by co-evaporation with MeCN (2×25 mL) and toluene (2×25 mL). The resulting crude (4.43 g) was used without further purifications in the following steps.

LCMS (Method 8): Rt 0.17-0.22 min; m/z=208.2 [M−H]⁺

Step D

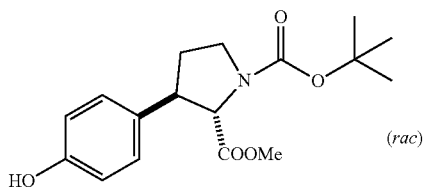

rac-1-(tert-butyl) 2-methyl (2S,3R)-4-(4-hydroxyphenyl)pyrrolidine-1,2-dicarboxylate (Intermediate 1A-g)

To a cooled (ice-bath) solution of Intermediate 1A-gC (4.43 g, 15.37 mmol) in MeOH (150 mL), thionyl chloride (5.61 ml, 77 mmol) was dropped over 5 min. The solution was stirred at room temperature for 6 h. After evaporation of the solvents, the crude residue was dissolved in THF (150 mL) and saturated aqueous NaHCO₃ (50 mL) was added until the pH was greater than 7. di-tert-Butyl dicarbonate (3.69 g, 16.91 mmol) was then added in one portion. The solution was stirred at room temperature for 1 h, then it was diluted with EtOAc (200 mL) and washed with saturated aqueous NaHCO₃ (200 mL) and brine (200 mL). The organic phase was dried (Na₂SO₄), filtered and concentrated to dryness.

The crude product was chromatographed on a Si cartridge eluting with 0-10% MeOH in DCM to afford the title compound (0.87 g).

LCMS (Method 8): Rt=0.92 min; m/z=344.2 [M−Na]⁺, 222.2 [M−Boc]⁺

Intermediate 1B-a

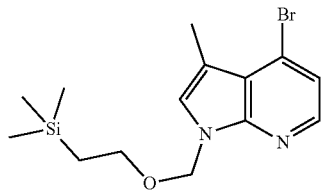 [SMILES: Cc1cn(COCC[Si](C)(C)C)c2nccc(Br)c12]

4-Bromo-3-methyl-1-((2-(trimethylsilyl)ethoxy)methyl)-1H-pyrrolo[2,3-b]pyridine (Intermediate 1B-a)

4-Bromo-3-methyl-7-azaindole (4.0 g, 18.95 mmol) was dissolved in DMF (37 mL) and the solution was cooled in an ice bath. Sodium hydride (60% on mineral oil, 1.14 g, 28.43 mmol) was added and the mixture was stirred under a nitrogen stream for 1 h. 2-(Trimethylsilyl)ethoxymethyl chloride (4.0 mL, 22.74 mmol) was added dropwise, then the reaction mixture was stirred for a further 30 min. After quenching with water (20 mL), the product was extracted into ethyl acetate (3×20 mL). The combined extracts were dried (Na₂SO₄) and evaporated. The residue was chromatographed on a 120 g Si cartridge eluting with 0-25% ethyl acetate in cyclohexane to give Intermediate 1B-a as a colourless oil (3.78 g).

LCMS (Method 5): Rt=1.90 min, m/z 341.1/343.0 [M+H]⁺

Preparation of Intermediates from 1B-b and 1B-c

The following intermediates were prepared in a similar manner to Intermediate 1B-a from the indicated starting materials.

| Intermediate | Structure | Starting materials | LC-MS |
|---|---|---|---|
| 1B-b | (4-bromo-7-azaindole with SEM group) | 4-Bromo-7-azaindole | Rt = 4.63 min, m/z 209.0/211.0 [M − OCH$_2$CH$_2$SiMe$_3$]$^+$ (Method 6) |
| 1B-c | (4-bromo-2-methyl-7-azaindole with SEM group) | 4-Bromo-2-methyl-7-azaindole | Rt = 4.60 min, m/z 340.9/342.9 [M + H]$^+$ (Method 7) |

Intermediate 1C-a

Methyl 3-((tert-butoxycarbonyl)amino)-2-(4-((3-methyl-1-((2-(trimethylsilyl)ethoxy)methyl)-1H-pyrrolo[2,3-b]pyridin-4-yl)oxy)benzyl)propanoate (Intermediate 1C-a)

A mixture of Intermediates 1A-a (408 mg, 1.32 mmol) and 1B-a (500 mg, 1.47 mmol), Pd$_2$(dba)$_3$ (67 mg, 0.073 mmol), XPhos (70 mg, 0.15 mmol), and potassium carbonate (608 mg, 4.40 mmol) in toluene (10 mL) was stirred at 95° C. for 4 h, and then allowed to cool to RT before filtering through Celite®. The solvent was evaporated and the residue was taken up into water (15 mL) and extracted with ethyl acetate (3×20 mL). The combined organic extracts were washed with brine (30 mL), dried (Na$_2$SO$_4$) and evaporated. The crude product was chromatographed on a 25 g Si cartridge eluting with 0-50% ethyl acetate in cyclohexane. The product was obtained as a beige solid (450 mg).

LCMS (Method 7): Rt=4.53 min, m/z 570.1 [M+H]$^+$

Preparation of Intermediates from 1C-b to 1C-g

The following intermediates were prepared in a similar manner to Intermediate 1C-a from the indicated starting materials.

| Intermediate | Structure | Starting materials | LC-MS |
|---|---|---|---|
| 1C-b | (structure shown) | 1A-c and 1B-b | Rt = 4.33 min, m/z 528.1 [M + H]$^+$ (Method 7) |

-continued
| Intermediate | Structure | Starting materials | LC-MS |
|---|---|---|---|
| 1C-c | 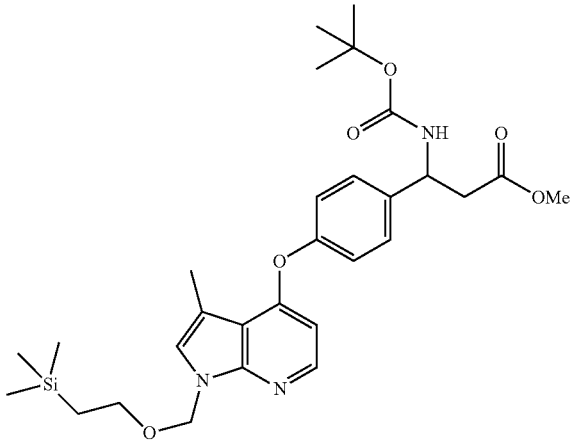 [SMILES: COC(=O)CC(NC(=O)OC(C)(C)C)c1ccc(Oc2ccnc3c2c(C)cn3COCC[Si](C)(C)C)cc1] | 1A-d and 1B-a | Rt = 2.47 min, m/z 556.4 [M + H]+ (Method 5) |
| 1C-d | 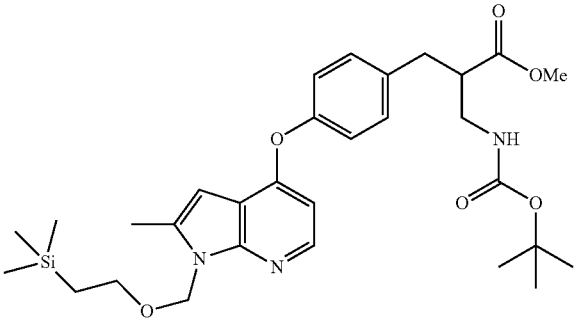 [SMILES: COC(=O)C(CNC(=O)OC(C)(C)C)Cc1ccc(Oc2ccnc3c2cc(C)n3COCC[Si](C)(C)C)cc1] | 1A-a and 1B-c | Rt = 4.56 min, m/z 570.1 [M + H]+ (Method 7) |
| 1C-e | 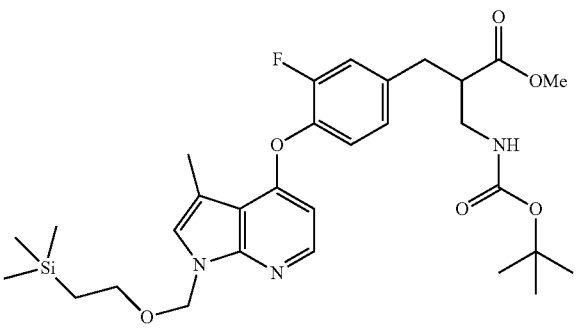 [SMILES: COC(=O)C(CNC(=O)OC(C)(C)C)Cc1ccc(Oc2ccnc3c2c(C)cn3COCC[Si](C)(C)C)c(F)c1] | 1A-b and 1B-a | Rt = 1.89 min, m/z 588.5 [M + H]+ (Method 4) |
| 1C-f | 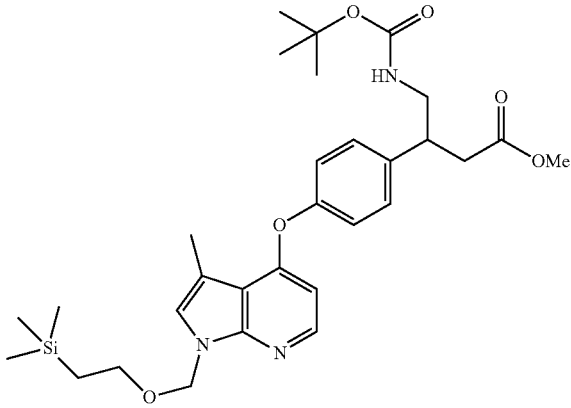 [SMILES: COC(=O)CC(CNC(=O)OC(C)(C)C)c1ccc(Oc2ccnc3c2c(C)cn3COCC[Si](C)(C)C)cc1] | 1A-e and 1B-a | Rt = 1.88 min, m/z 570.2 [M + H]+ (Method 4) |

-continued

| Intermediate | Structure | Starting materials | LC-MS |
|---|---|---|---|
| 1C-g | (structure shown) (rac) | 1A-f and 1B-a | Rt = 4.70 min, m/z 582.3 [M + H]+ (Method 7) |
| 1C-h | (structure shown) (rac) | 1A-g and 1B-a | Rt = 1.60 min, m/z 582 [M − H]+ (Method 8) |

Intermediate 1D-a 3-((tert-Butoxycarbonyl)amino)-2-(4-((3-methyl-1-((2-(trimethylsilyl)ethoxy)methyl)-1H-pyrrolo[2,3-b]pyridin-4-yl)oxy)benzyl)propanoic acid (Intermediate 1D-a)

Intermediate 1C-a (445 mg, 0.78 mmol) was dissolved in a mixture of methanol (4 mL), water (4 mL) and THF (8 mL). Lithium hydroxide hydrate (98 mg, 2.34 mmol) was added and the reaction mixture was stirred at RT for 45 min. The reaction mixture was partitioned between ethylacetate (20 mL) and brine (10 mL). The organic layer was dried (Na₂SO₄) and evaporated to give a yellow oil (217 mg).

LCMS (Method 7): Rt=4.12 min, m/z 556.1 [M+H]+

Preparation of Intermediates from 1D-b to 1D-g

The following intermediates were prepared in a similar manner to Intermediate 1D-a from the indicated starting material.

| Intermediate | Structure | Starting materials | LC-MS |
|---|---|---|---|
| 1D-b | 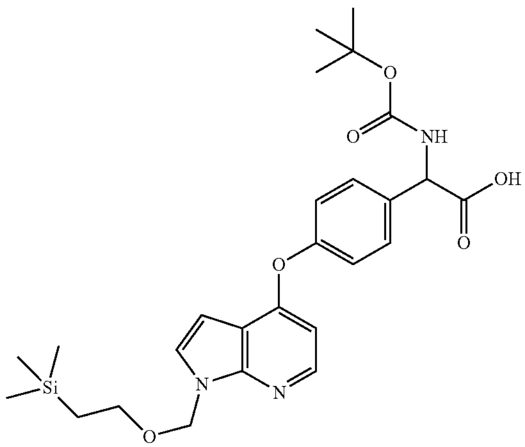 [SMILES: CC(C)(C)OC(=O)NC(C(=O)O)c1ccc(Oc2ccnc3c2ccn3COCC[Si](C)(C)C)cc1] | 1C-b | Rt = 4.22 min, m/z 514.2 [M + H]+ (Method 6) |
| 1D-c | 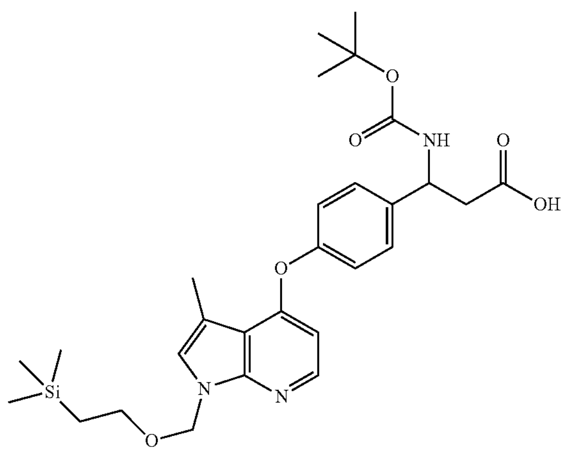 [SMILES: Cc1cn(COCC[Si](C)(C)C)c2nccc(Oc3ccc(C(CC(=O)O)NC(=O)OC(C)(C)C)cc3)c12] | 1C-c | Rt = 3.97 min, m/z 542.2 [M + H]+ (Method 7) |
| 1D-d | 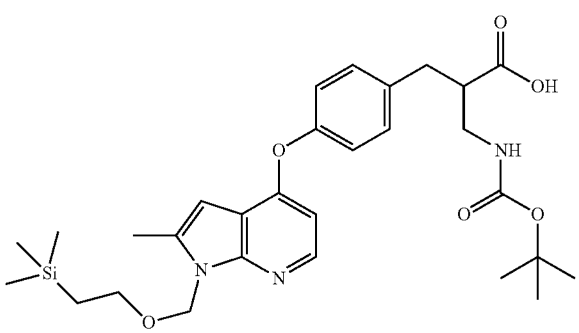 [SMILES: Cc1cc2c(Oc3ccc(CC(CNC(=O)OC(C)(C)C)C(=O)O)cc3)ccnc2n1COCC[Si](C)(C)C] | 1C-d | Rt = 1.77 min, m/z 556.4 [M + H]+ (Method 4) |
| 1D-e | 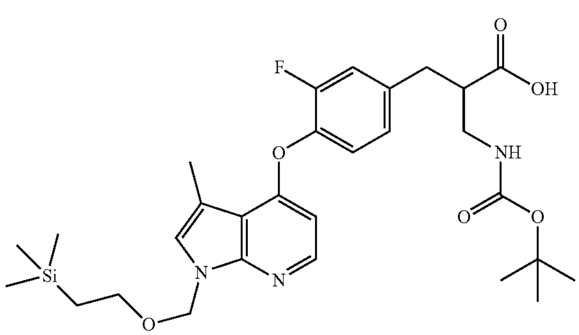 [SMILES: Cc1cn(COCC[Si](C)(C)C)c2nccc(Oc3ccc(CC(CNC(=O)OC(C)(C)C)C(=O)O)cc3F)c12] | 1C-e | Rt = 1.80 min, m/z 574.4 [M + H]+ (Method 4) |

-continued

| Intermediate | Structure | Starting materials | LC-MS |
|---|---|---|---|
| 1D-f | 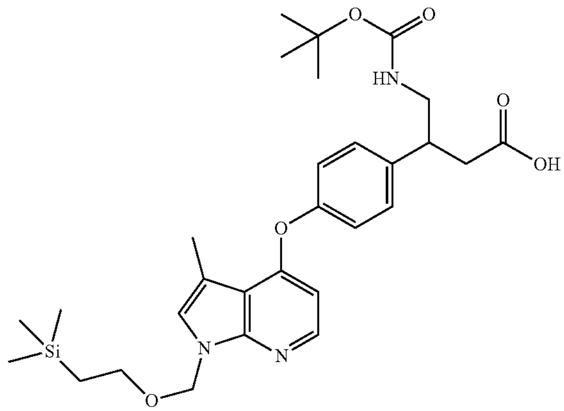 [SMILES: Cc1cn(COCC[Si](C)(C)C)c2nccc(Oc3ccc(C(CNC(=O)OC(C)(C)C)CC(=O)O)cc3)c12] | 1C-f | Rt = 1.77 min, m/z 556.2 [M + H]+ (Method 4) |
| 1D-g | (rac) | 1C-g | Rt = 4.31 min, m/z 568.3 [M + H]+ (Method 7) |
| 1D-h | (rac) | 1C-h | Rt = 1.48 min, m/z 568 [M − H]+ (Method 8) |

Example 1

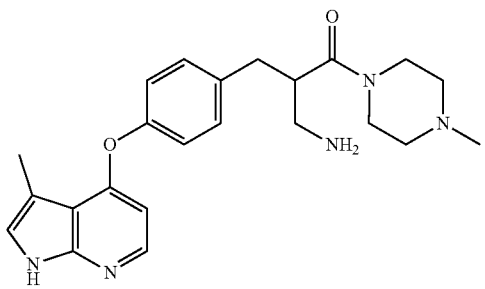 [SMILES: Cc1c[nH]c2nccc(Oc3ccc(CC(CN)C(=O)N4CCN(C)CC4)cc3)c12]

3-Amino-2-(4-((3-methyl-1H-pyrrolo[2,3-b]pyridin-4-yl)oxy)benzyl)-1-(4-methylpiperazin-1-yl)propan-1-one (Example 1)

Intermediate 1D-a (217 mg, 0.39 mmol), 1-methylpiperazine (43 mg, 0.43 mmol) and COMU (201 mg, 0.47 mmol) were dissolved in DCM (5 mL) and DIPEA (0.15 mL, 0.86 mmol) was added. The reaction was stirred at RT for 30 min and then diluted with DCM (15 mL), washed with water (15 mL), dried (Na$_2$SO$_4$) and evaporated. The resulting purple oil was dissolved in DCM (1 mL) and TFA (3 mL) was added. After stirring for 1 h the solution was loaded onto a 5 g SCX-2 cartridge. The column was flushed with methanol and then the product was eluted with 2M ammonia in methanol. Evaporation gave a purple residue which was dissolved in THF (2 mL). 4M aqueous lithium hydroxide (2 mL) was added and the mixture was stirred at RT for 30 min. The mixture was diluted with ethyl acetate (10 mL), washed with brine (10 mL), dried (Na$_2$SO$_4$) and evaporated. The crude product was purified by MDAP to give Example 1 as a white solid (24 mg).

LCMS (Method 1): Rt=1.67 min, m/z 408.1 [M+H]$^+$ $^1$H NMR (400 MHz, d6-DMSO) δ 11.37 (s, 1H), 7.98 (d, J=5.4 Hz, 1H), 7.22 (d, J=8.6 Hz, 2H), 7.13-7.09 (m, 1H), 7.05 (d, J=9.4 Hz, 2H), 6.23 (d, J=5.4 Hz, 1H), 3.64-3.53 (m, 1H), 3.44-3.36 (m, 1H), 3.29-3.18 (m, 2H), 3.13-3.04 (m, 1H), 2.81-2.65 (m, 3H), 2.59 (dd, J=5.5, 12.3 Hz, 1H), 2.32 (d, J=1.0 Hz, 3H), 2.29-2.20 (m, 2H), 2.08 (s, 3H), 1.95-1.87 (m, 1H), 1.68-1.61 (m, 1H), 1.39 (s, 2H).

Examples 2 to 18

Examples 2 to 18 were prepared in a similar manner of Example 1, substituting 1D-a and 1-methylpiperazine with the starting materials indicated.

| Ex | Structure | Starting materials | 1H NMR | LC-MS |
|---|---|---|---|---|
| 2 | 3-amino-1-(4-cyclopropylpiperazin-1-yl)-2-(4-((3-methyl-1H-pyrrolo[2,3-b]pyridin-4-yl)oxy)benzyl)propan-1-one | 1D-a and 1-cyclopropyl-piperazine | $^1$H NMR (400 MHz, d6-DMSO) δ 11.36 (s, 1H), 7.97 (d, J = 5.4 Hz, 1H), 7.23 (d, J = 9.5 Hz, 2H), 7.13-7.09 (m, 1H), 7.06 (d, J = 8.5 Hz, 2H), 6.23 (d, J = 5.4 Hz, 1H), 3.61-3.55 (m, 1H), 3.29-3.19 (m, 2H), 3.15-3.02 (m, 2H), 2.82-2.65 (m, 3H), 2.60 (dd, J = 5.8, 12.0 Hz, 1H), 2.48-2.39 (m, 2H), 2.30 (d, J = 1.0 Hz, 3H), 2.19-2.13 (m, 1H), 1.85-1.81 (m, 1H), 1.56 (s, 2H), 1.49-1.42 (m, 1H), 0.41-0.34 (m, 2H), 0.27 (d, J = 2.3 Hz, 2H). | Rt = 1.81 min, m/z 434.1 [M + H]$^+$ (Method 1) |
| 3 | 3-amino-2-(3-fluoro-4-((3-methyl-1H-pyrrolo[2,3-b]pyridin-4-yl)oxy)benzyl)-N-(1-methylpiperidin-4-yl)propanamide | 1D-e and 1-methyl-piperidin-4-amine | $^1$H NMR (400 MHz, DMSO) δ 11.39 (s, 1H), 7.96 (d, J = 5.4 Hz, 1H), 7.70 (dd, J = 7.4, 7.4 Hz, 1H), 7.23-7.18 (m, 2H), 7.14 (s, 1H), 7.04 (dd, J = 1.3, 8.2 Hz, 1H), 6.13 (d, J = 5.3 Hz, 1H), 3.51-3.43 (m, 2H), 3.13-3.04 (m, 1H), 2.78-2.53 (m, 6H), 2.47-2.41 (m, 1H), 2.37 (d, J = 1.0 Hz, 3H), 2.12-2.08 (m, 3H), 1.92-1.82 (m, 2H), 1.65-1.61 (m, 1H), 1.51-1.16 (m, 3H). | Rt = 1.75 min, m/z 440.2 [M + H]$^+$ (Method 1) |

-continued

| Ex | Structure | Starting materials | 1H NMR | LC-MS |
|---|---|---|---|---|
| 4 | 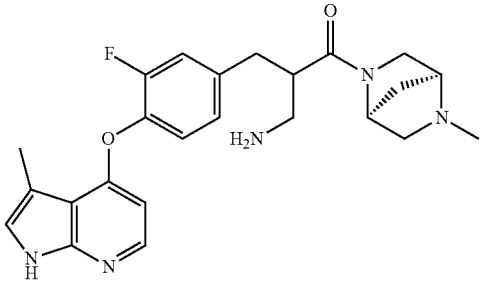 [SMILES: Cc1c[nH]c2nccc(Oc3ccc(CC(CN)C(=O)N4C[C@@H]5C[C@H]4CN5C)cc3F)c12]<br>3-amino-2-(3-fluoro-4-((3-methyl-1H-pyrrolo[2,3-b]pyridin-4-yl)oxy)benzyl)-1-((1S,4S)-5-methyl-2,5-diazabicyclo[2.2.1]heptan-2-yl)propan-1-one | 1D-e and (1S,4S)-2-methyl-2,5-diazabicyclo[2.2.1]heptane | $^1$H NMR (400 MHz, DMSO) δ 11.40 (s, 1H), 8.01-7.94 (m, 1H), 7.29-7.17 (m, 2H), 7.16-7.12 (m, 1H), 7.11-7.02 (m, 1H), 6.23-6.05 (m, 1H), 4.53-4.45 (m, 1H), 3.70-3.51 (m, 1H), 3.35-3.29 (m, 2H), 3.11-2.95 (m, 2H), 2.82-2.56 (m, 6H), 2.38 (s, 3H), 2.28-2.24 (m, 1H), 2.13-2.03 (m, 3H), 1.75-1.60 (m, 1H), 1.53-1.07 (m, 1H). | Rt = 1.72 min, m/z 438.1 [M + H]$^+$ (Method 1) |
| 5 | 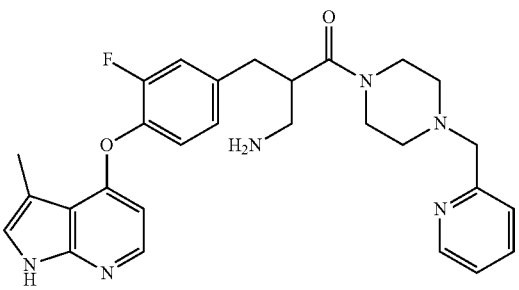 [SMILES: Cc1c[nH]c2nccc(Oc3ccc(CC(CN)C(=O)N4CCN(Cc5ccccn5)CC4)cc3F)c12]<br>3-amino-2-(3-fluoro-4-((3-methyl-1H-pyrrolo[2,3-b]pyridin-4-yl)oxy)benzyl)-1-(4-(pyridin-2-ylmethyl)piperazin-1-yl)propan-1-one | 1D-e and 1-(pyridin-2-yl-methyl)piperazine | $^1$H NMR (400 MHz, DMSO) δ 11.39 (s, 1H), 8.48 (dd, J = 0.9, 3.9 Hz, 1H), 8.01 (d, J = 5.4 Hz, 1H), 7.78-7.72 (m, 1H), 7.41 (d, J = 7.8 Hz, 1H), 7.27-7.20 (m, 3H), 7.14 (s, 1H), 7.05 (d, J = 8.4 Hz, 1H), 6.16 (d, J = 5.4 Hz, 1H), 3.64 (d, J = 15.2 Hz, 1H), 3.52 (d, J = 2.1 Hz, 2H), 3.50-3.39 (m, 2H), 3.21-3.05 (m, 2H), 2.85-2.67 (m, 3H), 2.63-2.54 (m, 2H), 2.42 (s, 2H), 2.39 (d, J = 1.0 Hz, 3H), 2.12-2.03 (m, 2H), 1.92-1.83 (m, 1H). | Rt = 1.96 min, m/z 503.2 [M + H]$^+$ (Method 1) |
| 6 | 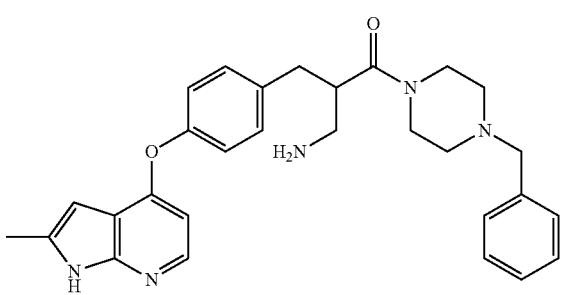 [SMILES: Cc1cc2c(Oc3ccc(CC(CN)C(=O)N4CCN(Cc5ccccc5)CC4)cc3)ccnc2[nH]1]<br>3-amino-1-(4-benzylpiperazin-1-yl)-2-(4-((2-methyl-1H-pyrrolo[2,3-b]pyridin-4-yl)oxy)benzyl)propan-1-one | 1D-d and 1-benzyl piperazine | $^1$H NMR (400 MHz, d6-DMSO) δ 11.55 (s, 1H), 7.96 (d, J = 5.4 Hz, 1H), 7.34-7.23 (m, 4H), 7.20 (d, J = 8.8 Hz, 2H), 7.03 (d, J = 8.6 Hz, 2H), 6.39 (d, J = 5.4 Hz, 1H), 5.85 (d, J = 1.0 Hz, 1H), 3.54-3.35 (m, 7H), 3.12-3.04 (m, 1H), 2.80-2.65 (m, 3H), 2.59 (dd, J = 5.4, 12.2 Hz, 1H), 2.33 (s, 3H), 2.29-2.22 (m, 2H), 2.12-2.07 (m, 1H), 1.90-1.84 (m, 1H), 1.58 (s, 2H). | Rt = 1.99 min, m/z 484.1 [M + H]$^+$ (Method 1) |

-continued

| Ex | Structure | Starting materials | 1H NMR | LC-MS |
|---|---|---|---|---|
| 7 | 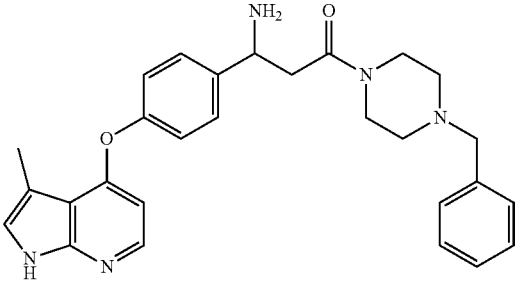 [SMILES: Cc1c[nH]c2nccc(Oc3ccc(C(N)CC(=O)N4CCN(Cc5ccccc5)CC4)cc3)c12]<br>3-amino-1-(4-benzylpiperazin-1-yl)-3-(4-((3-methyl-1H-pyrrolo[2,3-b]pyridin-4-yl)oxy)phenyl)propan-1-one | 1D-c and 1-benzyl-piperazine | $^1$H NMR (400 MHz, d6-DMSO) δ 11.36 (s, 1H), 8.00 (d, J = 5.4 Hz, 1H), 7.45 (d, J = 8.6 Hz, 2H), 7.36-7.22 (m, 5H), 7.14-7.10 (m, 1H), 7.08 (d, J = 8.3 Hz, 2H), 6.24 (d, J = 5.4 Hz, 1H), 4.25 (t, J = 6.6 Hz, 1H), 3.47-3.43 (m, 2H), 3.44-3.34 (m, 4H), 2.60-2.54 (m, 2H), 2.33 (d, J = 1.0 Hz, 3H), 2.31-2.12 (m, 4H), 1.99 (s, 2H). | Rt = 1.90 min, m/z 470.2 [M + H]$^+$ (Method 1) |
| 8 | 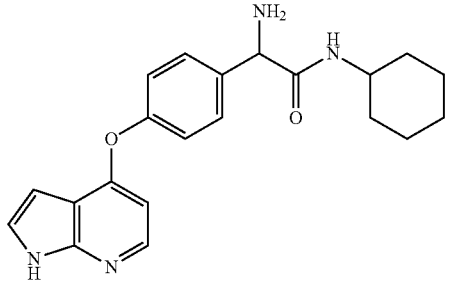 [SMILES: NC(C(=O)NC1CCCCC1)c1ccc(Oc2ccnc3[nH]ccc23)cc1]<br>2-(4-((1H-pyrrolo[2,3-b]pyridin-4-yl)oxy)phenyl)-2-amino-N-cyclohexylacetamide | 1D-b and cyclohexyl amine | $^1$H NMR (400 MHz, d6-DMSO) δ 11.72 (s, 1H), 8.08 (d, J = 5.4 Hz, 1H), 7.90 (d, J = 8.1 Hz, 1H), 7.45 (d, J = 8.5 Hz, 2H), 7.33 (dd, J = 2.5, 3.3 Hz, 1H), 7.12 (d, J = 8.6 Hz, 2H), 6.40 (d, J = 5.4 Hz, 1H), 6.16 (dd, J = 1.9, 3.5 Hz, 1H), 4.35 (s, 1H), 3.57-3.48 (m, 1H), 2.32 (s, 2H), 1.78-1.60 (m, 3H), 1.59-1.50 (m, 1H), 1.30-1.11 (m, 6H). | Rt = 2.44 min, m/z 365.1 [M + H]$^+$ (Method 1) |
| 9 | 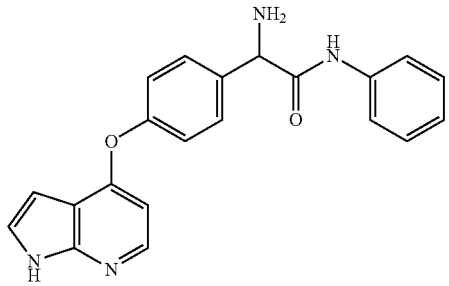 [SMILES: NC(C(=O)Nc1ccccc1)c1ccc(Oc2ccnc3[nH]ccc23)cc1]<br>2-(4-((1H-pyrrolo[2,3-b]pyridin-4-yl)oxy)phenyl)-2-amino-N-phenylacetamide | 1D-b and aniline | $^1$H NMR (400 MHz, d6-DMSO) δ 11.72 (s, 1H), 10.12 (s, 1H), 8.07 (d, J = 5.4 Hz, 1H), 7.65 (dd, J = 4.3, 4.3 Hz, 2H), 7.55 (d, J = 8.6 Hz, 2H), 7.35-7.29 (m, 3H), 7.17-7.14 (m, 2H), 7.07-7.03 (m, 1H), 6.40 (d, J = 5.4 Hz, 1H), 6.22-6.19 (m, 1H), 4.58 (s, 1H), 3.02-2.61 (s, 2H). | Rt = 2.31 min, m/z 359.2 [M + H]$^+$ (Method 3) |

-continued

| Ex | Structure | Starting materials | 1H NMR | LC-MS |
|---|---|---|---|---|
| 10 | 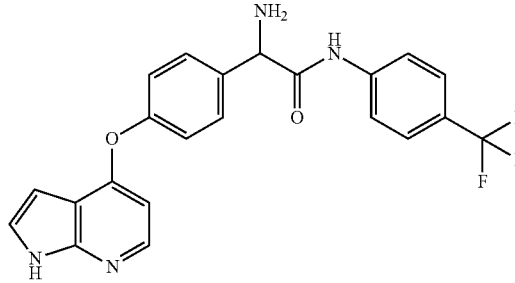<br>2-(4-((1H-pyrrolo[2,3-b]pyridin-4-yl)oxy)phenyl)-2-amino-N-(4-(trifluoromethyl)phenyl)-acetamide | 1D-b and 4-(trifluoromethyl)-aniline | $^1$H NMR (400 MHz, d6-DMSO) δ 11.73 (s, 1H), 8.07 (d, J = 5.4 Hz, 1H), 7.87 (d, J = 8.4 Hz, 2H), 7.68 (d, J = 8.6 Hz, 2H), 7.56 (d, J = 8.6 Hz, 2H), 7.35-7.33 (m, 1H), 7.17-7.14 (m, 2H), 6.40 (d, J = 5.4 Hz, 1H), 6.20 (dd, J = 2.0, 3.5 Hz, 1H), 4.62 (s, 1H), 3.40-3.22 (s, 2H). | Rt = 2.83 min, m/z 427.2 [M + H]$^+$ (Method 3) |
| 11 | 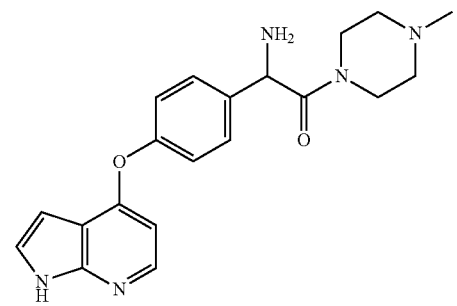 [SMILES: CN1CCN(C(=O)C(N)c2ccc(Oc3ccnc4[nH]ccc34)cc2)CC1]<br>2-(4-((1H-pyrrolo[2,3-b]pyridin-4-yl)oxy)phenyl)-2-amino-1-(4-methylpiperazin-1-yl)ethanone | 1D-b and 1-methyl-piperazine | $^1$H NMR (400 MHz, d6-(DMSO) δ 11.73 (s, 1H), 8.08 (d, J = 5.4 Hz, 1H), 7.40-7.37 (m, 2H), 7.33 (dd, J = 2.5, 3.3 Hz, 1H), 7.14 (d, J = 8.6 Hz, 2H), 6.42 (d, J = 5.3 Hz, 1H), 6.14 (dd, J = 1.8, 3.4 Hz, 1H), 4.87 (s, 1H), 3.65-3.56 (m, 1H), 3.50-3.36 (m, 3H), 2.34-2.23 (m, 3H), 2.20-2.14 (m, 1H), 2.11 (s, 3H), 2.10-2.07 (m, 1H), 1.88-1.80 (m, 1H). | Rt = 2.66 min, m/z 366.2 [M + H]$^+$ (Method 2) |
| 12 | 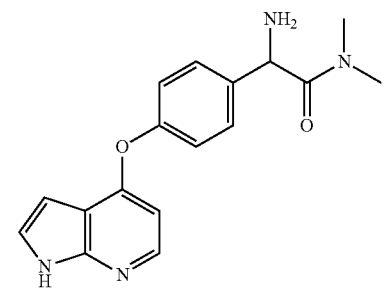 [SMILES: CN(C)C(=O)C(N)c1ccc(Oc2ccnc3[nH]ccc23)cc1]<br>2-(4-((1H-pyrrolo[2,3-b]pyridin-4-yl)oxy)phenyl)-2-amino-N,N-dimethylacetamide | 1D-b and dimethyl-amine | $^1$H NMR (400 MHz, d6-DMSO) δ 11.75 (s, 1H), 8.10 (d, J = 5.4 Hz, 1H), 7.42 (d, J = 8.6 Hz, 2H), 7.36 (dd, J = 2.5, 3.3 Hz, 1H), 7.17 (d, J = 8.7 Hz, 2H), 6.43 (d, J = 5.4 Hz, 1H), 6.18 (dd, J = 1.7, 3.4 Hz, 1H), 5.01 (s, 1H), 3.94 (s, 2H), 2.91 (s, 3H), 2.88 (s, 3H). | Rt = 1.71 min, m/z 311.1 [M + H]$^+$ (Method 3) |

| Ex | Structure | Starting materials | 1H NMR | LC-MS |
|---|---|---|---|---|
| 13 | 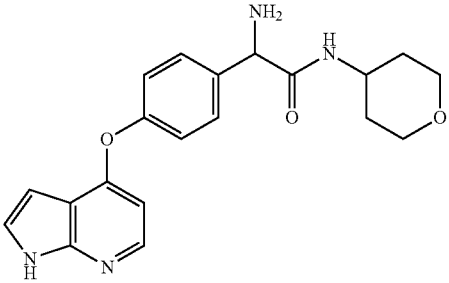 [SMILES: NC(C(=O)NC1CCOCC1)c1ccc(Oc2ccnc3[nH]ccc23)cc1]<br>2-(4-((1H-pyrrolo[2,3-b]pyridin-4-yl)oxy)phenyl)-2-amino-N-(tetrahydro-2H-pyran-4-yl)acetamide | 1D-b and 4-aminotetrahydropyran | $^1$H NMR (400 MHz, d6-DMSO) δ 11.74 (s, 1H), 8.21 (s, 1H), 8.13-8.07 (m, 2H), 7.47 (d, J = 8.6 Hz, 2H), 7.34 (dd, J = 2.5, 3.3 Hz, 1H), 7.14 (d, J = 8.7 Hz, 2H), 6.41 (d, J = 5.4 Hz, 1H), 6.16 (dd, J = 1.9, 3.4 Hz, 1H), 4.43-4.41 (m, 1H), 3.79-3.79 (m, 4H), 3.39-3.28 (m, 2H), 1.73-1.59 (m, 2H), 1.51-1.33 (m, 2H). | Rt = 1.73 min, m/z 367.2 [M + H]$^+$ (Method 3) |
| 14 | 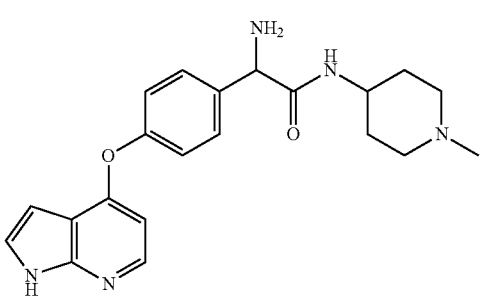 [SMILES: CN1CCC(NC(=O)C(N)c2ccc(Oc3ccnc4[nH]ccc34)cc2)CC1]<br>2-(4-((1H-pyrrolo[2,3-b]pyridin-4-yl)oxy)phenyl)-2-amino-N-(1-methylpiperidin-4-yl)acetamide | 1D-b and 1-methylpiperidin-4-amine | $^1$H NMR (400 MHz, d6-DMSO) δ 11.74 (s, 1H), 8.08 (d, J = 5.4 Hz, 1H), 7.96 (d, J = 7.9 Hz, 1H), 7.45 (d, J = 8.5 Hz, 2H), 7.35-7.32 (m, 1H), 7.12 (d, J = 8.6 Hz, 2H), 6.40 (d, J = 5.4 Hz, 1H), 6.17 (dd, J = 1.7, 3.4 Hz, 1H), 4.35 (s, 1H), 3.55-3.43 (m, 1H), 2.71-2.60 (m, 2H), 2.24 (s, 2H), 2.13 (s, 3H), 1.97-1.86 (m, 2H), 1.74-1.60 (m, 2H), 1.50-1.34 (m, 2H). | Rt = 3.20 min, m/z 380.2 [M + H]$^+$ (Method 1) |
| 15 | 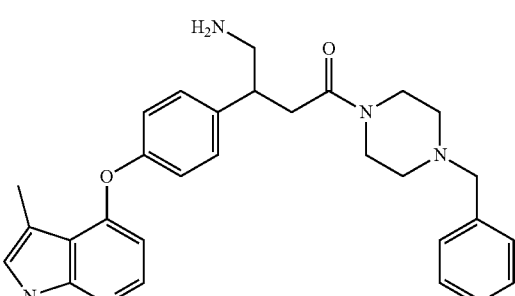<br>4-amino-1-(4-benzylpiperazin-1-yl)-3-(4-((3-methyl-1H-pyrrolo[2,3-b]pyridin-4-yl)oxy)phenyl)butan-1-one | 1D-f and 1-benzylpiperazine | $^1$H NMR (400 MHz, DMSO) δ 11.36 (s, 1H), 7.99 (d, J = 5.4 Hz, 1H), 7.35-7.21 (m, 7H), 7.13-7.10 (m, 1H), 7.07 (d, J = 8.6 Hz, 2H), 6.25 (d, J = 5.4 Hz, 1H), 3.45-3.38 (m, 6H), 3.09-3.00 (m, 1H), 2.77-2.68 (m, 3H), 2.60 (dd, J = 8.5, 15.3 Hz, 1H), 2.33 (d, J = 1.0 Hz, 3H), 2.31-2.26 (m, 2H), 2.17-2.11 (m, 2H), 1.58 (s, 2H). | Rt = 1.96 min, m/z 484.2 [M + H]$^+$ (Method 1) |

| Ex | Structure | Starting materials | 1H NMR | LC-MS |
|---|---|---|---|---|
| 16 | 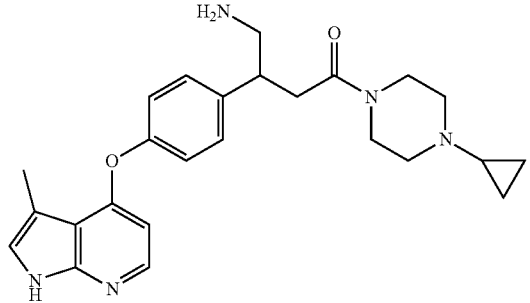 [SMILES: Cc1c[nH]c2nccc(Oc3ccc(C(CN)CC(=O)N4CCN(C5CC5)CC4)cc3)c12]<br>4-amino-1-(4-cyclopropylpiperazin-1-yl)-3-(4-((3-methyl-1H-pyrrolo[2,3-b]pyridin-4-yl)oxy)phenyl)butan-1-one | 1D-f and 1-cyclopropyl piperazine | $^1$H NMR (400 MHz, DMSO) δ 11.35 (s, 1H), 7.98 (d, J = 5.4 Hz, 1H), 7.29 (d, J = 8.6 Hz, 2H), 7.13-7.10 (m, 1H), 7.07 (d, J = 8.6 Hz, 2H), 6.26 (d, J = 5.4 Hz, 1H), 3.45-3.30 (m, 5H), 3.10-3.01 (m, 1H), 2.79-2.68 (m, 3H), 2.61 (dd, J = 8.5, 15.1 Hz, 1H), 2.48-2.39 (m, 2H), 2.33-2.31 (m, 3H), 2.30-2.21 (m, 2H), 1.58-1.51 (m, 2H), 0.43-0.37 (m, 2H), 0.33-0.27 (m, 2H). | Rt = 1.65 min, m/z 434.1 [M + H]$^+$ (Method 1) |
| 17 | 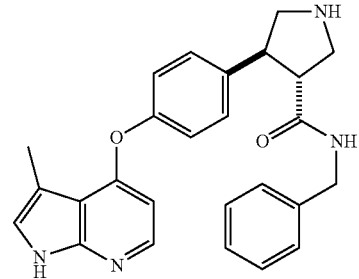<br>rac-(3R,4S)-N-benzyl-4-(4-((3-methyl-1H-pyrrolo[2,3-b]pyridin-4-yl)oxy)phenyl)pyrrolidine-3-carboxamide | 1D-g and benzyl-amine | $^1$H NMR (400 MHz, DMSO) δ 11.39 (s, 1H), 8.38 (t, J = 5.9 Hz, 1H), 7.98 (d, J = 5.4 Hz, 1H), 7.35-7.18 (m, 6H), 7.14-7.06 (m, 5H), 6.24 (d, J = 5.4 Hz, 1H), 4.34 (dd, J = 6.4, 15.3 Hz, 1H), 4.15 (dd, J = 5.5, 15.3 Hz, 1H), 3.47-3.41 (m, 1H), 3.28 (dd, J = 7.9, 11.0 Hz, 1H), 3.20 (dd, J = 8.2, 10.2 Hz, 1H), 2.99-2.85 (m, 2H), 2.80-2.72 (m, 1H), 2.33 (d, J = 1.0 Hz, 3H). | Rt = 2.49 min, m/z 427.3 [M + H]$^+$ (Method 1) |
| 18 | 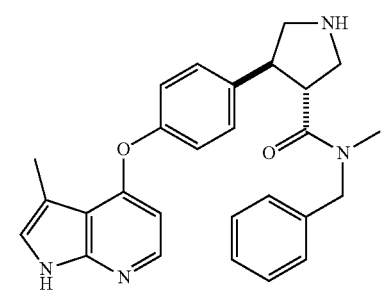<br>rac-(3R,4S)-N-benzyl-N-methyl-4-(4-((3-methyl-1H-pyrrolo[2,3-b]pyridin-4-yl)oxy)phenyl)-pyrrolidine-3-carboxamide | 1D-g and N-methyl-1-phenyl-methan-amine | $^1$H NMR (400 MHz, DMSO) δ 11.37 (s, 1H), 8.02-7.97 (m, 1H), 7.39-7.21 (m, 5H), 7.14-6.93 (m, 5H), 6.22 (d, J = 5.4 Hz, 1H), 4.64-4.55 (m, 1H), 4.45-4.34 (m, 1H), 3.80-3.49 (m, 2H), 3.28-3.16 (m, 2H), 3.00-2.79 (m, 2H), 2.79-2.76 (m, 3H), 2.76-2.69 (m, 1H), 2.33-2.29 (m, 3H). | Rt = 2.61 min, m/z 441.3 [M + H]$^+$ (Method 1) |

| Ex | Structure | Starting materials | 1H NMR | LC-MS |
|---|---|---|---|---|
| 19 | 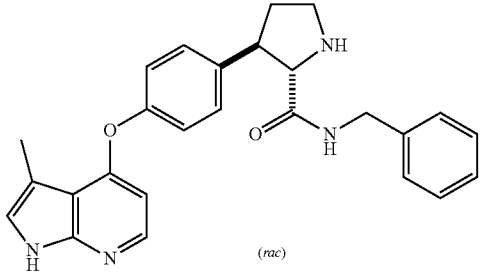 [SMILES: Cc1c[nH]c2nccc(Oc3ccc([C@H]4CCN[C@@H]4C(=O)NCc4ccccc4)cc3)c12]<br>rac-(2S,3R)-N-benzyl-3-(4-((3-methyl-1H-pyrrolo[2,3-b]pyridin-4-yl)oxy)phenyl)pyrrolidine-2-carboxamide | 1D-h and benzyl-amine | $^1$H NMR (400 MHz, DMSO-d$_6$) δ 11.35 (br. s., 1 H), 8.51 (s, 1 H), 8.15 (s, 1 H), 7.99 (d, J = 5.7 Hz, 1H), 6.94-7.50 (m, 10 H), 6.25 (d, J = 5.3 Hz, 1 H), 4.07-4.48 (m, 2 H), 3.69 (m, 2 H), 3.24-3.36 (m, 4 H), 2.87-3.21 (m, 2 H), 2.33 (s, 3 H), 2.23 (dd, J = 12.1, 5.0 Hz, 1 H), 1.75-1.97 (m, 1 H). | Rt = 0.51 min, m/z 427.2 [M − H]+ (Method 8) |
| 20 | 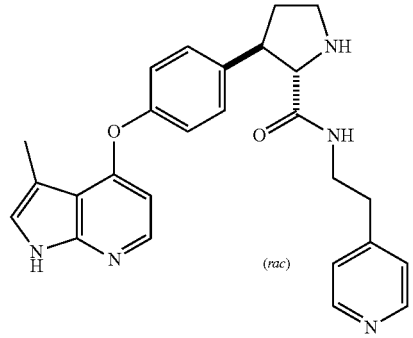 [SMILES: Cc1c[nH]c2nccc(Oc3ccc([C@H]4CCN[C@@H]4C(=O)NCCc4ccncc4)cc3)c12]<br>rac-(2S,3R)-3-(4-((3-methyl-1H-pyrrolo[2,3-b]pyridin-4-yl)oxy)phenyl)-N-(2-(pyridin-4-yl)ethyl)pyrrolidine-2-carboxamide | 1D-h and 2-(pyridin-4-yl)ethane-1-amine | $^1$H-NMR (400 MHz, DMSO-d6) δ 11.33 (bs, 1H), 8.47-8.37 (m, 2H), 8.21-8.12 (m, 1H), 8.05-7.94 (m, 2H), 7.34-7.24 (m, 2H), 7.20-7.12 (m, 2H), 7.11-7.09 (m, 1H), 7.08-7.03 (m, 2H), 6.28-6.21 (m, 2H), 3.48 (d, 1H, J = 6.4 Hz), 3.38-3.31 (m, 1H), 3.20-3.13 (m, 1H), 3.08-2.99 (m, 1H), 2.83-2.76 (m, 1H), 2.73 (t, 2H, J = 6.9 Hz), 2.32 (d, 3H, J = 0.7 Hz), 2.12-2.02 (m, 1H), 1.75-1.65 (m, 1H). | Rt = 0.30 min, m/z 442.3 [M − H]+ (Method 8) |
| 21 | 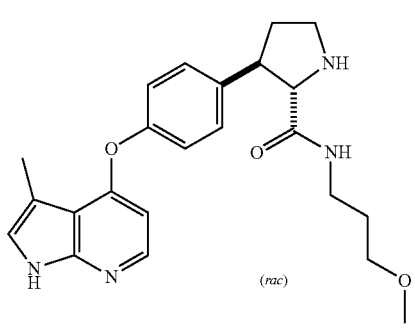 [SMILES: COCCCNC(=O)[C@H]1NCC[C@@H]1c1ccc(Oc2ccnc3[nH]cc(C)c23)cc1]<br>rac-(2S,3R)-N-(3-methoxypropyl)-3-(4-((3-methyl-1H-pyrrolo[2,3-b]pyridin-4-yl)oxy)phenyl)pyrrolidine-2-carboxamide | 1D-h and 3-methoxy-propan-1-amine | $^1$H NMR (400 MHz, DMSO-d$_6$) δ 11.34 (br. s., 1 H), 7.87-8.06 (m, 2 H), 7.37 (d, J = 8.3 Hz, 2 H), 6.99-7.22 (m, 3 H), 6.26 (d, J = 5.7 Hz, 1 H), 3.51 (d, J = 6.6 Hz, 1 H), 3.21-3.29 (m, 6 H), 3.01-3.18 (m, 4 H), 2.82-2.97 (m, 1 H), 2.33 (s, 3 H), 2.16 (d, J = 7.0 Hz, 1 H), 1.78 (dd, J = 12.1, 8.1 Hz, 1 H), 1.61 (t, J = 6.4 Hz, 2 H). | Rt = 0.41 min, m/z 409.2 [M − H]+ (Method 8) |

| Ex | Structure | Starting materials | 1H NMR | LC-MS |
|----|-----------|-------------------|--------|-------|
| 22 | rac-(2S,3R)-3-(4-((3-methyl-1H-pyrrolo[2,3-b]pyridin-4-yl)oxy)phenyl)-N-phenethylpyrrolidine-2-carboxamide | 1D-h and 2-phenyl-ethan-1-amine | $^1$H NMR (400 MHz, DMSO-d$_6$) δ ppm 11.34 (br. s., 1 H), 8.17 (s, 1 H), 7.91-8.05 (m, 2 H), 6.87-7.45 (m, 10 H), 6.26 (d, J = 5.3 Hz, 1 H), 3.51 (d, J = 6.4 Hz, 1 H), 3.14-3.27 (m, 3 H), 2.99-3.14 (m, 1 H), 2.82 (dt, J = 10.7, 7.2 Hz, 1 H), 2.71 (t, J = 7.3 Hz, 2 H), 2.28 (s, 3 H), 1.97-2.24 (m, 1 H), 1.61-1.84 (m, 1 H). | Rt = 0.54 min, m/z 441.1 [M − H]+ (Method 8) |
| 23 | rac-(2S,3R)-3-(4-((3-methyl-1H-pyrrolo[2,3-b]pyridin-4-yl)oxy)phenyl)-N-(2-phenoxyethyl)pyrrolidine-2-carboxamide | 1D-h and 2-phenoxy-ethan-1-amine | $^1$H NMR (400 MHz, DMSO-d6) δ 11.72 (br. s., 1 H), 10.07 (br. s., 1 H), 8.94 (br. s., 1 H), 8.58 (t, J = 5.5 Hz, 1 H), 8.07 (d, J = 6.0 Hz, 1 H), 7.42 (d, J = 8.6 Hz, 2 H), 7.16-7.28 (m, 3 H), 7.09 (d, J = 8.6 Hz, 2 H), 6.79-6.94 (m, 3 H), 6.34 (d, J = 5.7 Hz, 1 H), 4.02-4.16 (m, 1 H), 3.95 (t, J = 5.4 Hz, 2 H), 3.53-3.66 (m, 5 H), 2.28-2.47 (m, 4 H), 2.01-2.23 (m, 1H). | Rt = 0.53 min, m/z 457.1 [M − H]+ (Method 8) |
| 24 | rac-(2S,3R)-3-(4-((3-methyl-1H-pyrrolo[2,3-b]pyridin-4-yl)oxy)phenyl)-N-(tetrahydro-2H-pyran-4-yl)pyrrolidine-2-carboxamide | 1D-h and tetrahydro-2H-pyran-4-amine | $^1$H-NMR (400 MHz, DMSO-d6) δ 11.34 (bs, 1H), 8.17 (s, 1H), 7.99 (d, 1H, J = 5.5 Hz), 7.83 (d, 1H, J = 7.9 Hz), 7.35 (d, 2H, J = 8.6 Hz), 7.11 (s, 1H), 7.07 (d, 2H, J = 8.6 Hz), 6.25 (d, 1H, J = 5.3 Hz), 3.82-3.70 (m, 3H), 3.48 (d, 1H, J = 6.8 Hz), 3.10-3.03 (m, 1H), 2.98-2.90 (m, 1H), 2.32 (s, 3H), 2.32-2.28 (m, 1H), 2.20-2.11 (m, 1H), 1.85-1.75 (m, 1H), 1.68-1.57 (m, 2H), 1.48-1.30 (m, 2H). | Rt = 0.40 min, m/z 421.4 [M − H]+ (Method 8) |

| Ex | Structure | Starting materials | 1H NMR | LC-MS |
|---|---|---|---|---|
| 25 | 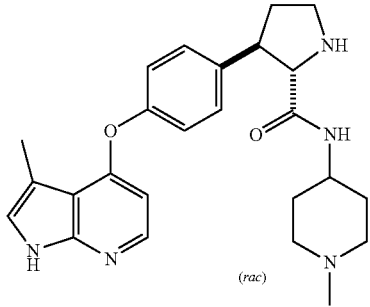 [SMILES: Cc1c[nH]c2nccc(Oc3ccc([C@H]4CCN[C@@H]4C(=O)NC4CCN(C)CC4)cc3)c12]<br>rac-(2S,3R)-3-(4-((3-methyl-1H-pyrrolo[2,3-b]pyridin-4-yl)oxy)phenyl)-N-(1-methylpiperidin-4-yl)pyrrolidine-2-carboxamide | 1D-h and 1-methylpiperidin-4-amine | $^1$H-NMR (400 MHz, DMSO-d6) δ 11.35 (bs, 1H), 8.18 (s, 2H), 8.02-7.96 (m, 1H), 7.80 (d, 1H, J = 7.9 Hz), 7.35 (d, 2H, J = 8.1 Hz), 7.12 (s, 1H), 7.08 (d, 2H, J = 8.1 Hz), 6.29-6.21 (m, 1H), 3.53-3.48 (m, 2H), 3.27-3.18 (m, 2H), 3.13-3.05 (m, 1H), 3.01-2.91 (m, 1H), 2.73-2.62 (m, 2H), 2.32 (s, 3H), 2.17 (s, 3H), 2.09-1.96 (m, 2H), 1.88-1.76 (m, 2H), 1.73-1.57 (m, 2H), 1.51-1.30 (m, 2H). | Rt = 0.25 min, m/z 434.3 [M − H]+ (Method 8) |
| 26 | 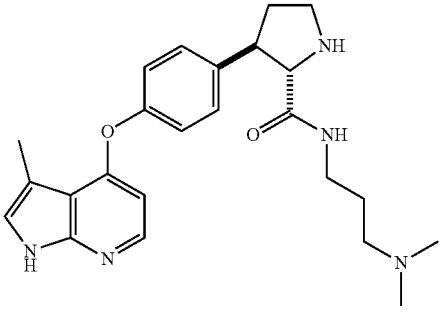<br>rac-(2R,3S)-N-(3-(dimethylamino)propyl)-3-(4-((3-methyl-1H-pyrrolo[2,3-b]pyridin-4-yl)oxy)phenyl)pyrrolidine-2-carboxamide | 1D-h and N1,N1-dimethyl-propane-1,3-diamine | $^1$H-NMR (400 MHz, DMSO-d6) δ 11.36 (bs, 1H), 8.18 (s, 2H), 8.07-7.97 (m, 2H), 7.37 (d, 2H, J = 7.7 Hz), 7.12 (s, 1H), 7.08 (d, 2H, J = 7.7 Hz), 6.30-6.23 (m, 1H), 3.52 (d, 1H, J = 6.1 Hz), 3.28-3.20 (m, 2H), 3.14-3.03 (m, 3H), 2.97-2.87 (m, 1H), 2.33 (s, 3H), 2.27-2.21 (m, 2H), 2.16 (s, 6H), 1.84-1.73 (m, 1H), 1.52 (m, 2H). | Rt = 0.24 min, m/z 422.4 [M − H]+ (Method 8) |

Example 27

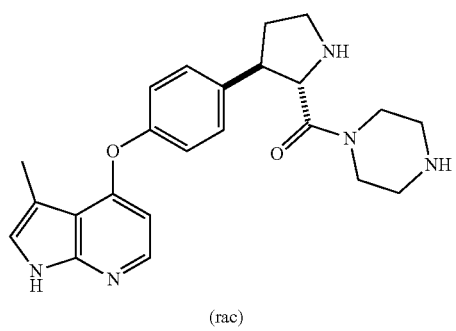

rac-((2S,3R)-(3-(4-((3-methyl-1H-pyrrolo[2,3-b]pyridin-4-yl)oxy)phenyl)pyrrolidin-2-yl)(piperazin-1-yl)methanone (Example 27)

Intermediate 1D-h (400 mg, 0.71 mmol), benzyl piperazine-1-carboxylate (310 mg, 1.41 mmol) and COMU (362 mg, 0.85 mmol) were dissolved in DCM (10 mL) and DIPEA (0.27 mL, 1.55 mmol) was added. The reaction was stirred at RT for 60 min and then diluted with ethyl acetate, washed with aqueous 0.5M HCl, aqueous sat NaHCO$_3$, brine and dried (Na$_2$SO$_4$). The crude product was chromatographed on a Si cartridge eluting with 0-100% ethyl acetate in hexane. The resulting oil was dissolved in 5 mL of MeOH and then formic acid (73 mg, 1.6 mmol), triethylsilane (615 mg, 5.30 mmol) and palladium on charcoal 5% (56 mg, 0.03 mmol) were added. The mixture was stirred at RT until complete debenzylation was observed, filtered and the filtrate dried under reduced pressure.

The resulting oil was dissolved in DCM (1 mL) and TFA (3 mL) was added. After stirring for 1 h the solution was dried and treated with THF/aqueous NaOH 4M 3:1 for 30 min, then the reaction mixture was neutralized with aqueous HCl and dried. The crude product was chromatographed on a Si cartridge eluting with 0-100% A to B (A: 95/5 water/MeCN+0.1% formic acid; B: 5/95 water/MeCN+0.1% formic acid) to give the desired product as a white powder (25 mg).

LCMS (Method 8): Rt=0.13 min, m/z 406.0 [M+H]+
$^1$H NMR (400 MHz, DMSO-d6) δ 11.37 (br. s., 1H), 8.15 (s, 1H), 8.03 (d, J=5.3 Hz, 1H), 7.43 (d, J=8.3 Hz, 2H), 6.98-7.22 (m, 3H), 6.27 (d, J=5.3 Hz, 1H), 4.25 (d, J=7.9 Hz, 1H), 2.95-3.68 (m, 9H), 2.60-2.92 (m, 3H), 2.40 (d, J=7.9 Hz, 1H), 2.31 (s, 3H), 1.84-2.04 (m, 1H).

Intermediate 28A-a

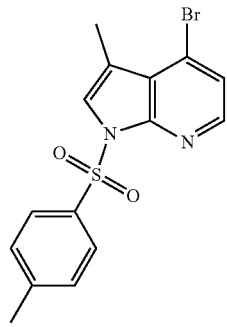 [SMILES: Cc1ccc(S(=O)(=O)n2cc(C)c3c(Br)ccnc32)cc1]

4-Bromo-3-methyl-1-tosyl-1H-pyrrolo[2,3-b]pyridine (Intermediate 28A-a)

4-Bromo-3-methyl-1H-pyrrolo[2,3-b]pyridine (2.0 g, 9.48 mmol) was dissolved in DMF (30 mL) and the solution was stirred at RT under a nitrogen stream. Sodium hydride (60% on mineral oil, 492 mg, 12.3 mmol) was added portion wise and the reaction was stirred for 30 min. A solution of 4-toluenesulfonyl chloride (1.90 g, 10.42 mmol) in DMF (10 mL) was added dropwise and the reaction was stirred for a further 30 min. The reaction mixture was carefully poured into cold water (100 mL) and stirred for 30 min. The product was extracted into ethyl acetate (2×70 mL) and the combined extracts were washed with brine (50 mL), dried (Na$_2$SO$_4$) and evaporated. The crude material was chromatographed on a 25 g Si cartridge eluting with 0-25% ethyl acetate in cyclohexane. The product was obtained as a white solid (1.80 g).

LCMS (Method 5): Rt=1.71 min, m/z 365.0/367.0 [M+H]$^+$

Preparation of Intermediate 28A-b

The following intermediate was prepared in a similar manner to Intermediate 28A-a by replacing 4-bromo-3-methyl-1H-pyrrolo[2,3-b]pyridine with the indicated starting materials.

| Intermediate | Structure | Starting materials | LC-MS |
|---|---|---|---|
| 28A-b | (4-bromo-1-tosyl-1H-pyrrolo[2,3-b]pyridine structure) | 4-Bromo-1H-pyrrolo[2,3-b]pyridine | Rt = 1.59 min, m/z 351.1/353.1 [M + H]$^+$ (Method 5) |

Preparation of Intermediates from 28B-a to 28B-c

The following intermediates were prepared in a similar manner to Intermediate 1C-a from the indicated starting materials.

| Intermediate | Structure | Starting materials | LC-MS |
|---|---|---|---|
| 28B-a | (structure) | 28A-a and 1A-b | Rt = 2.04 min, m/z 612.3 [M + H]+ (Method 4) |

-continued

| Intermediate | Structure | Starting materials | LC-MS |
|---|---|---|---|
| 28B-b | 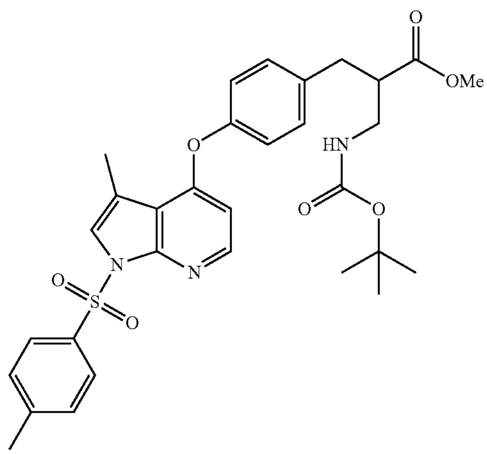 [SMILES: COC(=O)C(CNC(=O)OC(C)(C)C)Cc1ccc(Oc2ccnc3c2c(C)cn3S(=O)(=O)c2ccc(C)cc2)cc1] | 28A-a and 1A-a | Rt = 1.77 min, m/z 594.3 [M + H]⁺ (Method 5) |
| 28B-c | 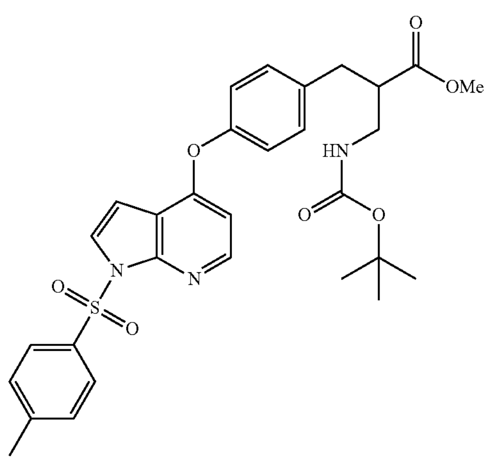 [SMILES: COC(=O)C(CNC(=O)OC(C)(C)C)Cc1ccc(Oc2ccnc3c2ccn3S(=O)(=O)c2ccc(C)cc2)cc1] | 28A-b and 1A-a | Rt = 1.69 min, m/z 580.3 [M + H]⁺ (Method 5) |

Intermediate 28C-a

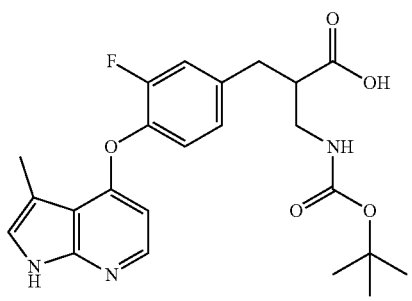 [SMILES: Cc1c[nH]c2nccc(Oc3ccc(CC(CNC(=O)OC(C)(C)C)C(=O)O)cc3F)c12]

3-((tert-Butoxycarbonyl)amino)-2-(3-fluoro-4-((3-methyl-1H-pyrrolo[2,3-b]pyridin-4-yl)oxy)benzyl) propanoic acid (Intermediate 28C-a)

Intermediate 28B-a (802 mg, 1.31 mmol) was heated at 65° C. in a mixture of methanol (10 mL) and 2M aqueous lithium hydroxide (2 mL) for 2.5 h. After allowing to cool, the methanol was evaporated and the pH was adjusted to pH 5 by the addition of 1M HCl. The product was extracted into DCM (20 mL). The extract was dried (Na$_2$SO$_4$) and evaporated to give a cream solid (602 mg).

LCMS (Method 4): Rt=1.49 min, m/z 444.3 [M+H]⁺

Preparation of Intermediates 28C-b and 28C-c

The following intermediates were prepared in a similar manner to Intermediate 28C-a from the indicated starting materials.

| Intermediate | Structure | Starting materials | LC-MS |
|---|---|---|---|
| 28C-b | 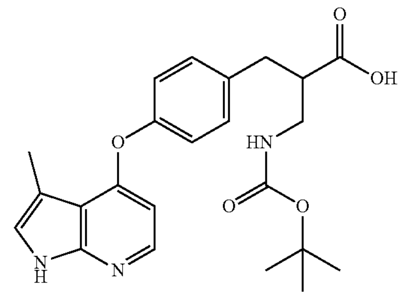 [SMILES: Cc1c[nH]c2nccc(Oc3ccc(CC(CNC(=O)OC(C)(C)C)C(=O)O)cc3)c12] | 28B-b | Rt = 1.13 min, m/z 426.2 [M + H]+ (Method 5) |
| 28C-c | 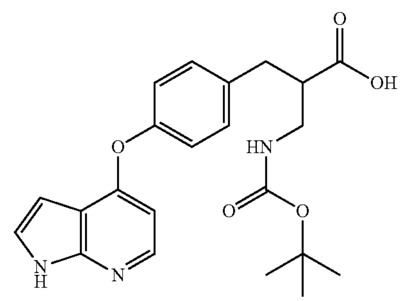 [SMILES: CC(C)(C)OC(=O)NCC(Cc1ccc(Oc2ccnc3[nH]ccc23)cc1)C(=O)O] | 28B-c | Rt = 1.08 min, m/z 412.3 [M + H]+ (Method 5) |

Example 28

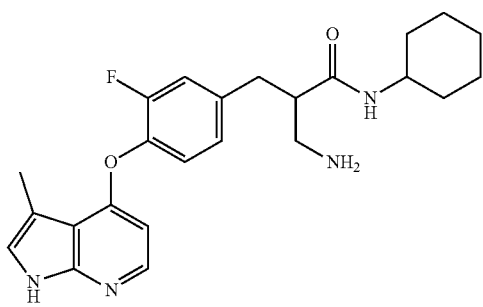 [SMILES: Cc1c[nH]c2nccc(Oc3ccc(CC(CN)C(=O)NC4CCCCC4)cc3F)c12]

3-amino-N-cyclohexyl-2-(3-fluoro-4-((3-methyl-1H-pyrrolo[2,3-b]pyridin-4-yl)oxy)benzyl)propanamide (Example 28)

Intermediate 28C-a (290 mg, 0.65 mmol), cyclohexylamine (71 mg, 0.72 mmol) and COMU (336 mg, 0.74 mmol) were dissolved in DCM (10 mL) and DIPEA (148 µL, 0.85 mmol) was added. The reaction was stirred at RT for 14 h and then evaporated to dryness. The residue was dissolved in DCM (10 mL) and TFA (2 mL) was added. The solution was stirred at RT for 1 h and then concentrated in vacuo. The residue was dissolved in a small amount of methanol and loaded onto a 5 g SCX-2 cartridge. The cartridge was flushed with methanol and then the basic product was eluted with 2M ammonia in methanol. Evaporation gave a crude product which was purified by MDAP to give a white solid (81 mg).

LCMS (Method 1) Rt=2.68 min, m/z 425.2 [M+H]+

$^1$H NMR (400 MHz, d6-DMSO) δ 11.40 (s, 1H), 7.96 (d, J=5.4 Hz, 1H), 7.67 (d, J=8.0 Hz, 1H), 7.25-7.17 (m, 2H), 7.13 (s, 1H), 7.05 (dd, J=1.3, 8.3 Hz, 1H), 6.12 (d, J=5.4 Hz, 1H), 3.57-3.46 (m, 1H), 2.76-2.68 (m, 3H), 2.59 (dd, J=5.6, 12.5 Hz, 1H), 2.48-2.43 (m, 1H), 2.38 (d, J=1.0 Hz, 3H), 1.72-1.45 (m, 6H), 1.26-0.92 (m, 6H).

Preparation of Examples 29 to 35

The following Examples were prepared in a similar way to Example 28 by replacing at each step the appropriate starting materials.

| Ex | Structure | Starting materials | 1H NMR | LC-MS |
|---|---|---|---|---|
| 29 | 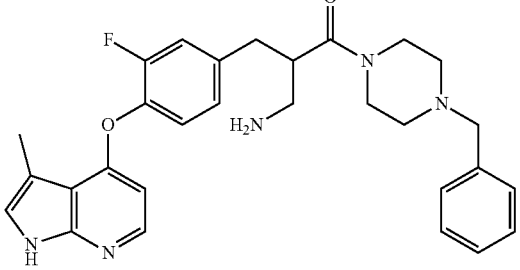<br>3-amino-1-(4-benzylpiperazin-1-yl)-2-(3-fluoro-4-((3-methyl-1H-pyrrolo[2,3-b]pyridin-4-yl)oxy)benzyl)propan-1-one | 28C-a and 1-benzyl-piperazine | $^1$H NMR (400 MHz, d6-DMSO) δ 11.41 (s, 1H), 7.98 (d, J = 5.4 Hz, 1H), 7.32-7.21 (m, 6H), 7.14 (s, 1H), 7.08-7.03 (m, 1H), 6.16-6.14 (m, 1H), 3.64-3.54 (m, 1H), 3.46-3.40 (m, 1H), 3.37 (s, 3H), 3.28-3.21 (m, 1H), 3.16-3.08 (m, 1H), 2.85-2.69 (m, 2H), 2.59 (dd, J = 6.2, 12.9 Hz, 1H), 2.39 (d, J = 1.0 Hz, 3H), 2.37-2.32 (m, 2H), 2.02-1.97 (m, 1H), 1.82-1.71 (m, 2H). | Rt = 2.16 min, m/z 502.3 [M + H]$^+$ (Method 1) |
| 30 | 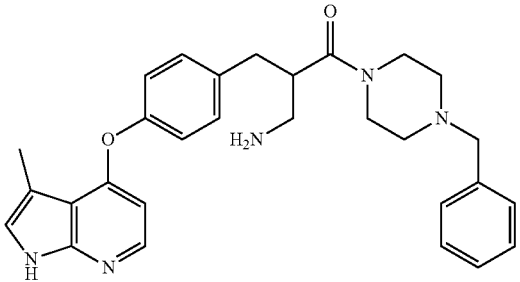 [SMILES: Cc1c[nH]c2nccc(Oc3ccc(CC(CN)C(=O)N4CCN(Cc5ccccc5)CC4)cc3)c12]<br>3-amino-1-(4-benzylpiperazin-1-yl)-2-(4-((3-methyl-1H-pyrrolo[2,3-b]pyridin-4-yl)oxy)benzyl)propan-1-one | 28C-b and 1-benzyl-piperazine | $^1$H NMR (400 MHz, d6-DMSO) δ 11.37 (s, 1H), 7.99 (d, J = 5.4 Hz, 1H), 7.32-7.19 (m, 6H), 7.14-7.10 (m, 1H), 7.07 (d, J = 8.3 Hz, 2H), 6.24 (d, J = 5.4 Hz, 1H), 3.64-3.49 (m, 1H), 3.39 (s, 2H), 3.17-3.00 (m, 2H), 2.82-2.57 (m, 6H), 2.36-2.31 (m, 6H), 2.06-1.99 (m, 1H), 1.77-1.75 (m, 1H). | Rt = 1.97 min, m/z 484.4 [M + H]$^+$ (Method 1) |
| 31 | 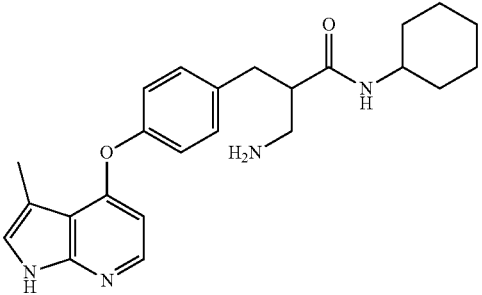 [SMILES: Cc1c[nH]c2nccc(Oc3ccc(CC(CN)C(=O)NC4CCCCC4)cc3)c12]<br>3-amino-N-cyclohexyl-2-(4-((3-methyl-1H-pyrrolo[2,3-b]pyridin-4-yl)oxy)benzyl)propanamide | 28C-b and cyclohexyl amine | $^1$H NMR (400 MHz, d6-DMSO) δ 11.35 (s, 1H), 7.97 (d, J = 5.4 Hz, 1H), 7.62 (d, J = 8.0 Hz, 1H), 7.23 (d, J = 8.6 Hz, 2H), 7.11 (s, 1H), 7.02 (d, J = 8.7 Hz, 2H), 6.20 (d, J = 5.4 Hz, 1H), 3.55-3.45 (m, 1H), 2.73-2.65 (m, 3H), 2.60-2.53 (m, 1H), 2.47-2.39 (m, 1H), 2.32 (d, J = 1.0 Hz, 3H), 1.71-1.47 (m, 6H), 1.26-0.91 (m, 6H). | Rt = 2.52 min, m/z 407.3 [M + H]$^+$ (Method 1) |

| Ex | Structure | Starting materials | 1H NMR | LC-MS |
|---|---|---|---|---|
| 32 | 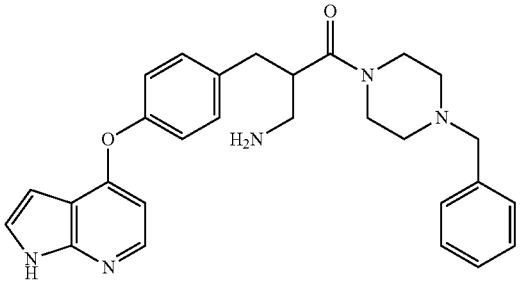 [SMILES: NCC(Cc1ccc(Oc2ccnc3[nH]ccc23)cc1)C(=O)N1CCN(Cc2ccccc2)CC1]<br>2-(4-((1H-pyrrolo[2,3-b]pyridin-4-yl)oxy)benzyl)-3-amino-1-(4-benzylpiperazin-1-yl)propan-1-one | 28C-c and 1-benzyl-piperazine | $^1$H NMR (400 MHz, d6-DMSO) δ 11.73 (s, 1H), 8.06 (d, J = 5.4 Hz, 1H), 7.35-7.20 (m, 8H), 7.09 (d, J = 8.5 Hz, 2H), 6.40 (d, J = 5.4 Hz, 1H), 6.19 (d, J = 3.4 Hz, 1H), 3.41-3.37 (m, 5H), 3.14-3.03 (m, 1H), 2.82-2.55 (m, 5H), 2.34-2.23 (m, 3H), 2.11-2.05 (m, 1H), 1.88-1.84 (m, 1H). | Rt = 1.87 min, m/z 470.3 [M + H]$^+$ (Method 1) |
| 33 | 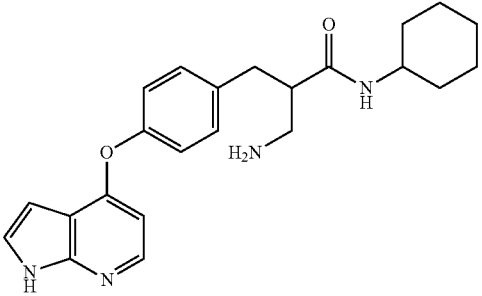 [SMILES: NCC(Cc1ccc(Oc2ccnc3[nH]ccc23)cc1)C(=O)NC1CCCCC1]<br>2-(4-((1H-pyrrolo[2,3-b]pyridin-4-yl)oxy)benzyl)-3-amino-N-cyclohexyl-propanamide | 28C-c and cyclohexyl amine | $^1$H NMR (400 MHz, d6-DMSO) δ 11.70 (s, 1H), 8.04 (d, J = 5.4 Hz, 1H), 7.65 (d, J = 8.0 Hz, 1H), 7.34-7.31 (m, 1H), 7.24 (d, J = 8.5 Hz, 2H), 7.07 (d, J = 8.5 Hz, 2H), 6.34 (d, J = 5.4 Hz, 1H), 6.19 (d, J = 3.5 Hz, 1H), 3.55-3.46 (m, 1H), 2.75-2.66 (m, 3H), 2.57 (dd, J = 5.3, 12.4 Hz, 1H), 2.48-2.40 (m, 1H), 1.72-1.47 (m, 6H), 1.26-0.91 (m, 6H). | Rt = 2.42 min, m/z 393.3 [M + H]$^+$ (Method 1) |
| 34 | 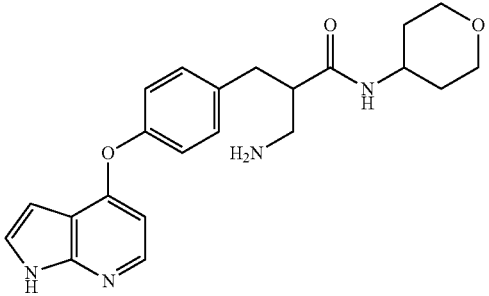 [SMILES: NCC(Cc1ccc(Oc2ccnc3[nH]ccc23)cc1)C(=O)NC1CCOCC1]<br>2-(4-((1H-pyrrolo[2,3-b]pyridin-4-yl)oxy)benzyl)-3-amino-N-(tetrahydro-2H-pyran-4-yl)propanamide | 28C-c and 4-amino-tetrahydro-pyran | $^1$H NMR (400 MHz, d6-DMSO) δ 11.71 (s, 1H), 8.05 (d, J = 5.4 Hz, 1H), 7.77 (d, J = 7.8 Hz, 1H), 7.33 (d, J = 3.4 Hz, 1H), 7.24 (d, J = 8.4 Hz, 2H), 7.07 (d, J = 8.4 Hz, 2H), 6.35 (d, J = 5.4 Hz, 1H), 6.18 (d, J = 3.4 Hz, 1H), 3.81-3.66 (m, 3H), 3.30-3.22 (m, 4H), 2.76-2.68 (m, 3H), 2.58 (dd, J = 5.3, 12.4 Hz, 1H), 2.48-2.41 (m, 1H), 1.69-1.57 (m, 1H), 1.56-1.46 (m, 1H), 1.42-1.12 (m, 2H). | Rt = 1.94 min, m/z 395.2 [M + H]$^+$ (Method 1) |

| Ex | Structure | Starting materials | 1H NMR | LC-MS |
|---|---|---|---|---|
| 35 | 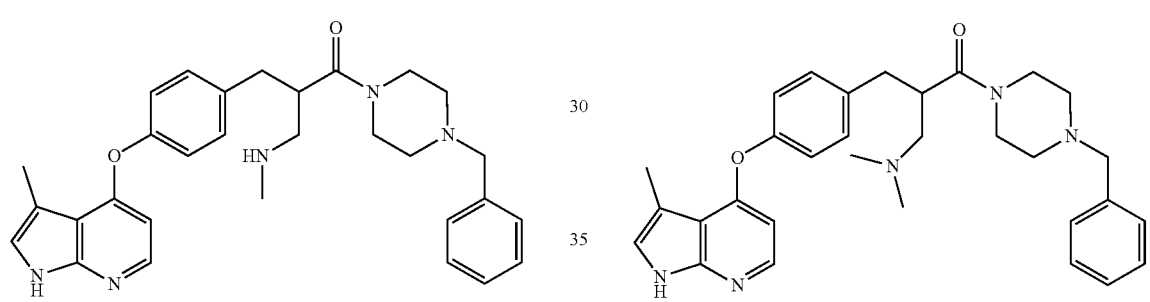<br><br>2-(4-((1H-pyrrolo[2,3-b]pyridin-4-yl)oxy)-benzyl)-3-amino-N-(3-methoxypropyl)-propanamide | 28C-c and 3-methoxy-propan-1-amine | ¹H NMR (400 MHz, d6-DMSO) δ 11.71 (s, 1H), 8.06 (d, J = 5.4 Hz, 1H), 7.84-7.76 (m, 1H), 7.34-7.32 (m, 1H), 7.26-7.20 (m, 2H), 7.09-7.04 (m, 2H), 6.37 (d, J = 5.4 Hz, 1H), 6.17 (d, J = 3.4 Hz, 1H), 3.18-3.16 (m, 6H), 3.15-2.92 (m, 3H), 2.80-2.67 (m, 3H), 2.62-2.56 (m, 1H), 2.48-2.39 (m, 1H), 1.57-1.48 (m, 2H). | Rt = 1.96 min, m/z 383.2 [M + H]⁺ (Method 1) |

Example 36

1-(4-Benzylpiperazin-1-yl)-2-(4-((3-methyl-1H-pyrrolo[2,3-b]pyridin-4-yl)oxy)benzyl)-3-(methylamino)propan-1-one (Example 36)

A solution of Example 30 (130 mg, 0.269 mmol) and methyl trifluoromethanesulfonate (35 µL, 0.323 mmol) in HFIP (1 mL) was stirred at RT for 30 min. The reaction mixture was loaded onto a 5 g SCX-2 cartridge and the column was flushed with methanol. The product was eluted with 2M ammonia in methanol and the solvent was evaporated. The product was purified by MDAP and obtained as a white solid (14 mg).

LCMS (Method 1): Rt=2.03 min, m/z 498.2 [M+H]⁺

¹H NMR (400 MHz, d6-DMSO) δ 11.36 (s, 1H), 7.99 (d, J=5.4 Hz, 1H), 7.33-7.20 (m, 8H), 7.13-7.04 (m, 3H), 6.24 (d, J=5.4 Hz, 1H), 3.61-3.52 (m, 1H), 3.36 (s, 3H), 3.27-3.16 (m, 2H), 2.81-2.65 (m, 4H), 2.34 (d, J=1.0 Hz, 3H), 2.33-2.26 (m, 2H), 2.24 (s, 3H), 1.98 (m, 1H), 1.76-1.66 (m, 1H), 1.56-1.52 (m, 11H).

Example 37

1-(4-Benzylpiperazin-1-yl)-3-(dimethylamino)-2-(4-((3-methyl-1H-pyrrolo[2,3-b]pyridin-4-yl)oxy)benzyl)propan-1-one (Example 37)

A solution of Example 30 (125 mg, 0.259 mmol) and paraformaldehyde (17 mg, 0.569 mmol) and sodium borohydride (21 mg, 0.54 mmol) in 1,1,1-trifluoroethane (3 mL) was stirred at 70° C. for 90 min. The reaction mixture was loaded onto a 5 g SCX-2 cartridge and the column was flushed with methanol. The residue was dissolved in THF (3 mL) and 1N NaOH (1 mL) was added. The mixture was stirred at RT for 30 min and then partitioned between ethyl acetate (10 mL) and brine (10 mL). The organic layer was separated, dried (Na₂SO₄) and evaporated. The product was purified by HPLC (Kinetex C18, basic method) and obtained as a white solid (26 mg).

LCMS (Method 1): Rt=2.03 min, m/z 512.3 [M+H]⁺

¹H NMR (400 MHz, d6-DMSO) δ ¹H NMR (400 MHz, DMSO) δ 11.36 (s, 1H), 7.99 (d, J=5.4 Hz, 1H), 7.32-7.21 (m, 7H), 7.14-7.10 (m, 1H), 7.06 (d, J=8.6 Hz, 2H), 6.24 (d, J=5.4 Hz, 1H), 3.63-3.59 (m, 1H), 3.34 (s, 2H), 3.30-3.14 (m, 4H), 2.76 (dd, J=4.6, 12.9 Hz, 1H), 2.66 (dd, J=10.0, 12.9 Hz, 1H), 2.55 (dd, J=7.5, 11.2 Hz, 1H), 2.34 (d, J=1.0 Hz, 3H), 2.31-2.19 (m, 3H), 2.12 (s, 6H), 1.96-1.92 (m, 1H), 1.61-1.57 (m, 1H).

Example 38

Step A

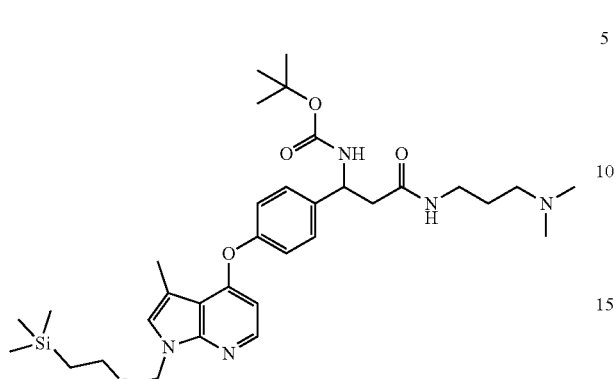

tert-Butyl (3-((3-(dimethylamino)propyl)amino)-1-(4-((3-methyl-1-((2-(trimethylsilyl)ethoxy)methyl)-1H-pyrrolo[2,3-b]pyridin-4-yl)oxy)phenyl)-3-oxo-propyl)carbamate (Intermediate 38A)

A mixture of Intermediate 1D-c (400 mg, 0.74 mmol) and $N^1,N^1$-dimethylpropane-1,3-diamine (140 μL, 1.11 mmol) in DCM (10 mL) was treated with COMU (635 mg, 1.5 mmol) and then DIPEA (285 μL, 1.63 mmol). The reaction mixture was stirred at RT for 80 min at RT before the addition of a further quantity of COMU (300 mg, 0.7 mmol). After stirring for a further 30 min, an additional quantity of DIPEA (70 μL, 0.55 mmol) was added. After stirring at RT for 30 min, the reaction mixture was diluted with DCM (10 mL) and the organic mixture was washed with water (10 mL). The aqueous phase was extracted with DCM (2×10 mL) and the combined organics were dried ($Na_2SO_4$) and evaporated. The crude product was chromatographed on a 10 g Si cartridge eluting with 2-20% methanol in DCM. The product was obtained as a brown foam (350 mg).

LCMS (Method 4): Rt=1.29 min, m/z 626.6 [M+H]$^+$

Step B

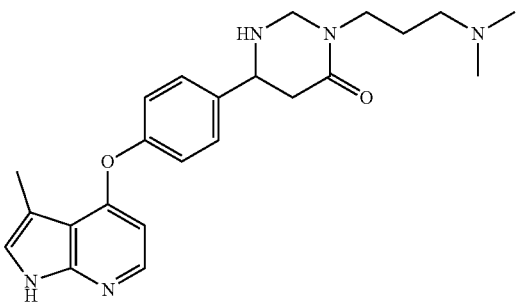 [SMILES: Cc1c[nH]c2nccc(Oc3ccc(C4CC(=O)N(CCCN(C)C)CN4)cc3)c12]

3-(3-(dimethylamino)propyl)-6-(4-((3-methyl-1H-pyrrolo[2,3-b]pyridin-4-yl)oxy)phenyl)tetrahydropyrimidin-4(1H)-one (Example 38)

Intermediate 38A (350 mg, 0.56 mmol) was dissolved in DCM (6 mL) and TFA (6 mL) was added. The solution was stirred at RT for 2.5 h and then filtered through a 5 g SCX-2 cartridge. The cartridge was washed with DCM (15 mL) and methanol (15 mL) before elution of the product with 2M ammonia in methanol (25 mL). Evaporation gave a residue (220 mg) which was dissolved in a mixture of THF (3 mL) and water (3 mL). To the solution was added 32% aqueous formaldehyde solution (40 μL, 0.48 mmol) and the reaction was stirred at RT overnight before being evaporated to dryness in vacuo. The residue was taken up into water (3 mL) and the yellow solution was treated with TFA (0.5 mL). After stirring at RT for 4 h, the reaction mixture was diluted with water and filtered through a 2 g SCX-2 cartridge. After flushing with methanol, the crude product was eluted with 2M ammonia in methanol (15 mL). The solution was left to stand at RT overnight and then evaporated to dryness. The crude product was purified by MDAP to give a white solid (60 mg).

LCMS (Method 1): Rt=3.22 min, m/z 408.2 [M+H]$^+$ $^1$H NMR (400 MHz, DMSO, $D_2O$ added) δ 8.02 (d, J=5.4 Hz, 1H), 7.46 (d, J=8.5 Hz, 2H), 7.12 (d, J=8.6 Hz, 3H), 6.29 (d, J=5.4 Hz, 1H), 4.27 (d, J=11.6 Hz, 1H), 4.18 (d, J=11.5 Hz, 1H), 4.08 (dd, J=4.4, 10.9 Hz, 1H), 3.35-3.16 (m, 2H), 2.57 (dd, J=4.5, 16.8 Hz, 1H), 2.32-2.31 (m, 6H), 2.12 (s, 6H), 1.67-1.58 (m, 2H).

Preparation of Example 39 and 40

The following Examples were prepared in a similar way to Example 38 by replacing in step A the $N^1,N^1$-dimethylpropane-1,3-diamine with the amine indicated.

| Ex | Structure | Amine | 1H NMR | LC-MS |
|---|---|---|---|---|
| 39 | 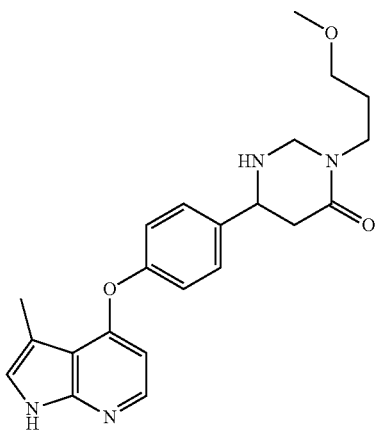 [SMILES: COCCCN1CNC(c2ccc(Oc3ccnc4[nH]cc(C)c34)cc2)CC1=O]<br>3-(4-((3-methyl-1H-pyrrolo[2,3-b]pyridin-4-yl)oxy)phenyl)-N-(tetrahydro-2H-pyran-4-yl)pyrrolidine-2-carboxamide | 3-methoxy-propan-1-amine | $^1$H NMR (400 MHz, DMSO) δ 11.38 (s, 1H), 8.01 (d, J = 5.4 Hz, 1H), 7.46 (d, J = 8.6 Hz, 2H), 7.15-7.08 (m, 3H), 6.27 (d, J = 5.4 Hz, 1H), 4.27 (t, J = 11.3 Hz, 1H), 4.16 (dd, J = 5.5, 11.8 Hz, 1H), 4.08 (dt, J = 4.3, 11.0 Hz, 1H), 3.30-3.23 (m, 7H), 2.60-2.50 (m, 2H), 2.32 (s, 3H), 2.29-2.24 (m, 1H), 1.77-1.69 (m, 2H). | Rt = 2.39 min, m/z 395.1 [M + H]$^+$ (Method 1) |
| 40 | 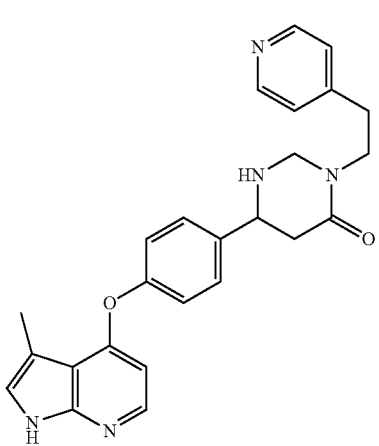 [SMILES: Cc1c[nH]c2nccc(Oc3ccc(C4CC(=O)N(CCc5ccncc5)CN4)cc3)c12]<br>3-(4-((3-methyl-1H-pyrrolo[2,3-b]pyridin-4-yl)oxy)phenyl)-N-(tetrahydro-2H-pyran-4-yl)pyrrolidine-2-carboxamide | 2-(pyridin-4-yl)ethan-1-amine | $^1$H NMR (400 MHz, DMSO) δ 11.38 (s, 1H), 8.49-8.46 (m, 2H), 8.01 (d, J = 5.4 Hz, 1H), 7.45 (d, J = 8.6 Hz, 2H), 7.31-7.28 (m, 2H), 7.13-7.09 (m, 3H), 6.27 (d, J = 5.4 Hz, 1H), 4.21-4.17 (m, 2H), 4.08-4.00 (m, 1H), 3.51 (t, J = 6.9 Hz, 2H), ), 3.37-3.25 (m, 1H), 2.86-2.81 (m, 2H), 2.61-2.54 (m, 1H), 2.32-2.30 (m, 4H). | Rt = 1.95 min, m/z 428.2 [M + H]$^+$ (Method 1) |

Example 41

3-(3-(Dimethylamino)propyl)-5-(3-fluoro-4-((3-methyl-1H-pyrrolo[2,3-b]pyridin-4-yl)oxy)benzyl)tetrahydropyrimidin-4(1H)-one (Example 41)

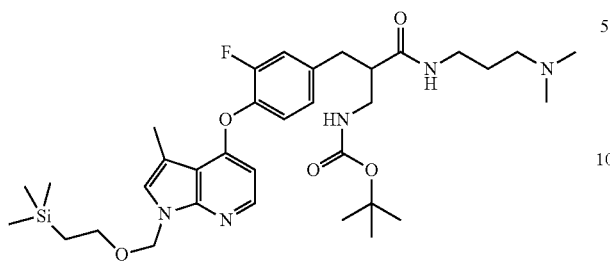

Step A tert-Butyl (3-((3-(dimethylamino)propyl)amino)-2-(3-fluoro-4-((3-methyl-1-((2-(trimethylsilyl)ethoxy)methyl)-1H-pyrrolo[2,3-b]pyridin-4-yl)oxy)benzyl)-3-oxopropyl)carbamate (Intermediate 41A)

Intermediate 41A was prepared from Intermediate 1D-e and $N^1,N^1$-dimethylpropane-1,3-diamine using a similar procedure to Step A of Example 38.

LCMS (Method 4): Rt=1.30 min, m/z 658.5 [M+H]$^+$

Step B

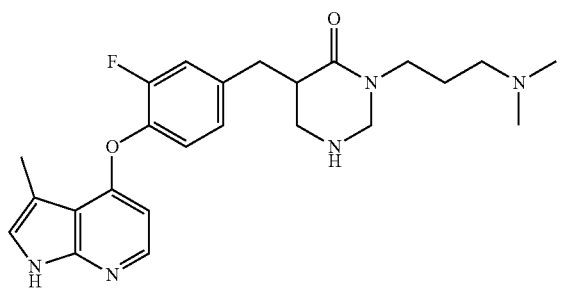 [SMILES: Cc1c[nH]c2nccc(Oc3ccc(CC4CNCN(CCCN(C)C)C4=O)cc3F)c12]

Intermediate 41A (570 mg, 0.86 mmol) was dissolved in DCM (5 mL) and TFA (5 mL) was added. The solution was stirred at RT for 90 min and then filtered through a 5 g SCX-2 cartridge. The cartridge was flushed with DCM and then methanol before elution with 2M ammonia in methanol. The basic eluent was allowed to stand at RT for 4 days and then evaporated to dryness. Water (2 mL) was added followed by 32% aqueous formaldehyde solution (100 µL, 1.25 mmol) and the reaction was stirred at RT for 6 h. THF (1 mL) was added and stirring was continued at 60° C. for 4 h. After allowing to cool, the mixture was diluted with THF and filtered through a 2 g SCX-2 cartridge, rinsing with methanol. The basic product was eluted from the cartridge with 2M ammonia in methanol and the solution was allowed to stand at RT for 3 days. Evaporation gave a crude residue which was purified by MDAP to give a white solid (11 mg).

LCMS (Method 2): Rt=3.43 min, m/z 440.3 [M+H]$^+$ $^1$H NMR (400 MHz, DMSO) δ 11.39 (s, 1H), 7.99 (d, J=5.4 Hz, 1H), 7.31 (dd, J=1.7, 12.1 Hz, 1H), 7.24 (dd, J=8.4, 8.4 Hz, 1H), 7.15-7.11 (m, 2H), 6.16 (d, J=5.4 Hz, 1H), 4.07 (d, J=5.7 Hz, 2H), 3.30-3.08 (m, 4H), 2.97-2.86 (m, 2H), 2.76 (dd, J=9.4, 13.6 Hz, 1H), 2.62-2.54 (m, 1H), 2.38 (s, 3H), 2.15 (dd, J=7.1, 7.1 Hz, 2H), 2.10 (s, 6H), 1.63-1.54 (m, 2H).

Preparation of Example 42 and 43

The following Examples were prepared in a similar way to Example 41 by replacing in step A the $N^1,N^1$-dimethylpropane-1,3-diamine with the amine indicated.

| Ex | Structure | Amine | 1H NMR | LC-MS |
| --- | --- | --- | --- | --- |
| 42 | 3-(4-((3-methyl-1H-pyrrolo[2,3-b]pyridin-4-yl)oxy)phenyl)-N-(tetrahydro-2H-pyran-4-yl)pyrrolidine-2-carboxamide | 3-Methoxy-propan-1-amine | $^1$H NMR (400 MHz, DMSO) δ 11.39-11.39 (m, 1H), 7.99 (d, J = 5.4 Hz, 1H), 7.31 (dd, J = 2.1, 12.0 Hz, 1H), 7.24 (dd, J = 8.4, 8.4 Hz, 1H), 7.15-7.10 (m, 2H), 6.16 (d, J = 5.3 Hz, 1H), 4.07 (d, J = 5.7 Hz, 2H), 3.31-3.10 (m, 9H), 2.99-2.85 (m, 2H), 2.75 (dd, J = 9.6, 13.6 Hz, 1H), 2.62-2.55 (m, 1H), 2.38 (s, 3H), 1.73-1.66 (m, 2H). | Rt = 3.48 min, m/z 427.2 [M + H]$^+$ (Method 2) |

| Ex | Structure | Amine | 1H NMR | LC-MS |
|---|---|---|---|---|
| 43 | 3-(4-((3-methyl-1H-pyrrolo[2,3-b]pyridin-4-yl)oxy)phenyl)-N-(tetrahydro-2H-pyran-4-yl)pyrrolidine-2-carboxamide | 2-(Pyridin-4-yl)-ethan-1-amine | ¹H NMR (400 MHz, DMSO) δ 11.40 (s, 1H), 8.48-8.46 (m, 2H), 7.99 (d, J = 5.4 Hz, 1H), 7.32 (dd, J = 1.9, 11.8 Hz, 1H), 7.28-7.22 (m, 3H), 7.15-7.10 (m, 2H), 6.17 (d, J = 5.2 Hz, 1H), 4.05-3.99 (m, 2H), 3.57-3.49 (m, 1H), 3.44-3.36 (m, 1H), 3.11 (dd, J = 3.8, 13.7 Hz, 1H), 2.99-2.67 (m, 5H), 2.59-2.53 (m, 2H), 2.37 (d, J = 0.9 Hz, 3H). | Rt = 2.06 min, m/z 460.2 [M + H]⁺ (Method 1) |

Examples 44 and 45

Step A

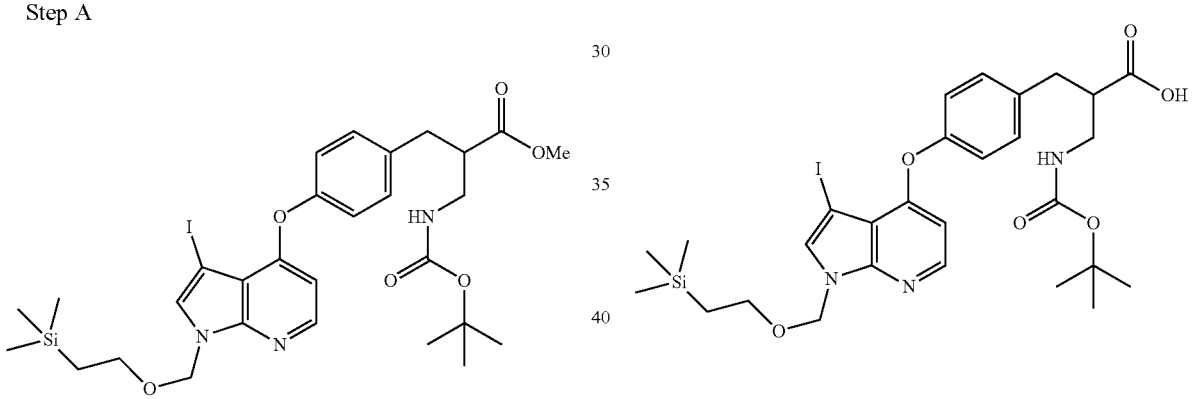

Methyl 3-((tert-butoxycarbonyl)amino)-2-(4-((3-iodo-1-((2-(trimethylsilyl)-ethoxy)methyl)-1H-pyrrolo[2,3-b]pyridin-4-yl)oxy)benzyl)propanoate (Intermediate 44A)

To a stirred ice cold solution of Intermediate 1C-a (1.7 g, 3.06 mmol) in acetonitrile (35 mL) was added NIS (0.72 g, 3.21 mmol) in one portion. The reaction mixture was stirred at 0-5° C. for 30 min before being allowed to warm to RT. After stirring at RT for a further 30 min, the reaction was quenched by adding 10% aqueous sodium thiosulfate solution (50 mL). The product was extracted into ethyl acetate (75 mL) and the organic layer was washed with a further portion of 10% aqueous sodium thiosulfate solution (40 mL), water (50 mL) and brine (50 mL) After drying (Na₂SO₄), the solvent was evaporated and the crude product was chromatographed on a 40 g Si cartridge eluting with 0-50% ethyl acetate in cyclohexane. The product was obtained as a pale yellow oil (1.60 g).

LCMS (Method 4): Rt=1.92 min, m/z 682.3 [M+H]⁺

Step B 3-((tert-Butoxycarbonyl)amino)-2-(4-((3-iodo-1-((2-(trimethylsilyl)ethoxy)-methyl)-1H-pyrrolo[2,3-b]pyridin-4-yl)oxy)benzyl)propanoic acid (Intermediate 44B)

Intermediate 44B was prepared from Intermediate 44/45A using the conditions of Intermediate 1D-a.

LCMS (Method 4): Rt=1.82 min, m/z 668.3 [M+H]⁺

Step C

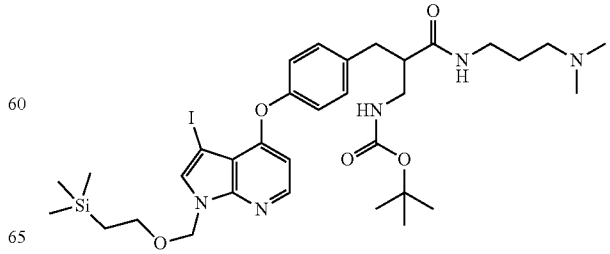

tert-Butyl (3-((3-(dimethylamino)propyl)amino)-2-(4-((3-iodo-1-((2-(trimethylsilyl)ethoxy)methyl)-1H-pyrrolo[2,3-b]pyridin-4-yl)oxy)benzyl)-3-oxopropyl)carbamate (Intermediate 44C)

Intermediate 44C was prepared from Intermediate 44B and N¹,N¹-dimethylpropane-1,3-diamine using a similar procedure to that used for Step A of Example 38.

LCMS (Method 4): Rt=1.33 min, m/z 752.4 [M+H]⁺

Step D

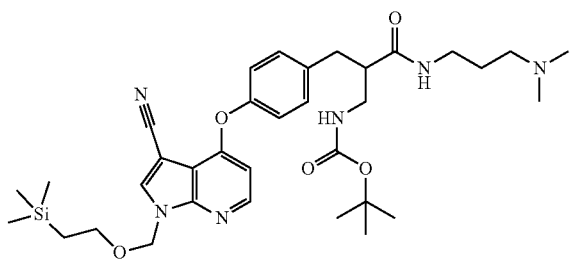

tert-Butyl (2-(4-((3-cyano-1-((2-(trimethylsilyl)ethoxy)methyl)-1H-pyrrolo[2,3-b]pyridin-4-yl)oxy)benzyl)-3-((3-(dimethylamino)propyl)amino)-3-oxopropyl)carbamate (Intermediate 44D)

Intermediate 44C (450 mg, 0.60 mmol), zinc cyanide (77 mg, 0.66 mmol), Pd₂(dba)₃ (55 mg, 0.06 mmol) and dppf (83 mg, 0.15 mmol) were heated at 105° C. in a mixture of DMF (5 mL) and water (0.5 mL) for 2.5 h. After allowing to cool, the mixture was diluted with ethyl acetate (20 mL). The solution was washed with water (2×10 mL) and brine (10 mL), dried (Na₂SO₄) and evaporated. The crude material was chromatographed on a 25 g Si cartridge eluting with 0-5% 2M ammonia in methanol/DCM. The product was obtained as a pale foam (270 mg).

LCMS (Method 4): Rt=1.26 min, m/z 651.5 [M+H]⁺

Step E

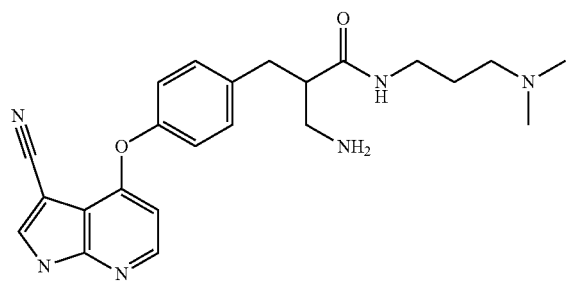 [SMILES: CN(C)CCCNC(=O)C(CN)Cc1ccc(Oc2ccnc3[nH]cc(C#N)c23)cc1]

3-Amino-2-(4-((3-cyano-1H-pyrrolo[2,3-b]pyridin-4-yl)oxy)benzyl)-N-(3-(dimethylamino)propyl)propanamide (Example 44)

Intermediate 44D (270 mg, 0.42 mmol) was dissolved in DCM (5 mL) and TFA (5 mL) was added. The solution was stirred at RT for 90 min and then the volatiles were evaporated in vacuo. Example 44 (product 1) was separated by MDAP and in addition a second product was isolated and characterized as Example 45 (product 2).

LCMS (Method 2): Rt=2.69 min, m/z 421.1 [M+H]⁺

¹H NMR (400 MHz, DMSO) δ 8.37 (s, 1H), 8.17 (d, J=5.5 Hz, 1H), 7.80 (dd, J=5.8, 5.8 Hz, 1H), 7.28 (d, J=8.2 Hz, 2H), 7.14 (d, J=8.6 Hz, 2H), 6.37 (d, J=5.6 Hz, 1H), 3.11-2.93 (m, 4H), 2.80-2.66 (m, 3H), 2.59 (dd, J=4.8, 12.1 Hz, 1H), 2.47-2.42 (m, 1H), 2.12-2.05 (m, 9H), 1.47-1.35 (m, 2H).

Example 45 (Product 2)

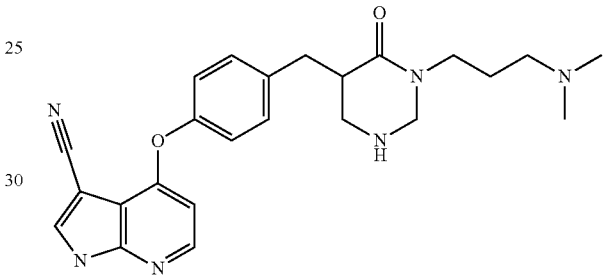

4-(4-((1-(3-(Dimethylamino)propyl)-6-oxohexahydropyrimidin-5-yl)methyl)phenoxy)-1H-pyrrolo[2,3-b]pyridine-3-carbonitrile (Example 45)

LCMS (Method 2): Rt=2.88 min, m/z 433.2 [M+H]⁺

NMR (400 MHz, DMSO) δ 8.38 (s, 1H), 8.20 (d, J=5.6 Hz, 1H), 7.34 (d, J=8.6 Hz, 2H), 7.17 (d, J=8.6 Hz, 2H), 6.42 (d, J=5.5 Hz, 1H), 4.07 (s, 2H), 3.27-3.11 (m, 4H), 2.99-2.93 (m, 1H), 2.86 (dd, J=5.8, 13.5 Hz, 1H), 2.75 (dd, J=9.8, 13.6 Hz, 1H), 2.64-2.57 (m, 1H), 2.17 (t, J=7.3 Hz, 2H), 2.11 (s, 6H), 2.08-2.04 (m, 1H), 1.64-1.55 (m, 2H).

Preparation of Example from 46 to 49

The following examples were prepared in a similar way to Example 44 by replacing N¹,N¹-dimethylpropane-1,3-diamine with the amine indicated. Where the reaction led to two products, as described for Example 44, they are indicated as product 1 and product 2.

| Ex | Structure | Amine | 1H NMR | LC-MS |
|---|---|---|---|---|
| 46 | (Product 1)<br>3-amino-2-(4-((3-cyano-1H-pyrrolo[2,3-b]pyridin-4-yl)oxy)benzyl)-N-(1-methylpiperidin-4-yl)propanamide | 1-Methyl-piperidin-4-amine | $^1$H NMR (400 MHz, DMSO) δ 8.37 (s, 1H), 8.17 (d, J = 5.5 Hz, 1H), 7.70 (d, J = 7.8 Hz, 1H), 7.28 (d, J = 8.6 Hz, 2H), 7.17-7.13 (m, 2H), 6.35 (d, J = 5.5 Hz, 1H), 3.52-3.44 (m, 3H), 3.12-3.02 (m, 1H), 2.77-2.55 (m, 6H), 2.11 (s, 3H), 1.92-1.82 (m, 2H), 1.66 1.60 (m, 1H), 1.53-1.47 (m, 1H), 1.41-1.17 (m, 2H). | Rt = 2.66 min, m/z 433.2 [M + H]$^+$ (Method 2) |
| 47 | (Product 2)<br>4-(4-((1-(1-methylpiperidin-4-yl)-6-oxohexahydro-pyrimidin-5-yl)methyl)-phenoxy)-1H-pyrrolo[2,3-b]pyridine-3-carbonitrile | 1-Methyl-piperidin-4-amine | $^1$H NMR (400 MHz, DMSO) δ 8.38 (s, 1H), 8.20 (d, J = 5.5 Hz, 1H), 7.33 (d, J = 8.6 Hz, 2H), 7.17 (d, J = 8.6 Hz, 2H), 6.40 (d, J = 5.5 Hz, 1H), 4.19-3.98 (m, 3H), 3.12 (dd, J = 4.0, 13.6 Hz, 1H), 2.87-2.70 (m, 5H), 2.70-2.52 (m, 3H), 2.14 (s, 3H), 1.94-1.84 (m, 2H), 1.79-1.65 (m, 2H), 1.46 (d, J = 10.3 Hz, 2H). | Rt = 2.86 min, m/z 445.1 [M + H]$^+$ (Method 2) |
| 48 | 4-(4-(2-(aminomethyl)-3-((1S,4S)-5-methyl-2,5-diazabicyclo[2.2.1]heptan-2-yl)-3-oxopropyl)phenoxy)-1H-pyrrolo[2,3-b]pyridine-3-carbonitrile | (1S,4S)-2-Methyl-2,5-diaza-bicyclo[2.2.1]-heptane | $^1$H NMR (400 MHz, DMSO) δ 8.38-8.36 (m, 1H), 8.21-8.16 (m, 1H), 7.32-7.24 (m, 2H), 7.19-7.12 (m, 2H), 6.44-6.30 (m, 1H), 4.47 (d, J = 9.2 Hz, 1H), 3.62 (d, J = 9.5 Hz, 1H), 3.07-2.96 (m, 2H), 2.84-2.63 (m, 6H), 2.25 (d, J = 7.9 Hz, 2H), 2.10-2.00 (m, 3H), 1.74-0.99 (m, 3H). | Rt = 2.49/2.56 min, m/z 431.1 [M + H]$^+$ (Method 2) |

| Ex | Structure | Amine | 1H NMR | LC-MS |
|---|---|---|---|---|
| 49 | 4-(4-(2-(aminomethyl)-3-oxo-3-(4-(pyridin-2-ylmethyl)piperazin-1-yl)propyl)phenoxy)-1H-pyrrolo[2,3-b]pyridine-3-carbonitrile | 1-(pyridin-2-ylmethyl)-piperazine | $^1$H NMR (400 MHz, DMSO) δ 8.50-8.45 (m, 1H), 8.37 (s, 1H), 8.20 (d, J = 5.5 Hz, 1H), 7.74 (dt, J = 1.8, 7.7 Hz, 1H), 7.41 (d, J = 7.8 Hz, 1H), 7.30-7.22 (m, 3H), 7.16 (d, J = 8.6 Hz, 2H), 6.39 (d, J = 5.5 Hz, 1H), 3.59-3.48 (m, 5H), 3.16-3.04 (m, 5H), 2.83-2.69 (m, 3H), 2.60 (dd, J = 5.5, 12.4 Hz, 1H), 2.39-2.32 (m, 2H), 2.17-2.12 (m, 1H), 2.02-1.95 (m, 1H). | Rt = 1.92 min, m/z 496.2 [M + H]$^+$ (Method 2) |

Example 50

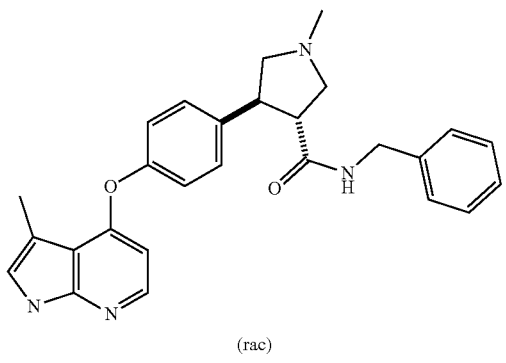

(rac)

rac-(3R,4S)-N-benzyl-1-methyl-4-(4-((3-methyl-1H-pyrrolo[2,3-b]pyridin-4-yl)oxy)phenyl)pyrrolidine-3-carboxamide (Example 50)

Example 50 was prepared from Example 17 using a similar procedure to that used for Example 37.

LCMS (Method 1): Rt=2.49 min, m/z 441.3 [M+H]$^+$ $^1$H NMR (400 MHz, DMSO) δ 11.36 (s, 1H), 8.34 (t, J=6.0 Hz, 1H), 7.99 (d, J=5.4 Hz, 1H), 7.35-7.07 (m, 10H), 6.24 (d, J=5.4 Hz, 1H), 4.34-4.18 (m, 2H), 3.67-3.60 (m, 1H), 3.02-2.93 (m, 2H), 2.85 (t, J=8.6 Hz, 1H), 2.70 (dd, J=6.2, 9.0 Hz, 1H), 2.62-2.54 (m, 1H), 2.32 (d, J=1.1 Hz, 3H), 2.30 (s, 3H).

The following racemic examples were resolved using the conditions given below to give the pure enantiomers.

| Racemate | Separation | Analysis | 1st eluting | 2nd eluting |
|---|---|---|---|---|
| Example 4 Separation 1 | MD SFC YMC Amylose-C 30/70 IPA (0.5% DEA)/CO$_2$ 100 mL/min, 28° C. 225 nM; column dimensions 250 × 20 mm id 5 μm | MD SFC YMC Amylose-C 30/70 IPA (0.5% DEA)/CO$_2$ 5 mL/min, 40° C.; column dimensions 250 × 4.6 mm, 5 μm | Example 4A Rt = 2.3 min | Example 4B Rt = 3.3 min |
| Example 4A Separation 2 Diastereoisomer A | MD SFC YMC Amylose-C 30/70 IPA (0.5% DEA)/CO$_2$ 100 mL/min, 40° C. 225 nM; column dimensions 250 × 20 mm id 5 μm | MD SFC YMC Amylose-C 30/70 IPA (0.5% DEA)/CO$_2$ 5 mL/min, 40° C.; column dimensions 150 × 2.0 mm, 5 μm | Example 4A Rt = 4.5 min | |
| Example 4A Separation 2 Diastereoisomer B | MD SFC YMC Amylose-C 30/70 IPA (0.5% DEA)/CO$_2$ 100 mL/min, 40° C. 225 nM; column dimensions 250 × 20 mm id 5 μm | MD SFC YMC Amylose-C 35/65 IPA (0.5% DEA)/CO$_2$ 5 mL/min, 40° C.; column dimensions 150 × 2.0 mm, 5 μm | | Example 4B Rt = 3.8 min |

-continued

| Racemate | Separation | Analysis | 1st eluting | 2nd eluting |
| --- | --- | --- | --- | --- |
| Example 5 Separation 1 | MD SFC Lux Cellulose-4 40/60 MeOH/IPA (50/50/0.5% DEA)/$CO_2$ 100 mL/min, 40° C.; 215 nM; column dimensions 250 × 20 mm id 5 μm | MD SFC Lux Cellulose-4 40/60 MeOH/IPA (50/50/0.5% DEA)/$CO_2$ 5 mL/min, 40° C.; column dimensions 250 × 4.6 mm, 5 μm | Example 5A Rt = 7.0 min | Example 5B Rt = 8.4 min |
| Example 5A Separation 2 Enantiomer A | MD SFC Lux Cellulose-4 40/60 MeOH/IPA (50/50/0.1% DEA)/$CO_2$ 100 mL/min, 40° C.; 220 nM; column dimensions 250 × 20 mm id 5 μm | MD SFC Lux Cellulose-4 40/60 MeOH/IPA (50/50/0.5% DEA)/$CO_2$ 5 mL/min, 40° C.; column dimensions 150 × 2.0 mm, 3 μm | Example 5A Rt = 7.0 min | |
| Example 5B Separation 2 Enantiomer B | MD SFC Lux Cellulose-4 40/60 MeOH/IPA (0.5% DEA)/$CO_2$ 100 mL/min, 40° C.; 220 nM; column dimensions 250 × 20 mm id 5 μm | MD SFC Lux Cellulose-4 40/60 MeOH/IPA (50/50/0.5% DEA)/$CO_2$ 5 mL/min, 40° C.; column dimensions 150 × 2.0 mm, 3 μm | | Example 5B Rt = 7.9 min |
| Example 7 | MD SFC YMC Amylose-C 45/55 MeOH (0.1% DEA)/$CO_2$ 15 mL/min, 40° C.; 215 nM; column dimensions 250 × 10 mm id 5 μm | MD SFC YMC Amylose-C 45/55 MeOH (0.1% DEA)/$CO_2$ 5 mL/min, 40° C.; column dimensions 250 × 4.6 mm, 5 μm | Example 7A Rt = 3.3 min | Example 7B Rt = 4.5 min |
| Example 29 | MD SFC Lux cellulose-4 40/60 MeOH (0.1% DEA)/$CO_2$ 15 mL/min, 40° C.; 220 nM; column dimensions 250 × 10 mm id 5 μm | MD SFC Lux Cellulose-4 40/60 MeOH (0.1% DEA)/$CO_2$ 0.95 mL/min, 40° C.; column dimensions 150 × 2 mm, 3 μm | Example 29A Rt = 3.3 min | Example 29B Rt = 4.0 min |
| Example 32 | MD SFC Lux cellulose-4 40/60 MeOH (0.1% DEA)/$CO_2$ 90 mL/min, 40° C.; 220 nM; column dimensions 250 × 20 mm id 5 μm | MD SFC Lux Cellulose-4 40/60 MeOH (0.1% DEA)/$CO_2$ 0.95 mL/min, 40° C.; column dimensions 150 × 2 mm, 3 μm | Example 32A Rt = 4.0 min | Example 32B Rt = 5.2 min |
| Example 17 | MD SFC YMC Cellulose-SC 55/45 IPA (0.1% DEA)/$CO_2$ 70 mL/min, 40° C.; 225 nM; column dimensions 250 × 20 mm id 5 μm | MD SFC YMC Cellulose-SC 55/45 IPA (0.1% DEA)/$CO_2$ 5 mL/min, 40° C.; column dimensions 250 × 4.6 mm, 5 μm | Example 17A Rt = 1.9 min | Example 17B Rt = 3.4 min |

Pharmacological Activity of the Compounds of the Invention

In Vitro Inhibitory Activity Assay Description

The effectiveness of compounds of the present invention to inhibit Rho kinase activity can be determined in a 10 μl assay containing 40 mM Tris pH7.5, 20 mM $MgCl_2$ 0.1 mg/ml BSA, 50 μM DTT and 2.5 μM peptide substrate (Myelin Basic Protein) using an ADP-Glo kit (Promega). Compounds were dissolved in DMSO such that the final concentration of DMSO was 1% in the assay. All reactions/incubations are performed at 25° C. Compound (2 ul) and either Rho kinase 1 or 2 (4 μl) were mixed and incubated for 30 mins. Reactions were initiated by addition of ATP (4 μl) such that the final concentration of ATP in the assay was 10 μM. After a 1 hour incubation 10 μl of ADP-Glo Reagent was added and after a further 45 minute incubation 20 ul of Kinase Detection Buffer was added and the mixture incubated for a further 30 minutes. The luminescent signal was measured on a luminometer. Controls consisted of assay wells that did not contain compound with background determined using assay wells with no enzyme added. Compounds were tested in dose-response format and the inhibition of kinase activity was calculated at each concentration of compound. To determine the $IC_{50}$ (concentration of compound required to inhibit 50% of the enzyme activity) data were fit to a plot of % inhibition vs $Log_{10}$ compound concentration using a sigmoidal fit with a variable slope and fixing the maximum to 100% and the minimum to 0%. To determine the Ki values the Cheng-Prusoff equation was utilized (Ki=IC$_{50}$/(1+[S]/Km)

Compounds according to the invention showed Ki values lower than 5 μM and for most of the compounds of the invention Ki is even lower that 500 nM.

The results for individual compounds are provided below in Table and are expressed as range of activity.

TABLE

| Example | Activity ROCK1 | Activity ROCK2 |
|---|---|---|
| 1 | +++ | +++ |
| 2 | +++ | +++ |
| 3 | +++ | +++ |
| 4 | +++ | +++ |
| 5 | +++ | +++ |
| 6 | + | + |
| 7 | +++ | +++ |
| 8 | + | + |
| 9 | + | + |
| 10 | + | + |
| 11 | + | + |
| 12 | + | + |
| 13 | + | + |
| 14 | + | + |
| 15 | +++ | +++ |
| 16 | ++ | ++ |
| 17 | +++ | +++ |
| 18 | ++ | +++ |
| 19 | +++ | +++ |
| 20 | +++ | +++ |
| 21 | ++ | +++ |
| 22 | +++ | +++ |
| 23 | +++ | +++ |
| 24 | ++ | ++ |
| 25 | ++ | ++ |
| 26 | ++ | ++ |
| 27 | ++ | ++ |
| 28 | +++ | +++ |
| 29 | +++ | +++ |
| 30 | +++ | +++ |
| 31 | +++ | +++ |
| 32 | +++ | +++ |
| 33 | ++ | ++ |
| 34 | ++ | ++ |
| 35 | ++ | ++ |
| 36 | +++ | +++ |
| 37 | +++ | +++ |
| 38 | + | + |
| 39 | + | + |
| 40 | + | + |
| 41 | ++ | ++ |
| 42 | + | ++ |
| 43 | + | + |
| 44 | +++ | +++ |
| 45 | ++ | ++ |
| 46 | +++ | +++ |
| 47 | ++ | ++ |
| 48 | ++ | +++ |
| 49 | ++ | +++ |
| 50 | ++ | +++ |
| 4A | ++ | ++ |
| 4B | +++ | +++ |
| 5A | ++ | ++ |
| 5B | +++ | +++ |
| 7A | +++ | +++ |
| 7B | ++ | ++ |
| 29A | ++ | ++ |
| 29B | +++ | +++ |
| 32A | ++ | ++ |
| 32B | +++ | +++ |
| 17A | +++ | +++ |
| 17B | ++ | ++ | wherein the compounds are classified in term of potency with respect to their inhibitory activity on rock1 rock 2 isoforms according to the following classification criterion:
+++: Ki<3 nM
++: Ki in the range 3-30 nM
+: Ki>30 nM.

The invention claimed is:
1. A compound of formula (I)

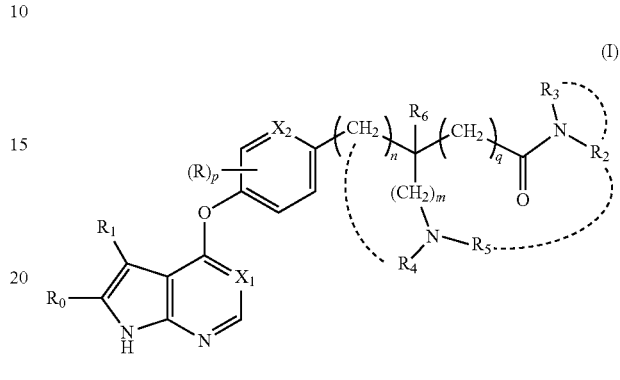

wherein
$X_1$, and $X_2$ are at each occurrence independently a CH group or a nitrogen atom;
p is zero or an integer from 1 to 3;
n, q and m are zero or an integer from 1 to 2;
each R, when present, is an halogen;
$R_0$ and $R_1$ are independently selected from the group consisting of
—H,
halogen,
—NR$_7$R$_8$,
—CN,
(C$_1$-C$_6$) alkyl,
(C$_1$-C$_6$) haloalkyl,
(C$_1$-C$_6$) hydroxyalkyl,
(C$_1$-C$_6$) aminoalkyl,
(C$_1$-C$_6$) alkoxy-(C$_1$-C$_6$) alkyl
(C$_3$-C$_{10}$) cycloalkyl,
(C$_2$-C$_6$) alkenyl,
(C$_5$-C$_7$) cycloalkenyl,
(C$_2$-C$_6$) alkynyl,
(C$_2$-C$_6$) hydroxyalkynyl,
aryl, heteroaryl and (C$_3$-C$_6$) heterocycloalkyl
each of which aryl, heteroaryl and (C$_3$-C$_6$) heterocycloalkyl
being in its turn optionally and independently substituted with one or more groups selected from
halogen,
—OH,
—CN,
—NR$_7$R$_8$,
—CH$_2$NR$_7$R$_8$,
(C$_1$-C$_6$) alkyl,
(C$_1$-C$_6$) haloalkyl,
(C$_1$-C$_6$) hydroxyalkyl,
(C$_2$-C$_6$) alkenyl,
(C$_2$-C$_6$) alkynyl,
(C$_2$-C$_6$) hydroxyalkynyl;
$R_2$ and $R_3$, the same or different, are selected from the group consisting of
—H,
(C$_1$-C$_6$) alkyl,
(C$_1$-C$_6$) haloalkyl, ($C_1$-$C_6$) hydroxyalkyl,
($C_1$-$C_6$) aminoalkyl,
($C_1$-$C_6$) alkoxy ($C_1$-$C_6$) alkyl,
($C_3$-$C_{10}$)cycloalkyl,
($C_3$-$C_8$)heterocycloalkyl,
aryl,
heteroaryl,
aryl($C_1$-$C_6$)alkyl,
aryl oxyl (C1-C6) alkyl,
heteroaryl($C_1$-$C_6$)alkyl,
($C_3$-$C_8$)cycloalkyl($C_1$-$C_6$)alkyl,
($C_3$-$C_8$)heterocycloalkyl-($C_1$-$C_6$)alkyl
each of said aryl, heteroaryl, cycloalkyl, heterocycloalkyl is further optionally substituted by one or more group selected independently from halogen, —CN, —OH, ($C_1$-$C_8$)alkyl, ($C_1$-$C_6$) haloalkyl, ($C_1$-$C_{10}$)alkoxy, aryl, aryl($C_1$-$C_6$)alkyl, carbamoyl, ($C_1$-$C_6$) aminoalkyl, ($C_1$-$C_6$) hydroxyalkyl; or alternatively,
$R_2$ and $R_3$, taken together with the nitrogen atom they are linked to, form a mono- or bi-cyclic saturated or partially saturated heterocyclic radical, wherein at least one further ring carbon atom in the said heterocyclic radical is optionally replaced by at least one further heteroatom independently selected from N, NH, S or O and/or may bear an -oxo (=O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic, ring;
said heterocyclic radical being optionally in its turn further substituted with one or more groups selected from the group consisting of
halogen,
hydroxyl,
—$NR_7R_8$,
—$CH_2NR_7R_8$,
($C_1$-$C_6$) alkyl,
($C_1$-$C_6$) haloalkyl,
($C_1$-$C_6$) hydroxyalkyl,
($C_2$-$C_6$) alkenyl,
($C_2$-$C_6$) alkynyl,
($C_2$-$C_6$) hydroxyalkynyl,
($C_1$-$C_6$) alkoxy ($C_1$-$C_6$) alkyl,
($C_1$-$C_6$) alkanoyl,
carbamoyl,
($C_3$-$C_6$) cycloalkyl-carbonyl,
($C_3$-$C_6$) heterocycloalkyl-carbonyl,
aryl($C_1$-$C_6$)alkyl,
aryl alkanoyl,
arylsulfonyl,
heteroaryl($C_1$-$C_6$)alkyl,
heteroaryl-carbonyl
heteroaryloxyl,
($C_3$-$C_6$) cycloalkyl,
($C_3$-$C_8$)cycloalkyl($C_1$-$C_6$)alkyl,
($C_3$-$C_6$) heterocycloalkyl-($C_1$-$C_6$) alkyl,
aryl and heteroaryl
each of said cycloalkyl, aryl and heteroaryl being further optionally substituted by halogen, ($C_1$-$C_8$)alkyl, ($C_1$-$C_{10}$)alkoxy, ($C_1$-$C_6$)alkylthio, ($C_1$-$C_6$) aminoalkyl, ($C_1$-$C_6$) aminoalkoxyl, carbamoyl, ($C_1$-$C_6$)alkyl-sulfonyl;
$R_4$ and $R_5$ are at each occurrence independently selected in the group consisting of
H,
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) alkoxyl,
($C_1$-$C_6$) alkoxy-($C_1$-$C_6$) alkyl,
($C_3$-$C_6$) cycloalkyl-($C_1$-$C_6$) alkyl
($C_3$-$C_6$) heterocycloalkyl-($C_1$-$C_6$) alkyl,
($C_3$-$C_6$) cycloalkyl-carbonyl
($C_3$-$C_6$) heterocycloalkyl-carbonyl,
aryl, heteroaryl and ($C_3$-$C_6$) heterocycloalkyl;
wherein any of said ($C_3$-$C_6$) cycloalkyl, aryl, heteroaryl and ($C_3$-$C_6$) heterocycloalkyl in its turn is optionally and independently substituted with one or more groups selected from
halogen,
—OH,
($C_1$-$C_6$) alkyl;
or
when $R_6$ is H, n is 1 and q is 0, $R_4$ can optionally link to the carbon atom of the methylene group via a divalent bridge —$CH_2$— when m is 1, or via a —$CH_2$—$CH_2$— when m is 0, thus forming a pyrrolidine divalent group a1, or a2

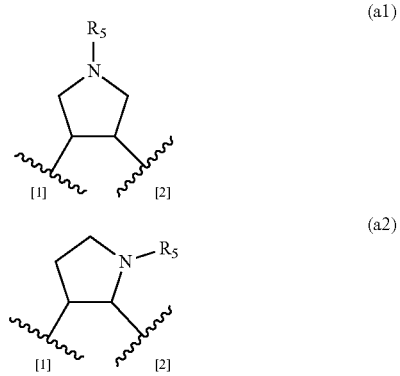

[1] and [2] being respectively the point of attachment to the phenyl and to the carboxamide group;
or
when $R_6$ is H, $R_5$ can link to the group $R_2$ to form a methylene —$CH_2$— bridge, thus forming a tetrahydropyrimidinone divalent group b1 when q is one, m and n are zero or b2 when m and n are 1 and q is zero:

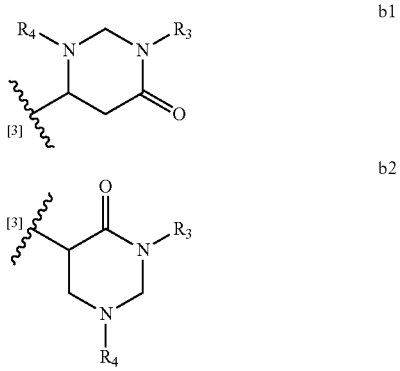

[3] being the point of attachment to the rest of molecule;
$R_6$ is selected from the group consisting of —H, ($C_1$-$C_6$) alkyl, ($C_1$-$C_6$) haloalkyl;

$R_7$ and $R_8$ are at each occurrence independently selected in the group H,
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) alkoxyl,
($C_1$-$C_6$) alkoxy-($C_1$-$C_6$) alkyl,
($C_3$-$C_6$) heterocycloalkyl-($C_1$-$C_6$) alkyl,
aryl, heteroaryl and ($C_3$-$C_6$) heterocycloalkyl;
wherein any of said aryl, heteroaryl and ($C_3$-$C_6$) heterocycloalkyl in its turn is optionally and independently substituted with one or more groups selected from
halogen,
—OH,
($C_1$-$C_6$) alkyl; or
$R_7$ and $R_8$ are taken together with the nitrogen atom they are linked to, to form a 4 to 6 membered heterocyclic radical, wherein at least one further ring carbon atom in the said heterocyclic radical may be replaced by at least one group selected from N, S or O; said heterocyclic radical can be further optionally substituted by a group selected from
H,
—CN,
halogen,
oxo,
—$NR_7R_8$
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) alkoxyl,
($C_1$-$C_6$) alkoxy-($C_1$-$C_6$) alkyl,
alkanoyl;
or pharmaceutically acceptable salts and solvates thereof.

2. A compound according to claim 1 wherein each of $X_1$ and $X_2$ is a CH group, all the other variables being as defined in claim 1, or pharmaceutically acceptable salt and solvates thereof.

3. A compound according to claim 1, wherein
$X_1$, and $X_2$ are both a CH group;
p is zero or 1;
n, q and m are zero or an integer from 1 to 2;
each R, when present, is halogen;
$R_0$ and $R_1$ are independently selected from the group consisting of
—H,
—CN,
($C_1$-$C_6$) alkyl;
$R_2$ and $R_3$, the same or different, are selected from the group consisting of
—H,
($C_1$-$C_6$) alkyl,
($C_1$-$C_6$) aminoalkyl,
($C_1$-$C_6$) alkoxy ($C_1$-$C_6$) alky,
($C_3$-$C_{10}$)cycloalkyl,
($C_3$-$C_8$)heterocycloalkyl,
Aryl,
each of said aryl, cycloalkyl, heterocycloalkyl is further optionally substituted by one or more group selected independently from ($C_1$-$C_8$) alkyl, and ($C_1$-$C_6$) haloalkyl, or
$R_2$ and $R_3$, in the alternative, taken together with the nitrogen atom they are linked to, form a mono- or bi-cyclic saturated, at least one further ring carbon atom in the said heterocyclic radical is optionally replaced by at least one further group selected from N and NH;
said heterocyclic radical being optionally in its turn further substituted with one or more groups selected from the group consisting of
($C_1$-$C_6$) alkyl,
aryl($C_1$-$C_6$)alkyl,
heteroaryl($C_1$-$C_6$)alkyl,
($C_3$-$C_6$) cycloalkyl,
$R_4$ and $R_5$ are at each occurrence independently selected in the group consisting of
H,
($C_1$-$C_6$) alkyl,
$R_6$ is —H;
$R_7$ and $R_8$ are H.

4. A compound according to claim 3,
wherein
$X_1$, and $X_2$ are both a CH group;
p is zero or 1;
n, q and m are zero or an integer from 1 to 2;
each R, when present, is fluorine;
$R_0$ and $R_1$ are independently selected from the group consisting of
—H,
—CN,
($C_1$-$C_6$) alkyl, which is methyl,
$R_2$ and $R_3$, the same or different, are selected from the group consisting of
—H,
($C_1$-$C_6$) alkyl which is methyl,
($C_1$-$C_6$) aminoalkyl which is dimethylaminopropyl,
($C_1$-$C_6$) alkoxy ($C_1$-$C_6$) alkyl which is methoxypropyl,
($C_3$-$C_{10}$)cycloalkyl which is cyclohexyl,
($C_3$-$C_8$)heterocycloalkyl which is piperidinyl, tetrahydropyranyl,
Aryl which is phenyl,
each of said aryl, cycloalkyl, heterocycloalkyl is further optionally substituted by one or more group selected independently from methyl and trifluoromethyl, or
$R_2$ and $R_3$, in the alternative, taken together with the nitrogen atom they are linked to, form a mono- or bi-cyclic saturated, at least one further ring carbon atom in the said heterocyclic radical is optionally replaced by at least one further heteroatom which is N,
said heterocyclic radical being optionally in its turn further substituted with one or more groups selected from the group consisting of
($C_1$-$C_6$) alkyl which is methyl,
aryl($C_1$-$C_6$)alkyl which is phenylmethyl,
heteroaryl($C_1$-$C_6$)alkyl which is (pyridinyl)methyl,
($C_3$-$C_6$) cycloalkyl which is cyclopropyl;
$R_4$ and $R_5$ are at each occurrence independently selected in the group consisting of
H,
($C_1$-$C_6$) alkyl which is methyl,
$R_6$ is —H;
$R_7$ and $R_8$ are H.

5. A compound according to claim 1
wherein, when $R_6$ is H, n is 1 and q is 0, R4 links to the carbon atom of the methylene group via a divalent bridge —$CH_2$— when m is 1, or via a —$CH_2$—$CH_2$— when m is 0, forming a pyrrolidine divalent group, represented by the formula (Ib) and (Ic):

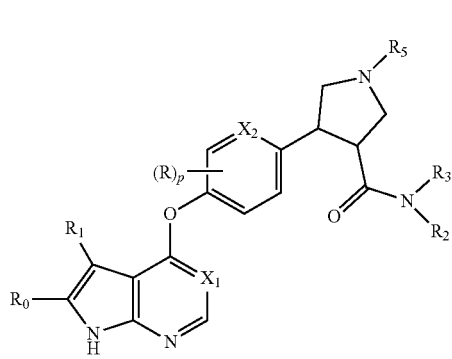
(Ib)

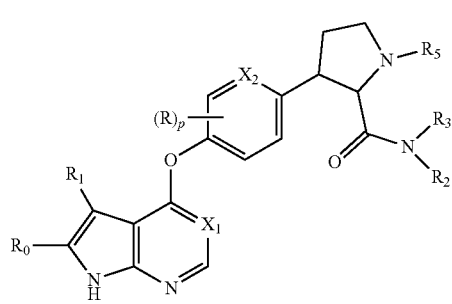
(Ic)

wherein $X_1$ and $X_2$ are both a CH group;

p is zero;

$R_0$ and $R_1$ are independently selected from the group consisting of

—H, $(C_1-C_6)$ alkyl, $R_2$ and $R_3$, the same or different, are selected from the group consisting of

—H, $(C_1-C_6)$ alkyl, $(C_1-C_6)$ aminoalkyl $(C_1-C_6)$ alkoxy $(C_1-C_6)$ alkyl, $(C_3-C_8)$heterocycloalkyl, aryl$(C_1-C_6)$alkyl, aryl oxyl (C1-C6) alkyl, heteroaryl$(C_1-C_6)$alkyl, each of said heterocycloalkyl is further optionally substituted by one or more $(C_1-C_8)$ alkyl group, or $R_2$ and $R_3$, in the alternative, taken together with the nitrogen atom they are linked to, form a mono-cyclic saturated, wherein at least one further ring carbon atom in the said heterocyclic radical is optionally replaced by at least one further group selected from N and NH, $R_5$ is selected in the group consisting of

H;

$(C_1-C_6)$ alkyl.

6. A compound according to claim 5 wherein, when $R_6$ is H, n is 1 and q is 0, R4 links to the carbon atom of the methylene group via a divalent bridge —CH$_2$— when m is 1, or via a —CH$_2$—CH$_2$— when m is 0, forming a pyrrolidine divalent group, represented by the formula (Ib) and (Ic):

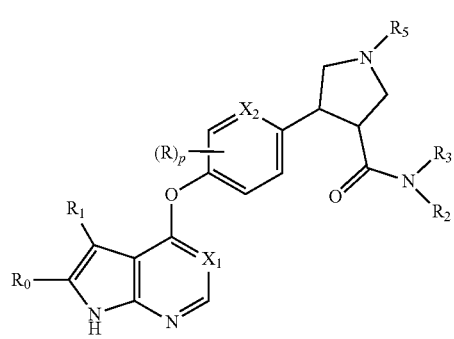
(Ib)

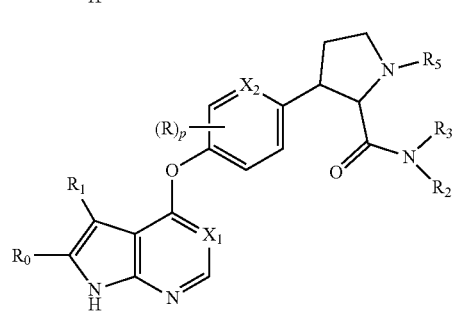
(Ic)

wherein $X_1$ and $X_2$ are both a CH group;

p is zero;

$R_0$ and $R_1$ are independently selected from the group consisting of

—H, $(C_1-C_6)$ alkyl which is methyl, $R_2$ and $R_3$, the same or different, are selected from the group consisting of

—H, $(C_1-C_6)$ alkyl which is methyl, $(C_1-C_6)$ aminoalkyl which is dimethylaminopropyl, $(C_1-C_6)$ alkoxy $(C_1-C_6)$ alkyl which is methoxypropyl, $(C_3-C_8)$heterocycloalkyl which is piperidinyl, tetrahydropyranyl, aryl$(C_1-C_6)$alkyl which is phenylmethyl, phenylethyl, aryl oxyl (C1-C6) alkyl which is phenoxyethyl, heteroaryl$(C_1-C_6)$alkyl which is (pyridinyl)ethyl, each of said heterocycloalkyl is further optionally substituted by one or more methyl group, or $R_2$ and $R_3$, in the alternative, taken together with the nitrogen atom they are linked to, form a mono-cyclic saturated, wherein at least one further ring carbon atom in the said heterocyclic radical is optionally replaced by NH, $R_5$ is selected in the group consisting of

H;

methyl.

7. A compound according to claim 1 wherein, when $R_6$ is H, $R_5$ links to the group $R_2$ to form a methylene —CH$_2$— bridge, thus forming a tetrahydropyrimidinone divalent group, represented by the formula (Id) when q is 1, m and n are zero, and (Ie) when m and n are 1 and q is zero:

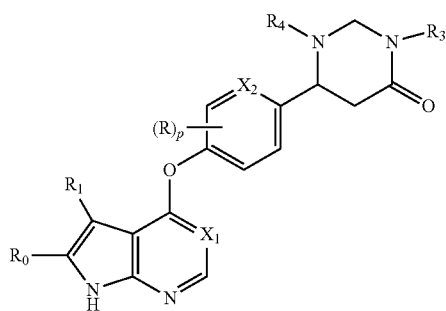

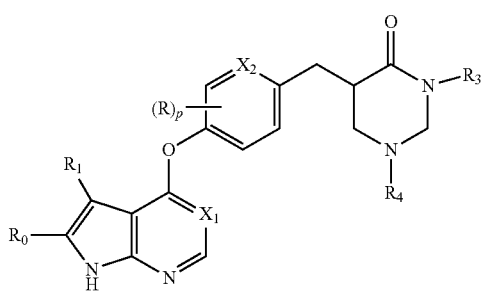

wherein
X$_1$, and X$_2$ are both a CH group;
p is zero or 1;
each R, when present, is halogen;
R$_0$ and R$_1$ are independently selected from the group consisting of
—H,
—CN,
(C$_1$-C$_6$) alkyl,
R$_3$, is selected from the group consisting of
(C$_1$-C$_6$) aminoalkyl,
(C$_1$-C$_6$) alkoxy (C$_1$-C$_6$) alkyl,
(C$_3$-C$_8$)heterocycloalkyl,
heteroaryl(C$_1$-C$_6$)alkyl,
each of said heterocycloalkyl is further optionally substituted by one or more (C$_1$-C$_8$) alkyl group;
R$_4$ is selected in the group consisting of
H,
(C$_1$-C$_6$) alkyl.

8. A compound according to claim 7
wherein, when R$_4$ is H, R$_6$ is H, R$_5$ links to the group R$_2$ to form a methylene —CH$_2$— bridge, thus forming a tetrahydropyrimidinone divalent group, represented by the formula (Id) when q is 1, m and n are zero, and (Ie) when m and n are 1 and q is zero:

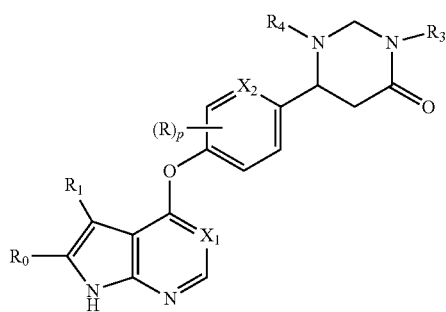

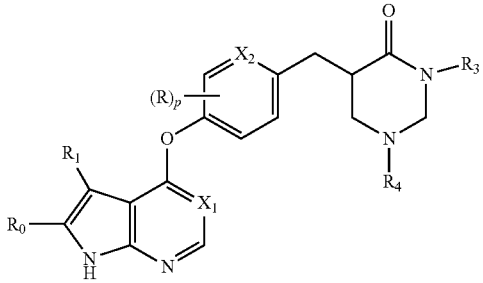

wherein
X$_1$, and X$_2$ are both a CH group;
p is zero or 1;
each R, when present, is fluorine;
R$_0$ and R$_1$ are independently selected from the group consisting of
—H,
—CN,
methyl,
R$_3$, is selected from the group consisting of
(C$_1$-C$_6$) aminoalkyl which is dimethylaminopropyl,
(C$_1$-C$_6$) alkoxy (C$_1$-C$_6$) alkyl which is methoxypropyl,
(C$_3$-C$_8$)heterocycloalkyl which is piperidinyl,
heteroaryl(C$_1$-C$_6$)alkyl which is (pyridinyl)ethyl
each of said heterocycloalkyl is further optionally substituted by one or more methyl group;
R$_4$ is H.

9. A compound according to claim 1 selected from:
3-amino-2-(4-((3-methyl-1H-pyrrolo[2,3-b]pyridin-4-yl)oxy)benzyl)-1-(4-methylpiperazin-1-yl)propan-1-one;
3-amino-1-(4-cyclopropylpiperazin-1-yl)-2-(4-((3-methyl-1H-pyrrolo[2,3-b]pyridin-4-yl)oxy)benzyl)propan-1-one;
3-amino-2-(3-fluoro-4-((3-methyl-1H-pyrrolo[2,3-b]pyridin-4-yl)oxy)benzyl)-N-(1-methylpiperidin-4-yl)propanamide;
3-amino-2-(3-fluoro-4-((3-methyl-1H-pyrrolo[2,3-b]pyridin-4-yl)oxy)benzyl)-1-((1S,4S)-5-methyl-2,5-diazabicyclo[2.2.1]heptan-2-yl)propan-1-one;
3-amino-2-(3-fluoro-4-((3-methyl-1H-pyrrolo[2,3-b]pyridin-4-yl)oxy)benzyl)-1-(4-(pyridin-2-ylmethyl)piperazin-1-yl)propan-1-one;
3-amino-1-(4-benzylpiperazin-1-yl)-2-(4-((2-methyl-1H-pyrrolo[2,3-b]pyridin-4-yl)oxy)benzyl)propan-1-one;
3-amino-1-(4-benzylpiperazin-1-yl)-3-(4-((3-methyl-1H-pyrrolo[2,3-b]pyridin-4-yl)oxy)phenyl)propan-1-one;
2-(4-((1H-pyrrolo[2,3-b]pyridin-4-yl)oxy)phenyl)-2-amino-N-cyclohexylacetamide;
2-(4-((1H-pyrrolo[2,3-b]pyridin-4-yl)oxy)phenyl)-2-amino-N-phenylacetamide;
2-(4-((1H-pyrrolo[2,3-b]pyridin-4-yl)oxy)phenyl)-2-amino-N-(4-(trifluoromethyl)phenyl)acetamide;
2-(4-((1H-pyrrolo[2,3-b]pyridin-4-yl)oxy)phenyl)-2-amino-1-(4-methylpiperazin-1-yl)ethanone;
2-(4-((1H-pyrrolo[2,3-b]pyridin-4-yl)oxy)phenyl)-2-amino-N,N-dimethylacetamide;
2-(4-((1H-pyrrolo[2,3-b]pyridin-4-yl)oxy)phenyl)-2-amino-N-(tetrahydro-2H-pyran-4-yl)acetamide;
2-(4-((1H-pyrrolo[2,3-b]pyridin-4-yl)oxy)phenyl)-2-amino-N-(1-methylpiperidin-4-yl)acetamide;
4-amino-1-(4-benzylpiperazin-1-yl)-3-(4-((3-methyl-1H-pyrrolo[2,3-b]pyridin-4-yl)oxy)phenyl)butan-1-one;

4-amino-1-(4-cyclopropylpiperazin-1-yl)-3-(4-((3-methyl-1H-pyrrolo[2,3-b]pyridin-4-yl)oxy)phenyl)butan-1-one;

rac-(3R,4S)-N-benzyl-4-(4-((3-methyl-1H-pyrrolo[2,3-b]pyridin-4-yl)oxy)phenyl)pyrrolidine-3-carboxamide;

rac-(3R,4S)-N-benzyl-N-methyl-4-(4-((3-methyl-1H-pyrrolo[2,3-b]pyridin-4-yl)oxy)phenyl)pyrrolidine-3-carboxamide;

rac-(2S,3R)-N-benzyl-3-(4-((3-methyl-1H-pyrrolo[2,3-b]pyridin-4-yl)oxy)phenyl)pyrrolidine-2-carboxamide;

rac-(2S,3R)-3-(4-((3-methyl-1H-pyrrolo[2,3-b]pyridin-4-yl)oxy)phenyl)-N-(2-(pyridin-4-yl)ethyl)pyrrolidine-2-carboxamide;

rac-(2S,3R)-N-(3-methoxypropyl)-3-(4-((3-methyl-1H-pyrrolo[2,3-b]pyridin-4-yl)oxy)phenyl)pyrrolidine-2-carboxamide;

rac-(2S,3R)-3-(4-((3-methyl-1H-pyrrolo[2,3-b]pyridin-4-yl)oxy)phenyl)-N-phenethylpyrrolidine-2-carboxamide;

rac-(2S,3R)-3-(4-((3-methyl-1H-pyrrolo[2,3-b]pyridin-4-yl)oxy)phenyl)-N-(2-phenoxyethyl)pyrrolidine-2-carboxamide;

rac-(2S,3R)-3-(4-((3-methyl-1H-pyrrolo[2,3-b]pyridin-4-yl)oxy)phenyl)-N-(tetrahydro-2H-pyran-4-yl)pyrrolidine-2-carboxamide;

rac-(2S,3R)-3-(4-((3-methyl-1H-pyrrolo[2,3-b]pyridin-4-yl)oxy)phenyl)-N-(1-methylpiperidin-4-yl)pyrrolidine-2-carboxamide;

rac-(2R,3S)-N-(3-(dimethylamino)propyl)-3-(4-((3-methyl-1H-pyrrolo[2,3-b]pyridin-4-yl)oxy)phenyl)pyrrolidine-2-carboxamide;

rac-((2S,3R)-3-(4-((3-methyl-1H-pyrrolo[2,3-b]pyridin-4-yl)oxy)phenyl)pyrrolidin-2-yl)(piperazin-1-yl)methanone;

3-amino-N-cyclohexyl-2-(3-fluoro-4-((3-methyl-1H-pyrrolo[2,3-b]pyridin-4-yl)oxy)benzyl)propanamide;

3-amino-1-(4-benzylpiperazin-1-yl)-2-(3-fluoro-4-((3-methyl-1H-pyrrolo[2,3-b]pyridin-4-yl)oxy)benzyl)propan-1-one;

3-amino-1-(4-benzylpiperazin-1-yl)-2-(4-((3-methyl-1H-pyrrolo[2,3-b]pyridin-4-yl)oxy)benzyl)propan-1-one;

3-amino-N-cyclohexyl-2-(4-((3-methyl-1H-pyrrolo[2,3-b]pyridin-4-yl)oxy)benzyl)propanamide;

2-(4-((1H-pyrrolo[2,3-b]pyridin-4-yl)oxy)benzyl)-3-amino-1-(4-benzylpiperazin-1-yl)propan-1-one;

2-(4-((1H-pyrrolo[2,3-b]pyridin-4-yl)oxy)benzyl)-3-amino-N-cyclohexylpropanamide;

2-(4-((1H-pyrrolo[2,3-b]pyridin-4-yl)oxy)benzyl)-3-amino-N-(tetrahydro-2H-pyran-4-yl)propanamide;

2-(4-((1H-pyrrolo[2,3-b]pyridin-4-yl)oxy)benzyl)-3-amino-N-(3-methoxypropyl)propanamide;

1-(4-benzylpiperazin-1-yl)-2-(4-((3-methyl-1H-pyrrolo[2,3-b]pyridin-4-yl)oxy)benzyl)-3-(methylamino)propan-1-one;

1-(4-benzylpiperazin-1-yl)-3-(dimethylamino)-2-(4-((3-methyl-1H-pyrrolo[2,3-b]pyridin-4-yl)oxy)benzyl)propan-1-one;

3-(3-(dimethylamino)propyl)-6-(4-((3-methyl-1H-pyrrolo[2,3-b]pyridin-4-yl)oxy)phenyl)tetrahydropyrimidin-4(1H)-one;

3-(3-methoxypropyl)-6-(4-((3-methyl-1H-pyrrolo[2,3-b]pyridin-4-yl)oxy)phenyl)tetrahydropyrimidin-4(1H)-one;

6-(4-((3-methyl-1H-pyrrolo[2,3-b]pyridin-4-yl)oxy)phenyl)-3-(2-(pyridin-4-yl)ethyl)tetrahydropyrimidin-4(1H)-one;

3-(3-(dimethylamino)propyl)-5-(3-fluoro-4-((3-methyl-1H-pyrrolo[2,3-b]pyridin-4-yl)oxy)benzyl)tetrahydropyrimidin-4(1H)-one;

5-(3-fluoro-4-((3-methyl-1H-pyrrolo[2,3-b]pyridin-4-yl)oxy)benzyl)-3-(3-methoxypropyl)tetrahydropyrimidin-4(1H)-one;

5-(3-fluoro-4-((3-methyl-1H-pyrrolo[2,3-b]pyridin-4-yl)oxy)benzyl)-3-(2-(pyridin-4-yl)ethyl)tetrahydropyrimidin-4(1H)-one;

3-amino-2-(4-((3-cyano-1H-pyrrolo[2,3-b]pyridin-4-yl)oxy)benzyl)-N-(3-(dimethylamino)propyl)propanamide;

4-(4-((1-(3-(dimethylamino)propyl)-6-oxohexahydropyrimidin-5-yl)methyl)phenoxy)-1H-pyrrolo[2,3-b]pyridine-3-carbonitrile;

3-amino-2-(4-((3-cyano-1H-pyrrolo[2,3]pyridin-4-yl)oxy)benzyl)-N-(1-methylpiperidin-4-yl)propanamide;

4-(4-((1-(1-methylpiperidin-4-yl)-6-oxohexahydropyrimidin-5-yl)methyl)phenoxy)-1H-pyrrolo[2,3-b]pyridine-3-carbonitrile;

4-(4-(2-(aminomethyl)-3-((1S,4S)-5-methyl-2,5-diazabicyclo[2.2.1]heptan-2-yl)-3-oxopropyl)phenoxy)-1H-pyrrolo[2,3-b]pyridine-3-carbonitrile;

4-(4-(2-(aminomethyl)-3-oxo-3-(4-(pyridin-2-ylmethyl)piperazin-1-yl)propyl)phenoxy)-1H-pyrrolo[2,3-b]pyridine-3-carbonitrile;

rac-(3R,4S)-N-benzyl-1-methyl-4-(4-((3-methyl-1H-pyrrolo[2,3-b]pyridin-4-yl)oxy)phenyl)pyrrolidine-3-carboxamide;

(1st eluting) 3-amino-2-(3-fluoro-4-((3-methyl-1H-pyrrolo[2,3-b]pyridin-4-yl)oxy)benzyl)-1-((1S,4S)-5-methyl-2,5-diazabicyclo[2.2.1]heptan-2-yl)propan-1-one;

(2nd eluting) 3-amino-2-(3-fluoro-4-((3-methyl-1H-pyrrolo[2,3-b]pyridin-4-yl)oxy)benzyl)-1-((1S,4S)-5-methyl-2,5-diazabicyclo[2.2.1]heptan-2-yl)propan-1-one;

(1st eluting) 3-amino-2-(3-fluoro-4-((3-methyl-1H-pyrrolo[2,3-b]pyridin-4-yl)oxy)benzyl)-1-(4-(pyridin-2-ylmethyl)piperazin-1-yl)propan-1-one;

(2nd eluting) 3-amino-2-(3-fluoro-4-((3-methyl-1H-pyrrolo[2,3-b]pyridin-4-yl)oxy)benzyl)-1-(4-(pyridin-2-ylmethyl)piperazin-1-yl)propan-1-one;

(1st eluting) 3-amino-1-(4-benzylpiperazin-1-yl)-3-(4-((3-methyl-1H-pyrrolo[2,3-b]pyridin-4-yl)oxy)phenyl)propan-1-one;

(2nd eluting) 3-amino-1-(4-benzylpiperazin-1-yl)-3-(4-((3-methyl-1H-pyrrolo[2,3-b]pyridin-4-yl)oxy)phenyl)propan-1-one;

(1st eluting) 3-amino-1-(4-benzylpiperazin-1-yl)-2-(3-fluoro-4-((3-methyl-1H-pyrrolo[2,3-b]pyridin-4-yl)oxy)benzyl)propan-1-one;

(2nd eluting) 3-amino-1-(4-benzylpiperazin-1-yl)-2-(3-fluoro-4-((3-methyl-1H-pyrrolo[2,3-b]pyridin-4-yl)oxy)benzyl)propan-1-one;

(1st eluting) 2-(4-((1H-pyrrolo[2,3-b]pyridin-4-yl)oxy)benzyl)-3-amino-1-(4-benzylpiperazin-1-yl)propan-1-one;

(2nd eluting) 2-(4-((1H-pyrrolo[2,3-b]pyridin-4-yl)oxy)benzyl)-3-amino-1-(4-benzylpiperazin-1-yl)propan-1-one;

(1st eluting) (3R,4S)-N-benzyl-4-(4-((3-methyl-1H-pyrrolo[2,3-b]pyridin-4-yl)oxy)phenyl)pyrrolidine-3-carboxamide;

(2nd eluting) (3R,4S)-N-benzyl-4-(4-((3-methyl-1H-pyrrolo[2,3-b]pyridin-4-yl)oxy)phenyl)pyrrolidine-3-carboxamide;

or pharmaceutically acceptable salts and solvates thereof.

10. A pharmaceutical composition comprising a compound as defined in claim 1, or a pharmaceutically acceptable salt thereof, either alone or in combination with another one or more active ingredient, in admixture with one or more pharmaceutically acceptable carrier or excipient.

11. A compound according to claim 1 for use in the treatment of pulmonary disease selected from the group consisting of asthma, chronic obstructive pulmonary disease COPD, idiopathic pulmonary fibrosis (IPF), pulmonary hypertension (PH) and specifically Pulmonary Arterial Hypertension (PAH).

12. A combination of a compound as defined in claim 1 with one or more active ingredients selected from the classes consisting of organic nitrates and NO donors; inhaled NO; stimulator of soluble guanylate cyclase (sGC); prostaciclin analogue PGI2 and agonist of prostacyclin receptors; compounds that inhibit the degradation of cyclic guanosine monophosphate (cGMP) and/or cyclic adenosine monophosphate (cAMP); human neutrophilic elastase inhibitors; compounds inhibiting the signal transduction cascade; active substances for lowering blood pressure; neutral endopeptidase inhibitor; osmotic agents; ENaC blockers; anti-inflammatory including corticosteroids and antagonists of chemokine receptors; bronchodilators; antihistamine drugs; anti-tussive drugs; antibiotics and DNase drug substances and selective cleavage agents; agents that inhibit ALK5 and/or ALK4 phosphorylation of Smad2 and Smad3; tryptophan hydroylase 1 (TPH1) inhibitors and multi-kinase inhibitors.

13. A pharmaceutical composition according to claim 10 suitable to be administered by inhalation, such as inhalable powders, propellant-containing metering aerosols or propellant-free inhalable formulations.

14. A device comprising the pharmaceutical composition according to claim 10, which may be a single- or multi-dose dry powder inhaler, a metered dose inhaler and a soft mist nebulizer.

\* \* \* \* \*